US012668829B2

(12) United States Patent
Epperson et al.

(10) Patent No.: US 12,668,829 B2
(45) Date of Patent: Jun. 30, 2026

(54) DEVICES AND METHODS FOR DETERMINING PARTICLE CONCENTRATION IN A SAMPLE

(71) Applicants: Roche Molecular Systems, Inc., Pleasanton, CA (US); Sandstone Diagnostics, Inc., Pleasanton, CA (US)

(72) Inventors: Jon Epperson, Pleasanton, CA (US); Laura Fredriksen, Pleasanton, CA (US); Kyungjin Hong, Pleasanton, CA (US); Jenq-Thun Li, Pleasanton, CA (US); Bhairavi Rajiv Parikh, Pleasanton, CA (US); Ulrich Schaff, Pleasanton, CA (US)

(73) Assignees: Roche Molecular Systems, Inc., Pleasanton, CA (US); Sandstone Diagnostics, Inc., Pleasanton, CA (US)

( * ) Notice: Subject to any disclaimer, the term of this patent is extended or adjusted under 35 U.S.C. 154(b) by 1165 days.

(21) Appl. No.: 17/051,426

(22) PCT Filed: May 9, 2019

(86) PCT No.: PCT/EP2019/061902
§ 371 (c)(1),
(2) Date: Oct. 28, 2020

(87) PCT Pub. No.: WO2019/215273
PCT Pub. Date: Nov. 14, 2019

(65) Prior Publication Data
US 2021/0222224 A1      Jul. 22, 2021

Related U.S. Application Data

(60) Provisional application No. 62/785,752, filed on Dec. 28, 2018, provisional application No. 62/669,357, filed on May 9, 2018.

(51) Int. Cl.
*B01L 3/00*          (2006.01)
*C12Q 1/06*          (2006.01)
(Continued)

(52) U.S. Cl.
CPC .......... *C12Q 1/06* (2013.01); *B01L 3/502761* (2013.01); *C12Q 1/18* (2013.01);
(Continued)

(58) Field of Classification Search
CPC ....... C12Q 1/06; C12Q 1/18; B01L 3/502761; B01L 2200/0652; B01L 2300/0809;
(Continued)

(56) References Cited

U.S. PATENT DOCUMENTS 3,122,420 A    2/1964   Rebar et al.
3,826,574 A    7/1974   Brown, Jr.
(Continued)

FOREIGN PATENT DOCUMENTS

CN        1859961 A      11/2006
CN      101438164 A       5/2009
(Continued)

OTHER PUBLICATIONS

Sigma-Aldrich: Pluronic F-127, retrieved from https://www.sigmaaldrich.com/US/en/product/sigma/p2443 (Year: 2024).*
(Continued)

*Primary Examiner* — Elizabeth A Robinson
*Assistant Examiner* — Sophia Y Lyle
(74) *Attorney, Agent, or Firm* — Daniel E. Agnew

(57) ABSTRACT

A cartridge for determining a concentration of target cells within a sample includes a separation portion and a detection portion. The separation portion includes a first and second surface defining a separation chamber. The separation portion can contain a density medium having a density greater than a density of a first portion of the sample and less than
(Continued)

a density of a second portion of the sample (that includes the target cells). The separation chamber can be fluidically coupled to an inlet reservoir such that the sample can pass from the inlet reservoir to the separation chamber during rotation. The detection portion includes a detection surface that forms a boundary of a detection chamber. The detection surface is nonparallel to the first surface such that the target cells impinge on the detection surface when passing into the detection chamber. The detection surface is configured to capture the target cells.

23 Claims, 22 Drawing Sheets

(51) Int. Cl.

| | | |
|---|---|---|
| *C12Q 1/18* | (2006.01) | |
| *G01N 1/30* | (2006.01) | |
| *G01N 15/06* | (2024.01) | |
| *G01N 33/487* | (2006.01) | |
| *G01N 15/01* | (2024.01) | |
| *G01N 15/075* | (2024.01) | |

(52) U.S. Cl.
CPC .............. *G01N 1/30* (2013.01); *G01N 15/06* (2013.01); *G01N 33/487* (2013.01); *B01L 2200/0652* (2013.01); *B01L 2300/0809* (2013.01); *B01L 2300/0861* (2013.01); *G01N 2001/302* (2013.01); *G01N 15/01* (2024.01); *G01N 15/075* (2024.01)

(58) Field of Classification Search
CPC ............. B01L 2300/0861; B01L 3/502; B01L 2200/0647; B01L 2300/047; B01L 2300/16; B01L 2400/0409; G01N 1/30; G01N 15/06; G01N 33/487; G01N 15/01; G01N 15/075; G01N 2001/302; G01N 33/569; G01N 33/54366; G01N 33/54373; G01N 33/56972; G01N 33/48735; G01N 15/0606; G01N 33/4875; G01N 35/00029; G01N 2035/00099; G01N 2035/00326; G01N 2035/00495; G01N 2035/0439; G01N 2333/195; G01N 15/042; G01N 2015/045; G01N 2001/4083
See application file for complete search history.

(56) References Cited

U.S. PATENT DOCUMENTS

| | | | |
|---|---|---|---|
| 4,057,148 | A | 11/1977 | Meyer et al. |
| 4,730,933 | A | 3/1988 | Lohr |
| 4,861,709 | A | 8/1989 | Ulitzur et al. |
| 5,086,233 | A | 2/1992 | Stafford et al. |
| 5,128,104 | A | 7/1992 | Murphy et al. |
| 5,139,745 | A | 8/1992 | Barr et al. |
| 5,188,455 | A | 2/1993 | Hammerstedt |
| 5,221,623 | A | 6/1993 | Legocki et al. |
| 5,242,660 | A | 9/1993 | Hsei |
| 5,364,591 | A | 11/1994 | Green et al. |
| 5,447,687 | A | 9/1995 | Lewis et al. |
| 5,494,646 | A | 2/1996 | Seymour |
| 5,498,525 | A | 3/1996 | Rees et al. |
| 5,582,969 | A | 12/1996 | Pearson et al. |
| 5,637,874 | A | 6/1997 | Honzawa et al. |
| 5,645,801 | A | 7/1997 | Bouma et al. |
| 5,656,424 | A | 8/1997 | Jurgensen et al. |
| 5,677,124 | A | 10/1997 | DuBois et al. |
| 5,730,938 | A | 3/1998 | Carbonari et al. |
| 5,736,388 | A | 4/1998 | Chada et al. |
| 5,814,022 | A | 9/1998 | Antanavich et al. |
| 5,824,468 | A | 10/1998 | Scherer et al. |
| 5,858,693 | A | 1/1999 | Cottingham |
| 5,912,119 | A | 6/1999 | Radman et al. |
| 5,917,592 | A | 6/1999 | Skiffington |
| 5,919,625 | A | 7/1999 | DuBois et al. |
| 5,939,262 | A | 8/1999 | Pasloske et al. |
| 5,965,415 | A | 10/1999 | Radman et al. |
| 5,989,499 | A | 11/1999 | Catanzariti et al. |
| 6,144,448 | A | 11/2000 | Mitoma |
| 6,189,580 | B1 | 2/2001 | Thibault et al. |
| 6,218,176 | B1 | 4/2001 | Berthold et al. |
| 6,271,034 | B1 | 8/2001 | Bardarov et al. |
| 6,300,061 | B1 | 10/2001 | Jacobs, Jr. et al. |
| 6,326,208 | B1 | 12/2001 | Denney |
| 6,335,166 | B1 | 1/2002 | Ammann et al. |
| 6,451,258 | B1 | 9/2002 | Malmqvist |
| 6,544,729 | B2 | 4/2003 | Sayler et al. |
| 6,555,312 | B1 | 4/2003 | Nakayama |
| 6,818,185 | B1 | 11/2004 | Petersen et al. |
| 7,001,719 | B2 | 2/2006 | Wicks et al. |
| 7,087,226 | B2 | 8/2006 | Ramachandran et al. |
| 7,244,612 | B2 | 7/2007 | Goodridge |
| 7,284,900 | B2 | 10/2007 | Mayer |
| 7,364,843 | B2 | 4/2008 | Peak |
| 7,695,682 | B2 | 4/2010 | Chojnacki et al. |
| 7,794,656 | B2 | 9/2010 | Liang et al. |
| 7,972,773 | B2 | 7/2011 | Madonna et al. |
| 8,021,343 | B2 | 9/2011 | Nalesso et al. |
| 8,092,990 | B2 | 1/2012 | Voorhees |
| 8,124,024 | B2 | 2/2012 | Ching et al. |
| 8,153,119 | B2 | 4/2012 | Collins et al. |
| 8,182,804 | B1 | 5/2012 | Collins et al. |
| 8,216,780 | B2 | 7/2012 | Smith et al. |
| 8,329,889 | B2 | 12/2012 | Collins et al. |
| 8,377,398 | B2 | 2/2013 | McDevitt et al. |
| 8,455,186 | B2 | 6/2013 | Smith et al. |
| 8,530,178 | B2 | 9/2013 | Sobek et al. |
| 8,829,473 | B1 | 9/2014 | Griswold et al. |
| 8,956,570 | B2 | 2/2015 | Wilson et al. |
| 9,034,257 | B2 | 5/2015 | Covey et al. |
| 9,034,575 | B2 | 5/2015 | Gisler et al. |
| 9,133,497 | B2 | 9/2015 | Frei et al. |
| 9,186,668 | B1 | 11/2015 | Schaff |
| 9,381,524 | B2 | 7/2016 | Bailey et al. |
| 9,388,453 | B2 | 7/2016 | Rey et al. |
| 9,481,903 | B2 | 11/2016 | Rey et al. |
| 9,500,579 | B1 | 11/2016 | Sommer et al. |
| 9,994,808 | B2 | 6/2018 | Parikh et al. |
| 10,161,948 | B2 | 12/2018 | Vacic et al. |
| D837,998 | S | 1/2019 | Schaff et al. |
| 2002/0001539 | A1 | 1/2002 | DiCesare et al. |
| 2003/0148536 | A1 | 8/2003 | Liang et al. |
| 2003/0162295 | A1 | 8/2003 | Wilson |
| 2004/0126783 | A1 | 7/2004 | Bortolin et al. |
| 2004/0191863 | A1 | 9/2004 | Cheng et al. |
| 2004/0214200 | A1 | 10/2004 | Brown et al. |
| 2005/0003346 | A1 | 1/2005 | Voorhees et al. |
| 2005/0048670 | A1 | 3/2005 | Wu et al. |
| 2005/0118719 | A1 | 6/2005 | Schmidt et al. |
| 2005/0155438 | A1 | 7/2005 | Belgardt |
| 2005/0180882 | A1 | 8/2005 | Tung et al. |
| 2005/0206895 | A1 | 9/2005 | Salmelainen |
| 2005/0273869 | A1 | 12/2005 | Court et al. |
| 2006/0204400 | A1* | 9/2006 | Blattert ............ B01L 3/502753 422/68.1 |
| 2006/0205085 | A1 | 9/2006 | Handique et al. |
| 2006/0210968 | A1 | 9/2006 | Goodridge |
| 2006/0257991 | A1 | 11/2006 | McDevitt et al. |
| 2007/0003950 | A1 | 1/2007 | Shen et al. |
| 2007/0072174 | A1 | 3/2007 | Sayler et al. |
| 2007/0136827 | A1 | 6/2007 | Collins et al. |
| 2007/0178450 | A1 | 8/2007 | Wheeler et al. |
| 2007/0263049 | A1 | 11/2007 | Preckel et al. |
| 2007/0292397 | A1 | 12/2007 | McNulty et al. |
| 2008/0003564 | A1 | 1/2008 | Chen et al. |
| 2008/0153096 | A1 | 6/2008 | Witty et al. |
| 2008/0241819 | A1 | 10/2008 | Smith |
| 2008/0261294 | A1 | 10/2008 | Noda et al. |

(56) References Cited

U.S. PATENT DOCUMENTS

| | | | |
|---|---|---|---|
| 2008/0272283 A1 | 11/2008 | Feldsine et al. | |
| 2008/0286757 A1 | 11/2008 | Gaisford et al. | |
| 2009/0123977 A1 | 5/2009 | Mendez et al. | |
| 2009/0155768 A1 | 6/2009 | Scholl et al. | |
| 2009/0155838 A1 | 6/2009 | Hale | |
| 2010/0028916 A1 | 2/2010 | Ambar et al. | |
| 2010/0055669 A1 | 3/2010 | Luque et al. | |
| 2010/0112549 A1 | 5/2010 | Rey et al. | |
| 2010/0112723 A1* | 5/2010 | Battrell | G01N 33/53 |
| | | | 422/68.1 |
| 2010/0133200 A1 | 6/2010 | Gin et al. | |
| 2010/0157303 A1 | 6/2010 | Ono | |
| 2010/0196877 A1 | 8/2010 | Smith et al. | |
| 2010/0225920 A1 | 9/2010 | Xia et al. | |
| 2010/0304986 A1 | 12/2010 | Chen et al. | |
| 2011/0033847 A1 | 2/2011 | Walsh et al. | |
| 2011/0076672 A1 | 3/2011 | Schofield | |
| 2011/0097702 A1 | 4/2011 | Voorhees | |
| 2011/0117025 A1 | 5/2011 | Dacosta et al. | |
| 2011/0183314 A1 | 7/2011 | Smith | |
| 2011/0236960 A1 | 9/2011 | Bird et al. | |
| 2012/0003630 A1 | 1/2012 | Collins et al. | |
| 2012/0058900 A1 | 3/2012 | Gisler et al. | |
| 2012/0071342 A1 | 3/2012 | Lochhead et al. | |
| 2012/0134975 A1 | 5/2012 | Hyde et al. | |
| 2012/0143024 A1 | 6/2012 | Phillips et al. | |
| 2012/0225423 A1 | 9/2012 | Schwoebel et al. | |
| 2012/0252699 A1 | 10/2012 | Jaffrey et al. | |
| 2012/0288866 A1 | 11/2012 | Kozma et al. | |
| 2012/0288897 A1 | 11/2012 | Ching et al. | |
| 2012/0328576 A1 | 12/2012 | Jayasheela et al. | |
| 2013/0122549 A1 | 5/2013 | Lu et al. | |
| 2014/0134656 A1 | 5/2014 | Dortet et al. | |
| 2014/0154816 A1* | 6/2014 | Schaff | G01N 21/6428 |
| | | | 422/69 |
| 2014/0224710 A1* | 8/2014 | Di Carlo | G01N 1/4077 |
| | | | 209/132 |
| 2014/0272928 A1 | 9/2014 | Rey et al. | |
| 2014/0352410 A1* | 12/2014 | Esteves Reis | B01L 3/50273 |
| | | | 494/17 |
| 2015/0104787 A1 | 4/2015 | Rey et al. | |
| 2015/0118708 A1* | 4/2015 | Hammond | B01L 3/502 |
| | | | 435/39 |
| 2015/0132795 A1 | 5/2015 | Griswold et al. | |
| 2015/0218613 A1 | 8/2015 | de Forest et al. | |
| 2016/0023204 A1* | 1/2016 | Schaff | G01N 35/04 |
| | | | 422/533 |
| 2016/0161479 A1* | 6/2016 | Harper | G01N 15/0205 |
| | | | 435/5 |
| 2016/0178619 A1* | 6/2016 | Koh | G01N 33/5304 |
| | | | 422/69 |
| 2016/0245836 A1 | 8/2016 | Ochranek et al. | |
| 2016/0281179 A1 | 9/2016 | Rey et al. | |
| 2016/0281180 A1 | 9/2016 | Rey et al. | |
| 2016/0320276 A9 | 11/2016 | Schaff et al. | |
| 2017/0152576 A1 | 6/2017 | Rey et al. | |
| 2017/0224435 A1 | 8/2017 | Godfrey et al. | |
| 2017/0233783 A1 | 8/2017 | de Forest et al. | |
| 2019/0194765 A1 | 6/2019 | Rey et al. | |
| 2019/0204349 A1 | 7/2019 | Ariyoshi et al. | |
| 2019/0316168 A1 | 10/2019 | Donnelly et al. | |
| 2021/0156842 A1* | 5/2021 | Schaff | G01N 33/491 |

FOREIGN PATENT DOCUMENTS

| | | |
|---|---|---|
| CN | 101939645 A | 1/2011 |
| EP | 0274527 | 7/1987 |
| EP | 0168933 | 4/1993 |
| JP | 07083831 | 3/1995 |
| JP | 2001337039 | 12/2001 |
| JP | 2010107418 | 5/2010 |
| WO | WO 1987/006706 | 11/1987 |
| WO | WO 1994/025572 | 11/1994 |
| WO | WO 1995/007457 | 3/1995 |
| WO | WO 2001/028683 | 4/2001 |
| WO | WO 2002/090995 | 11/2002 |
| WO | WO 2006/075996 | 7/2006 |
| WO | WO 2007/115378 | 10/2007 |
| WO | WO 2009/063681 | 5/2009 |
| WO | WO 2010/096584 | 8/2010 |
| WO | WO 2013/029153 A1 | 3/2013 |
| WO | WO 2013/126774 A2 | 8/2013 |
| WO | WO 2013/138763 A1 | 9/2013 |
| WO | WO 2013/173524 | 11/2013 |
| WO | WO 2013/192396 | 12/2013 |
| WO | WO 2019/240959 A1 | 12/2019 |
| WO | WO 2020/014190 A1 | 1/2020 |

OTHER PUBLICATIONS

International Search Report and Written Opinion for PCT/EP2019/061902, mailed Jul. 16, 2019.

KeyPath MRSA/MSSA Blood Culture Test—BT, 510(k) Summary, MicroPhage, Inc., Apr. 29, 2011, 15 pages.

Koh, Chung-Yan et al., "Centrifugal Microfluidic Platform for Ultrasensitive Detection of Botulinum Toxin," Analytical Chemistry, vol. 87, No. 2, pp. 922-928 (Jan. 5, 2015).

Vandercam, B. et al., "Amplification-based DNA analysis in the diagnosis of prosthetic joint infection," Journal of Molecular Diagnostics, 10(6):537-543 (2008).

Walsh, David I., III et al., "A centrifugal fluidic immunoassay for ocular diagnostics with an enzymatically hydrolyzed fluorogenic substrate," Lab on a Chip, vol. 14, No. 15, pp. 2673-2680 (Jan. 1, 2014).

* cited by examiner

Before
Rotation

After
Rotation

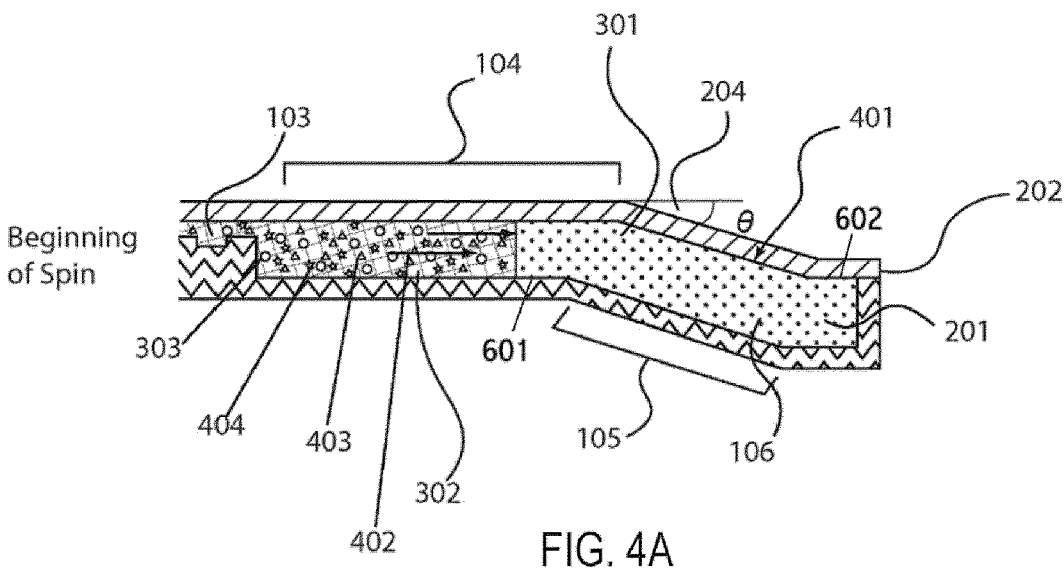
FIG. 4A
Fig. 4B
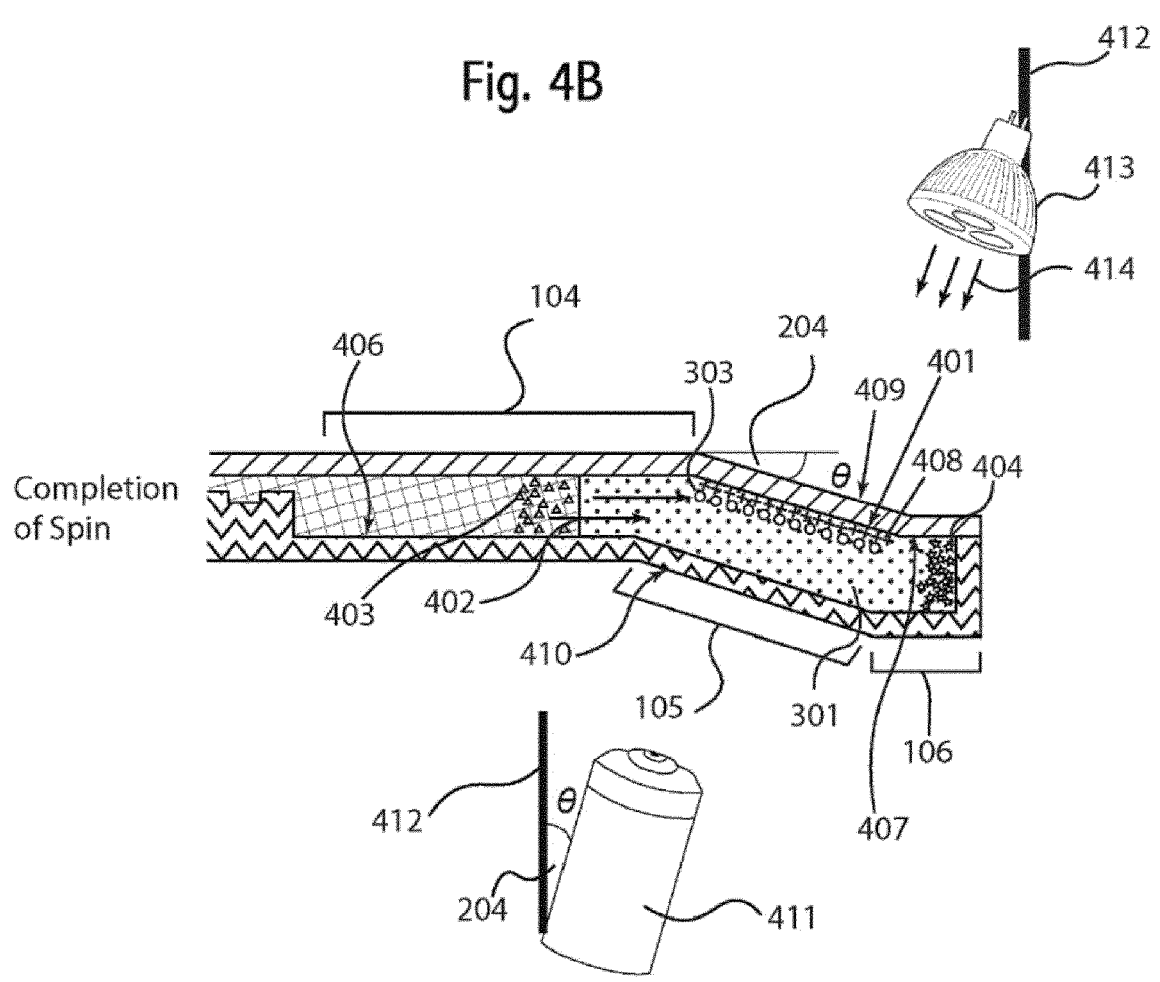

CROSS-SECTION B-B

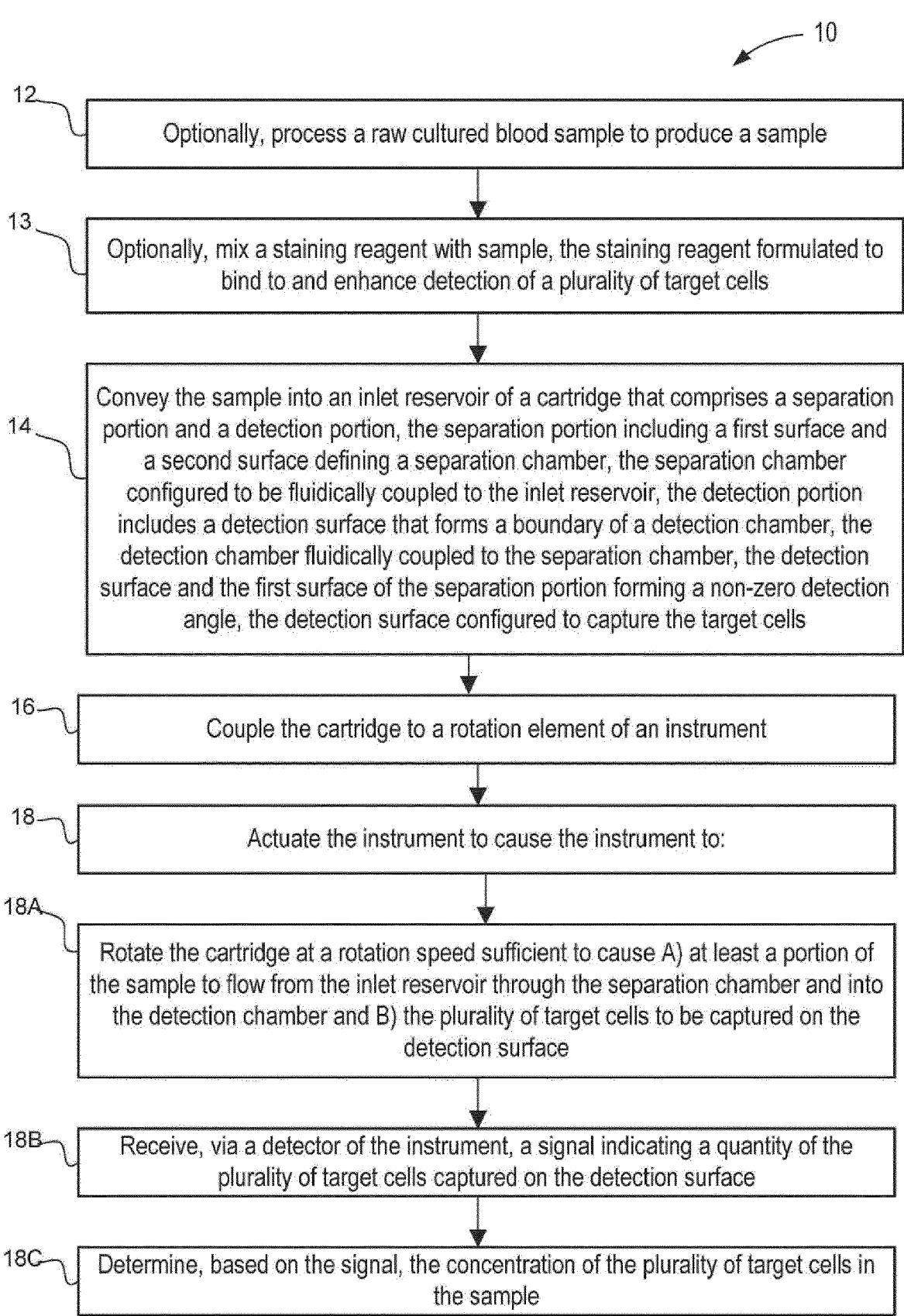

12 — Optionally, process a raw cultured blood sample to produce a sample

13 — Optionally, mix a staining reagent with sample, the staining reagent formulated to bind to and enhance detection of a plurality of target cells 14 — Convey the sample into an inlet reservoir of a cartridge that comprises a separation portion and a detection portion, the separation portion including a first surface and a second surface defining a separation chamber, the separation chamber configured to be fluidically coupled to the inlet reservoir, the detection portion includes a detection surface that forms a boundary of a detection chamber, the detection chamber fluidically coupled to the separation chamber, the detection surface and the first surface of the separation portion forming a non-zero detection angle, the detection surface configured to capture the target cells 16 — Couple the cartridge to a rotation element of an instrument 18 — Actuate the instrument to cause the instrument to:

18A — Rotate the cartridge at a rotation speed sufficient to cause A) at least a portion of the sample to flow from the inlet reservoir through the separation chamber and into the detection chamber and B) the plurality of target cells to be captured on the detection surface 18B — Receive, via a detector of the instrument, a signal indicating a quantity of the plurality of target cells captured on the detection surface 18C — Determine, based on the signal, the concentration of the plurality of target cells in the sample

FIG. 23

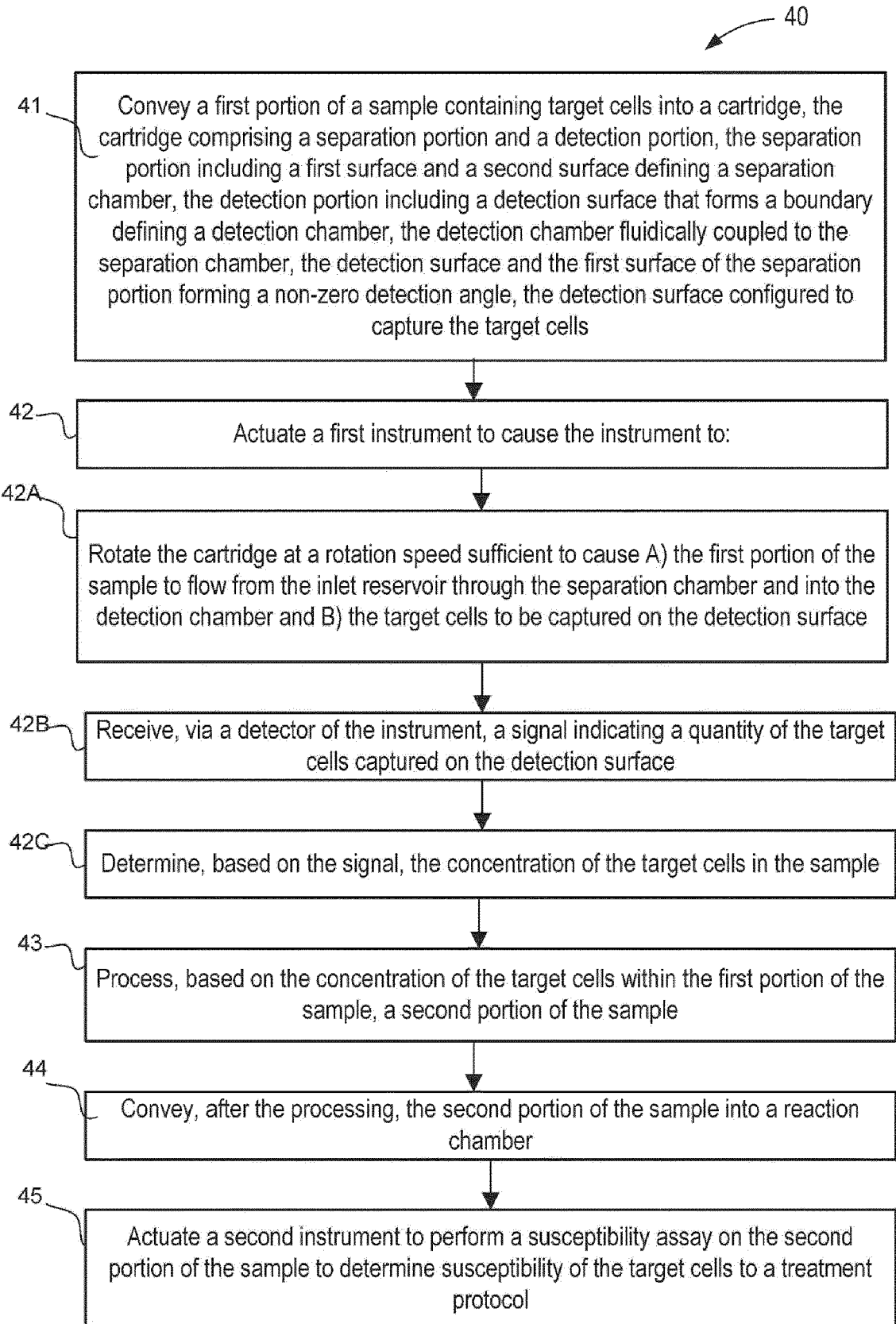

41   Convey a first portion of a sample containing target cells into a cartridge, the cartridge comprising a separation portion and a detection portion, the separation portion including a first surface and a second surface defining a separation chamber, the detection portion including a detection surface that forms a boundary defining a detection chamber, the detection chamber fluidically coupled to the separation chamber, the detection surface and the first surface of the separation portion forming a non-zero detection angle, the detection surface configured to capture the target cells 42   Actuate a first instrument to cause the instrument to:

42A   Rotate the cartridge at a rotation speed sufficient to cause A) the first portion of the sample to flow from the inlet reservoir through the separation chamber and into the detection chamber and B) the target cells to be captured on the detection surface 42B   Receive, via a detector of the instrument, a signal indicating a quantity of the target cells captured on the detection surface 42C   Determine, based on the signal, the concentration of the target cells in the sample 43   Process, based on the concentration of the target cells within the first portion of the sample, a second portion of the sample 44   Convey, after the processing, the second portion of the sample into a reaction chamber 45   Actuate a second instrument to perform a susceptibility assay on the second portion of the sample to determine susceptibility of the target cells to a treatment protocol

FIG. 25

Correlation Curve for Gram Negative Species

Correlation Curve for Gram Positive Species

Bilirubin interference

Lipid interference

DEVICES AND METHODS FOR DETERMINING PARTICLE CONCENTRATION IN A SAMPLE

CROSS-REFERENCE TO RELATED APPLICATIONS

This application is a U.S. national stage filing under 35 U.S.C. § 371 of International Application No. PCT/EP2019/061902, filed May 9, 2019, entitled "DEVICES AND METHODS FOR DETERMINING PARTICLE CONCENTRATION IN A SAMPLE," which claims benefit of priority to U.S. Provisional Application Ser. No. 62/669,357, entitled "Device and Method for Bacterial Assay," filed May 9, 2018 and U.S. Provisional Application Ser. No. 62/785,752, entitled "Devices and Method for Determining Particle Concentration in a Sample," filed Dec. 28, 2018, the disclosure of each of which is incorporated herein by reference in its entirety.

BACKGROUND

The embodiments described herein relate to devices and methods used to enumerate target cells in biological samples with known or suspected microbial content. Specifically, the embodiments described herein relate to cartridges and methods that include centrifugal plating of cells to a detection surface, separation of the cells based on size and/or density, and enumeration of particles based on a signal produced from the captured cells.

Blood infections, or sepsis, is a microbial infection in the blood that occurs in as many as 1-2% of hospitalizations. It is responsible for over 200,000 deaths per year in the U.S. Treatment pathways for sepsis rely largely on brute force, often beginning before a definitive diagnosis is made. Further information on the nature of the infection can give health care providers a greater ability to develop targeted treatment plans. Additionally, health-care practitioners or researchers may desire to analyze the nature of the infection through the use of known assays that may have variable efficacy depending on the concentration of cells in the sample. For example, in testing to determine whether a target bacterium is susceptible to treatment using known antibiotics (i.e., an antibiotic susceptibility test or AST) often requires that the bacteria in the sample be within a desired concentration range. If, for example, the concentration of bacteria in the sample is below the desired range, the result from the AST may incorrectly identify the bacteria as being susceptible. Conversely, if the concentration of bacteria in the sample is above the desired range, the result from the AST may incorrectly identify the bacteria as being resistant to the antibiotic. Thus, some known assays include first enumerating the bacteria within the sample. Current methods for the enumeration of bacteria include quantitative culture, most probable number analysis (MPN), direct hemocytometry, and direct photometric measurement of optical density. In sepsis samples, the primary method used to enumerate bacteria is quantitative culture, which involves plating serial dilutions of cells on culture agar, followed by an incubation period that takes 16 hours or more, depending on the strain identity or strain mixture identities. Cells are counted as colony-forming units (CFUs) after the incubation time through the formation of colonies on the plate. Actionable information is potentially acquired sooner using hemocytometry or optical density measurement, but the results from known methods can be obfuscated by the heterogeneous nature of blood samples. Hemocytometry is the direct counting of cells on a fixed-depth slide containing a grid or imaged through a microscope reticle. The technique may not work if other cells are present, which may hide, as in the case of red blood cells (RBCs) or white blood cells (WBCs) or have similar apparent sizes (platelets) in bright field imaging. Optical density measures the scattering of light, which generally correlates to cell density, however, this technique results in variable correlation curves with respect to sample matrices and strain identity and is also prone to error due to the presence of other non-analyte cells which may scatter light. Said another way, measurement of a target analyte population of particles is often frustrated by the presence of particulate contaminants. For example, measuring the concentration of bacteria suspended in whole blood using known devices and methods is problematic due to the presence of similarly sized particles, such as platelets and apoptotic fragments of blood cells. The particulate contamination of whole blood is worse in the case of measurements with a blood culture, where degradation of blood cells and coagulation of proteins produces a large quantity of bacteria-sized particles that can greatly exceed the concentration of actual bacteria. Other prior art methods of particle counting such as flow cytometry or absorbance spectroscopy also suffer from interference by contaminating particles.

Moreover, known methods, such as MPN, can involve serial dilutions of the sample and a statistical formula to determine the original quantity, and can take 24 to 48 hours to determine results.

Additionally, some known methods for enumerating bacteria can vary depending on the strain of the bacteria being analyzed (e.g., whether the bacteria are gram positive or gram negative). Strain identification in a blood laboratory is currently accomplished through advanced microbiological work, performed by a trained technician with access to selective media and a microscope. Gram staining is used to identify gram-identity of bacteria. Selective culture media (agar plates containing growth medium that contains only certain nutrients; some categories of bacteria can or cannot grow with certain missing or included nutrients) is often used to narrow down to specific bacteria families or genii. In advanced research settings, strain identification is accomplished through 16S-rRNA sequencing or through the use of MALD-TOF. Each of these techniques requires a minimum of 16 hours, where cell cultures plates must be grown to isolate a quantity of bacteria that can be stained an imaged or plated on multiple plates of growth media. Thus, a need exists for improved devices and methods for determining the concentration of target cells (e.g., bacteria) within a sample. In particular, a need exists for improved devices and methods for enumerating bacteria that can provide accurate results over a wide dynamic range of bacteria concentration.

SUMMARY OF THE INVENTION

Devices, systems, kits and methods for determining the concentration of target cells (e.g., bacteria) within a sample are described herein. In some embodiments, a system, a kit or a method for determining a concentration of target cells within a sample includes a cartridge configured to be removably coupled to a rotation element that rotates the cartridge about a rotation axis to capture the target cells within the sample. The cartridge includes an inlet portion defining an inlet reservoir configured to contain the sample, a separation portion, and a detection portion. The separation portion includes a first surface and a second surface defining a separation chamber. The separation portion can contain a density medium having a density greater than a density of a first portion of the sample and less than a density of a second portion of the sample. The second portion of the sample includes the target cells. The separation chamber is configured to be fluidically coupled to the inlet reservoir such that at least the second portion of the sample can pass from the inlet reservoir to the separation chamber when the cartridge is rotated. The detection portion includes a detection surface that forms a boundary of a detection chamber. The detection chamber is fluidically coupled to the separation chamber such that at least the target cells can pass through the density medium and into the detection chamber. The detection surface is nonparallel to at least one of the first surface or the second surface such that the target cells impinge on the surface when passing into the detection chamber. The detection surface is configured to capture the plurality of target cells.

A cartridge disclosed herein may comprise an inlet portion defining an inlet reservoir configured to contain the sample; a separation portion including a first surface and a second surface defining a separation chamber, the separation chamber being configured to be fluidically coupled to the inlet reservoir such that at least a portion of the sample can pass from the inlet reservoir to the separation chamber when the cartridge is rotated; and a detection portion defining a detection chamber, the detection portion including a detection surface that forms a boundary of the detection chamber, the detection chamber being fluidically coupled to the separation chamber such that at least the plurality of target cells can pass through the separation chamber and into the detection chamber, the detection surface and the first surface of the separation portion forming a non-zero detection angle, the detection surface being configured to capture the plurality of target cells.

In one aspect, a kit is provided comprising a cartridge configured to be removably coupled to an instrument configured to rotate the cartridge about a rotation axis and detect a plurality of target cells within a sample, the cartridge comprising an inlet portion defining an inlet reservoir configured to contain the sample; a separation portion including a first surface and a second surface defining a separation chamber, the separation chamber being configured to be fluidically coupled to the inlet reservoir such that at least a portion of the sample can pass from the inlet reservoir to the separation chamber when the cartridge is rotated; and a detection portion defining a detection chamber, the detection portion including a detection surface that forms a boundary of the detection chamber, the detection chamber being fluidically coupled to the separation chamber such that at least the plurality of target cells can pass through the separation chamber and into the detection chamber, the detection surface and the first surface of the separation portion forming a non-zero detection angle, the detection surface being configured to capture the plurality of target cells; a density medium having a density of between 1.01 g/cm$^3$ and 1.13 g/cm$^3$; and a staining reagent formulated to bind to and enhance detection of the plurality of target cells. Such a kit may be used for detecting a concentration of a plurality of target cells within a sample. In some embodiments, the kit further comprises a dilution reagent. In some embodiments, the detection angle between the detection surface and the first surface of the separation portion is between about 1 degree and about 8 degrees; and the detection surface includes a surface modification to enhance adhesion of the plurality of target cells. In some embodiments, the first surface of the separation portion and the detection surface are monolithically constructed; and the detection angle is about 2 degrees. In some embodiments, the detection surface includes a chemical modification to enhance adhesion of the plurality of target cells. In certain embodiments, the surface modification includes a coating comprising a charged polymer. In some embodiments, the density medium is stored within a prefilled, sealed container that is separate from the cartridge and has a volume of less than fifty percent of a volume of the cartridge. In some embodiments, the density medium comprises any of an antifoaming agent, a wetting agent, a dispersant, or an emulsifier. In some embodiments, the dilution reagent is stored with a prefilled container that is separate from the cartridge, the dilution reagent comprising any of an antifoaming agent, a wetting agent, a dispersant, or an emulsifier.

In another aspect, a method of detecting a concentration of a plurality of target cells within a sample is provided. The method comprises conveying the sample into an inlet reservoir of a cartridge, the cartridge further comprising a separation portion and a detection portion, the separation portion including a first surface and a second surface defining a separation chamber, the separation chamber being configured to be fluidically coupled to the inlet reservoir, the detection portion defining a detection chamber and including a detection surface that forms a boundary of the detection chamber, the detection chamber being fluidically coupled to the separation chamber, the detection surface and the first surface of the separation portion forming a non-zero detection angle, the detection surface being configured to capture the plurality of target cells; coupling the cartridge to a rotation element of an instrument; and actuating the instrument to cause the instrument to rotate the cartridge at a rotation speed sufficient to cause a) at least a portion of the sample to be conveyed from the inlet reservoir through the separation chamber and into the detection chamber; and b) the plurality of target cells to be captured on the detection surface; receive, via a detector of the instrument, a signal indicating a quantity of the plurality of target cells captured on the detection surface; and determine, based on the signal, the concentration of the plurality of target cells in the sample within a lower limit of 10^3 colony forming units (CFU) per milliliter (mL) and an upper limit of 10^9 CFU per mL.

In another aspect, a method of detecting a concentration of a plurality of target cells within a sample is provided including conveying the sample into an inlet reservoir of a cartridge. The cartridge includes a separation portion and a detection portion. The separation portion includes a first surface and a second surface defining a separation chamber that can be fluidically coupled to the inlet reservoir. The detection portion includes a detection surface that forms a boundary of a detection chamber. The detection chamber is fluidically coupled to the separation chamber, and the detection surface and the first surface of the separation portion form a non-zero detection angle. The detection surface is configured to capture the plurality of target cells. The cartridge is coupled to a rotation element of an instrument. The instrument is then actuated to cause the instrument to: (1) rotate the cartridge at a rotation speed sufficient to cause at least a portion of the sample to be conveyed from the inlet reservoir through the separation chamber and pass into the detection chamber, and the target cells to be captured on the detection surface; (2) receive, via a detector of the instrument, a signal indicating a quantity of the target cells captured on the detection surface; and (3) determine, based on the signal, the concentration of the plurality of target cells in the sample.

In another aspect, a method of detecting a concentration of a plurality of target cells within a sample is provided. The method comprises transferring a density medium from a container into a cartridge, the cartridge comprising an inlet portion, a separation portion and a detection portion, the inlet portion defining an inlet reservoir, the separation portion including a first surface and a second surface defining a separation chamber, the separation chamber being fluidically coupled to the inlet reservoir, the detection portion including a detection surface that forms a boundary of a detection chamber, the detection chamber being fluidically coupled to the separation chamber, the detection surface and the first surface of the separation portion forming a non-zero detection angle, the detection surface configured to capture the plurality of target cells; and the transferring being performed such that the density medium is contained within the separation chamber, the density medium having a density greater than a density of a first portion of the sample and less than a density of a second portion of the sample, the second portion of the sample containing the plurality of target cells; conveying the sample into the inlet reservoir; rotating the cartridge within an instrument at a rotation speed and for a rotation duration sufficient to cause a) the second portion of the sample to pass from the inlet reservoir through the density medium in the separation chamber and into the detection chamber and b) the plurality of target cells to be captured on the detection surface; receiving, via a detector of the instrument, a signal indicating a quantity of the plurality of target cells captured on the detection surface; and determining, based on the signal, the concentration of the plurality of target cells in the sample.

In another aspect, a method of determining susceptibility of a plurality of target cells to a treatment protocol is provided. The method comprises conveying a first portion of a sample containing the plurality of target cells into a cartridge, the cartridge comprising a separation portion and a detection portion, the separation portion including a first surface and a second surface defining a separation chamber, the detection portion including a detection surface that forms a boundary defining a detection chamber, the detection chamber being fluidically coupled to the separation chamber, the detection surface and the first surface of the separation portion forming a non-zero detection angle, the detection surface configured to capture the plurality of target cells; actuating a first instrument to cause the first instrument to rotate the cartridge at a rotation speed sufficient to cause a) the first portion of the sample to be conveyed through the separation chamber and into the detection chamber and b) the plurality of target cells to be captured on the detection surface; receive, via a detector of the first instrument, a signal indicating a quantity of the plurality of target cells captured on the detection surface; and determine, based on the signal, the concentration of the plurality of target cells in the first portion of the sample; processing, based on the concentration of the plurality of target cells within the first portion of the sample, a second portion of the sample; conveying, after the processing, the second portion of the sample into a reaction chamber; and actuating a second instrument to perform a susceptibility assay on the second portion of the sample to determine susceptibility of the plurality of target cells to the treatment protocol. In some embodiments, the method processing includes diluting the second portion of the sample until a concentration of the plurality of target cells within the second portion of the sample is within a predetermined range.

In some embodiments of the methods described above and herein, the concentration of the plurality of target cells within a lower limit of $10^3$ colony forming units (CFU) per milliliter (mL) and an upper limit of $10^9$ CFU per mL. This concentration may be determined by the instrument. In some embodiments, the lower limit is about $10^5$ CFU per mL. In some embodiments, the portion of the sample that is conveyed from the inlet reservoir through the separation chamber and into the detection chamber is a second portion; and the cartridge contains a density medium within the separation chamber, the density medium having a density greater than a density of a first portion of the sample and less than a density of the second portion of the sample, the first portion of the sample being maintained within the separation chamber after the cartridge is rotated. In some embodiments, the portion of the sample that is conveyed from the inlet reservoir through the separation chamber and into the detection chamber is a second portion and the method further comprises conveying a density medium into the cartridge before the sample is conveyed into the inlet reservoir, the density medium having a density greater than a density of a first portion of the sample and less than a density of the second portion of the sample, the first portion of the sample being maintained within the separation chamber after the cartridge is rotated. In some embodiments, the method further comprises conveying a dilution reagent into the cartridge, at least one of the dilution reagent or the density medium comprising any of an antifoaming agent, a wetting agent, a dispersant, or an emulsifier. In some embodiments, conveying the dilution reagent includes mixing the dilution reagent with the sample and conveying the dilution reagent and the sample into the inlet reservoir of the cartridge in the same operation. In some embodiments, a dilution reagent is conveyed into the cartridge along with the density medium, at least one of the dilution reagent or the density medium comprises any of an antifoaming agent, a wetting agent, a dispersant, or an emulsifier. In some embodiments, the density medium has a density of between 1.05 g/cm$^3$ and 1.09 g/cm$^3$. In some embodiments, at least one of the dilution reagent or the density medium comprises a poloxamer. In some embodiments, the sample is a bodily fluid. In certain embodiments, the sample is any one of a blood sample or a urine sample. In particular embodiments, the blood sample is a cultured blood sample; and the plurality of target cells is a plurality of bacteria cells. In certain embodiments, the plurality of bacteria cells includes any of Enterobacteriaceae, *Pseudomonas* spp, *Acinetobacter* spp, *Staphylococcus* spp, *Streptococcus* spp, or *Enterococcus* spp. In some embodiments, the method further comprises processing, before the conveying the cultured blood sample into the inlet reservoir of the cartridge, a raw cultured blood sample to produce the cultured blood sample. In some embodiments, the method further comprises mixing a staining reagent with sample, the staining reagent formulated to bind to and enhance detection of the plurality of target cells. In certain embodiments, the staining reagent is a fluorescent staining reagent formulated to stain the plurality of target cells. In some embodiments, the instrument rotates the cartridge at the rotation speed of between about 3000 rpm and 15,000 rpm for a time period of at least 1 minute. In certain embodiments, the rotation speed is between about 6000 rpm and 7000 rpm. In some embodiments, the container and the cartridge are packaged together within a kit.

In another aspect, an apparatus is provided comprising a cartridge configured to be removably coupled to a rotation element configured to rotate the cartridge about a rotation axis to capture a plurality of target cells within a sample, the cartridge comprising an inlet portion defining an inlet reservoir configured to contain the sample; a separation portion including a first surface and a second surface defining a separation chamber, the separation portion configured to contain a density medium having a density greater than a density of a first portion of the sample and less than a density of a second portion of the sample, the second portion including the plurality of target cells, the separation chamber configured to be fluidically coupled to the inlet reservoir such that at least the second portion of the sample can pass from the inlet reservoir to the separation chamber when the cartridge is rotated; and a detection portion including a detection surface that forms a boundary of a detection chamber, the detection chamber fluidically coupled to the separation chamber such that at least the plurality of target cells can pass through the density medium and into the detection chamber, the detection surface being nonparallel to at least one of the first surface or the second surface such that the plurality of target cells impinge on the detection surface when passing into the detection chamber, the detection surface configured to capture the plurality of target cells; and a dilution reagent, wherein at least one of the dilution reagent or the density medium comprise any of an antifoaming agent, a wetting agent, a dispersant, or an emulsifier.

In another aspect, an apparatus is provided comprising a cartridge configured to be removably coupled to a rotation element configured to rotate the cartridge about a rotation axis to capture a plurality of target cells within a sample, the cartridge comprising an inlet portion defining an inlet reservoir configured to contain the sample; a separation portion including a first surface and a second surface defining a separation chamber, the separation chamber configured to be fluidically coupled to the inlet reservoir such that at least a portion of the sample can be conveyed from the inlet reservoir to the separation chamber when the cartridge is rotated; and a detection portion defining a detection chamber, the detection portion including a detection surface that forms a boundary of the detection chamber, the detection chamber fluidically coupled to the separation chamber such that at least the plurality of target cells can be conveyed through the separation chamber and into the detection chamber, the detection surface and the first surface of the separation portion forming a non-zero detection angle, the detection surface including a surface modification to enhance adhesion of the plurality of target cells, a ratio of a volume of the separation chamber and a volume of the detection chamber being at least about 2.0.

In yet another aspect, an apparatus is provided comprising a cartridge configured to be removably coupled to a rotation element configured to rotate the cartridge about a rotation axis to capture a plurality of target cells within a sample, the cartridge comprising an inlet portion defining an inlet reservoir configured to contain the sample; a separation portion including a first surface and a second surface defining a separation chamber, the separation portion configured to contain a density medium having a density greater than a density of a first portion of the sample and less than a density of a second portion of the sample, the second portion including the plurality of target cells, the separation chamber configured to be fluidically coupled to the inlet reservoir such that at least the second portion of the sample can pass from the inlet reservoir to the separation chamber when the cartridge is rotated; and a detection portion includes a detection surface that forms a boundary of a detection chamber, the detection chamber fluidically coupled to the separation chamber such that at least the plurality of target cells can pass through the density medium and into the detection chamber, the detection surface being nonparallel to at least one of the first surface or the second surface such that the plurality of target cells impinge on the detection surface when passing into the detection chamber, the detection surface configured to capture the plurality of target cells.

In another aspect, an apparatus is provided comprising a cartridge configured to be removably coupled to a rotation element configured to rotate the cartridge about a rotation axis to capture a plurality of target cells within a sample, the cartridge comprising an inlet portion defining an inlet reservoir configured to contain the sample; a separation portion including a first surface and a second surface defining a separation chamber, the separation chamber configured to be fluidically coupled to the inlet reservoir such that at least a portion of the sample can be conveyed from the inlet reservoir to the separation chamber when the cartridge is rotated; and a detection portion defining a detection chamber, the detection portion including a detection surface that forms a boundary of the detection chamber, the detection chamber fluidically coupled to the separation chamber such that at least the plurality of target cells can be conveyed through the separation chamber and into the detection chamber, the detection surface and the first surface of the separation portion forming a non-zero detection angle, the detection surface configured to capture the plurality of target cells, a ratio of a volume of the separation chamber and a volume of the detection chamber being at least about 2.0.

In some embodiments of the apparatuses described above and herein, the first surface of the separation portion and the detection surface form a detection angle of between about 1 degree and about 8 degrees. In certain embodiments, the detection angle is about 2 degrees. In some embodiments, a transition region between the first surface of the separation portion and the detection surface defines a maximum radius of curvature of less than 0.1 mm. In some embodiments, a distance between the first surface of the separation portion and the second surface of the separation portion define a thickness of the separation chamber, the thickness being less than about 0.6 mm. In certain embodiments, the thickness of the separation chamber is less than about 0.3 mm. In some embodiments, the first surface of the separation portion and the detection surface are monolithically constructed. In some embodiments, the cartridge defines a radial axis that intersects the rotation axis; the first surface of the separation portion and the detection surface are monolithically constructed; and the detection angle is along the radial axis and within a cross-sectional plane defined by the radial axis and the rotation axis. In some embodiments, the inlet portion defines an opening through which the sample can be conveyed into the inlet reservoir; and the detection surface is angled in a downward direction with respect to the opening. In some embodiments, a ratio of a volume of the separation chamber and a volume of the detection chamber is at least about 2.0. In some embodiments, the ratio of the volume of the separation chamber and the volume of the detection chamber is between about 2.0 and 5.0. In certain embodiments, the ratio of the volume of the separation chamber and the volume of the detection chamber is at least about 2.5. In some embodiments, the apparatus further comprises the density medium, the density medium having a density of between $1.01$ g/cm$^3$ and $1.13$ g/cm$^3$. In certain embodiments, the density medium has a density of between $1.05$ g/cm$^3$ and $1.09$ g/cm$^3$. In some embodiments, the separation portion defines a density medium reservoir within which the density medium is contained. In some embodiments, at least one of the dilution reagent or the density medium comprises a poloxamer. In certain embodiments, the poloxamer contains poly(ethylene oxide) (PEO) and poly(propylene oxide) (PPO). In some embodiments, the apparatus further comprises a staining reagent, the staining reagent formulated to bind to and enhance detection of the plurality of target cells. In some embodiments, the detection surface includes a surface modification to enhance adhesion of the plurality of target cells. In certain embodiments, the surface modification includes a coating comprising a charged polymer. In particular embodiments, the coating is poly-L-lysine that is charged with ($-NH_3^+$). In some embodiments, the cartridge is configured to concentrate the plurality of target cells captured on the detection surface.

In some embodiments, the cartridge of the apparatuses described above is a centrifuge cartridge that includes a density medium and/or one or more non-plastic components within the cartridge. In some embodiments, the cartridge can be used to separate target particles (e.g., cells) originally contained in a biological sample from contaminants of different density and size. This is accomplished by centrifuging particles out of the biological sample through the density medium in the cartridge. The density medium has a higher density than the biological sample and lower density than the target particles. In some embodiments, the density medium can be contained in the imaging cartridge prior to addition of the biological sample and will occupy the area of an angled imaging surface of the cartridge. In some embodiments, the target particles are captured by the angled imaging surface while contaminant particles are either retained in the biological sample (for small or low-density contaminants) or centrifuged past the density medium and away from the angled imaging surface (for larger and high-density contaminants). The number of target particles per a given imaging area will correlate with the original concentration of target particles suspended in the biological sample. In some embodiments, the specificity of imaging target particles (as opposed to contaminants) can be improved by adding dyes that specifically label the target particle.

The cartridge or the methods of determining concentration of target cells can be used as a part of a biological assay. For example, a method of determining susceptibility of target cells to a treatment protocol can include conveying a first portion of a sample containing the target cells into a cartridge. A first instrument is then actuated to cause the first instrument to rotate the cartridge at a rotation speed sufficient to cause A) the first portion of the sample to be conveyed through a separation chamber and into a detection chamber and B) the target cells to be captured on a detection surface within the cartridge. The first instrument then receives, via a detector, a signal indicating a quantity of the target cells captured on the detection surface and determines, based on the signal, the concentration of the target cells in the first portion of the sample. A second portion of the sample is then processed based on the concentration of the plurality of target cells within the first portion of the sample. For example, under particular circumstances the second portion of the sample can be diluted. The method may further include conveying, after the second portion of the sample is processed, the second portion of the sample into a reaction chamber. A second instrument is then actuated to perform a susceptibility assay on the second portion of the sample to determine susceptibility of the target cells to the treatment protocol. Also provided is a system for determining a concentration of target cells within a sample includes a centrifuge cartridge, a motor, a connection to spin the cartridge via the motor, and a controller for controlling the centrifugal operation. Herein, the system may include imaging hardware for imaging in or through the cartridge, including any software or firmware therein.

Also provided is a method of manufacturing a cartridge including conveying a density medium into the cartridge.

10

BRIEF DESCRIPTION OF THE DRAWINGS

FIGS. 4A and 4B show a cross-sectional view of a portion of a cartridge according to an embodiment containing a sample and a density medium at the beginning of a rotation cycle (FIG. 4A) and after being rotated (FIG. 4B).

FIG. 23 is a flow chart of a method of detecting a concentration of target cells within a sample, according to an embodiment.

FIG. 25 is a flow chart of a method of determining the susceptibility of target cells to a treatment protocol, according to an embodiment.

DETAILED DESCRIPTION OF THE INVENTION

Figure 1:
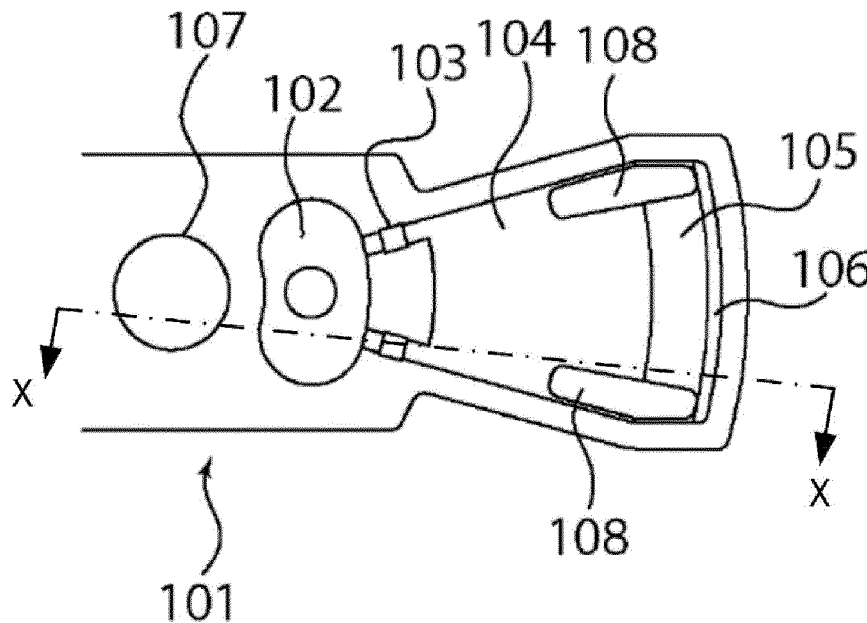
FIG. 1 is a top view of a portion of a cartridge, according to an embodiment.

Devices and methods for determining the concentration of target cells (e.g., bacteria) within a sample are described herein. In some embodiments, the devices described herein are used in rapid automated or semi-automated quantification of particles such as bacteria or cells in biological samples such as blood or urine. The embodiments described herein can provide accurate results over a wide dynamic range of cell concentration. Specifically, in some embodiments, a device and/or a method can determine cell concentration with a lower limit of detection of 1000 (i.e., 10^3) colony forming units (CFU) per milliliter (mL). In some embodiments, a device and/or a method can determine cell concentration for a sample within a range of 10^3 CFU/mL and 10^9 CFU/mL. Moreover, the embodiments described herein can produce accurate particle or cell concentration results in samples having a wide range of contaminants. Thus, the embodiments described herein are suitable for use with a variety of samples, including a cultured blood sample. In some embodiments, a system or method for determining a concentration of target cells within a sample includes a cartridge configured to be removably coupled to a rotation element that rotates the cartridge about a rotation axis to capture the target cells within the sample. The cartridge includes an inlet portion defining an inlet reservoir configured to contain the sample, a separation portion, and a detection portion. The separation portion includes a first surface and a second surface defining a separation chamber. The separation portion can contain a density medium having a density greater than a density of a first portion of the sample and less than a density of a second portion of the sample. The second portion of the sample includes the target cells. The separation chamber is configured to be fluidically coupled to the inlet reservoir such that at least the second portion of the sample can pass from the inlet reservoir to the separation chamber when the cartridge is rotated. The detection portion includes a detection surface that forms a boundary of a detection chamber. The detection chamber is fluidically coupled to the separation chamber such that at least the target cells can pass through the density medium during rotation and into the detection chamber. The detection surface is nonparallel to at least one of the first surface or the second surface such that the target cells impinge on the surface when passing through the density medium into the detection chamber. The detection surface is configured to capture the plurality of target cells.

In some embodiment, a method includes centrifuging a sample within the cartridge to separate target particles (e.g., cells) originally contained in the sample from contaminants of different density and size. In some embodiments, the sample is centrifuged through a density medium or density gradient within the cartridge that has a density higher than that of the sample but less than that of the individual target particles. The density medium can be contained in a cartridge prior to addition of the sample and can occupy the area of the angled detection (or imaging) surface. In this manner, the target particles can be captured by an angled detection surface while contaminant particles are either retained in the sample in the separation chamber (for small or low-density contaminants) or centrifuged past the density medium (for larger and high-density contaminants). The number of target particles within the known detection (or imaging) area can be correlated to the original concentration of target particles suspended in the sample.

In some embodiments, a cartridge or kit includes a density medium, which serves to separate target particles from contaminants. The density medium may be formulated from aqueous solutions or suspensions that have a mass density between 1.01 g/cm$^3$ and 1.13 g/cm$^3$. In some embodiments, for example when the target particles are bacteria, the mass density of the density medium is between 1.03 g/cm$^3$ and 1.09 g/cm$^3$. In other embodiments, the mass density of the density medium is between 1.06 g/cm$^3$ and 1.08 g/cm$^3$.

In some embodiments, the cartridge includes a defines a density medium reservoir within which the density medium is contained before and during use. The density medium reservoir can ensure that the desired amount of the density medium is within the cartridge to ensure the desired performance. During centrifugation, the sample will form a distinct layer in contact with and rotationally inward from the density medium. During use, mixing of the sample and density medium is limited during the measurement technique to limit the likelihood of contaminants being introduced to the detection (or imaging) surface.

In some embodiments, a detection (or imaging) surface of a cartridge can be configured to capture the plurality of target cells. For example, in some embodiments, a detection surface can include a surface treatment or modification to enhance the adhesion of the target particles (or cells) to the detection surface. In particular, such a surface modification can enhance the particle capture by a detection surface having a shallow angle (with respect to a wall of a separation chamber). Such surface modifications can prevent the target particles from traveling along the along the surface to form a pellet at the distal end of the cartridge. In some embodiments, the adhesive force of the detection surface can be greater than the effective centrifugal force caused by rotation of the cartridge. Thus, the shallower the detection surface angle, the greater the adhesive force must be to prevent migration of the target particles for a given spin rate.

In some embodiments, the detection surface can include a coating having a charged polymer. For example, in some embodiments, the detection surface can include poly-L-lysine having a positive electrical charge.

In some embodiments, a cartridge can be configured to limit undesirable mixing of the sample (including the target particles) and the density medium. Specifically, in some embodiments, the depth of certain chambers (or channels) can be selected to minimize mixing. For example, in some embodiments, a cartridge can include a separation chamber having a depth (or thickness) of less than 0.60 mm, less than 0.40 mm, or less than 0.30 mm. In other embodiments, the separation chamber can have a thickness less than 0.3 mm, or less than 0.2 mm or less than 0.1 mm, enabling time for imaging. Layers within the sample and fluids contained in the cartridge can also be stabilized by structuring the cartridge such that the angled detection (or imaging) channel and detection (or imaging) surface are angled downward. This downward angle causes the density medium to naturally remain in the distal region of the cartridge, including the angled imaging channel, under natural gravity.

In some embodiments, an apparatus or kit includes a cartridge configured to be removably coupled to a rotation element that rotates the cartridge about a rotation axis to capture target cells within a sample. The cartridge includes an inlet portion defining an inlet reservoir that contains the sample, a separation portion, and a detection portion. The separation portion includes a first surface and a second surface defining a separation chamber (or channel). The separation chamber can be fluidically coupled to the inlet reservoir such that at least a portion of the sample can be conveyed from the inlet reservoir to the separation chamber when the cartridge is rotated. The detection portion includes a detection surface that forms a boundary of a detection chamber. The detection chamber is fluidically coupled to the separation chamber such that at least the target cells can pass through the separation chamber and into the detection chamber. The detection surface and the first surface of the separation portion form a non-zero detection angle. The detection surface is configured to capture the target cells, and can include a coating, a positively charged treatment, or the like. A ratio of a volume of the separation chamber and a volume of the detection chamber is at least about 2.0. By maintaining the volume ratio within a desired range, the ratio of the sample to a density medium within the cartridge can be maintained within a desired range to ensure that the detection (or imaging) volume is appropriately filled with the density medium.

In some embodiments, the ratio of the volume of the separation chamber and the volume of the detection chamber is between about 2.0 and 5.0. In some embodiments, the ratio of the volume of the separation chamber and the volume of the detection chamber is about 2.5. In some embodiments, the non-zero detection angle can influence the effectiveness of the detection surface in capturing the target cells. In some embodiments, the detection angle between the detection surface and the first surface of the separation portion is between about 1 degree and about 8 degrees. In some embodiments, the first surface of the separation portion and the detection surface are monolithically constructed, and the detection angle is about 2 degrees.

In some embodiments, the methods, cartridges, and/or kits described herein can include and/or employ a staining reagent formulated to bind to and enhance detection of the target cells. The use of a staining reagent can improve the specificity of detecting (e.g., imaging) target particles in samples containing contaminants. In some embodiments, the staining reagent can include DNA dyes such as Syto, DAPI, or Hoechst 33258, which are used to label DNA within target cells (e.g., bacterial particles) while leaving platelets (which do not contain DNA) unstained. In some embodiments, unbound dye (a small molecule) will be retained in the biological sample and will not migrate onto the detection (e.g., imaging) surface. In addition to differences in labeling the target particles can also be identified against residual contaminants by size or shape. In some embodiments, a kit for performing methods of determining the concentration of target cells in a sample includes a cartridge, a density medium, and a staining reagent. The cartridge can be removably coupled to an instrument configured to rotate the cartridge about a rotation axis and detect the target cells within the sample. The cartridge includes an inlet portion defining an inlet reservoir configured to contain the sample, a separation portion, and a detection portion. The separation portion includes a first surface and a second surface defining a separation chamber. The separation chamber can be fluidically coupled to the inlet reservoir such that at least a portion of the sample can pass from the inlet reservoir to the separation chamber when the cartridge is rotated. The detection portion includes a detection surface that forms a boundary of a detection chamber. The detection chamber is fluidically coupled to the separation chamber such that at least the target cells can pass through the separation chamber and into the detection chamber. The detection (e.g., imaging) surface and the first surface of the separation portion forming a non-zero detection angle. The detection surface is configured to capture the target cells. The density medium can be either pre-loaded into the cartridge or included within a separate container for use with any of the methods described herein. The density medium has a density of between 1.01 g/cm$^3$ and 1.13 g/cm$^3$. The staining reagent is formulated to bind to and enhance detection of the plurality of target cells. In some embodiments, the kit further includes a dilution reagent that is mixed with the sample prior and/or during use.

In some embodiments, a method of determining the concentration of target cells in a sample can include imaging the detection surface on which the target cells are captured. In some embodiments, a method of detecting a concentration of a plurality of target cells within a sample includes conveying the sample into an inlet reservoir of a cartridge. The cartridge includes a separation portion and a detection portion. The separation portion includes a first surface and a second surface defining a separation chamber that can be fluidically coupled to the inlet reservoir. The detection portion includes a detection surface that forms a boundary of a detection chamber. The detection chamber is fluidically coupled to the separation chamber, and the detection surface and the first surface of the separation portion form a non-zero detection angle.

The detection surface is configured to capture the plurality of target cells. The cartridge is coupled to a rotation element of an instrument. The instrument is then actuated to cause the instrument to: (1) rotate the cartridge at a rotation speed sufficient to cause at least a portion of the sample to be conveyed from the inlet reservoir into the separation chamber, and the target cells to be conveyed into the detection chamber and captured on the detection surface; (2) receive, via a detector of the instrument, a signal indicating a quantity of the target cells captured on the detection surface; and (3) determine, based on the signal, the concentration of the target cells in the sample.

In some embodiments, the instrument determines the concentration of the target cells within a lower limit of 10^3 CFU/mL and an upper limit 10^9 CFU/mL.

In some embodiments, the portion of the sample that is conveyed from the inlet reservoir through the separation chamber and into the detection chamber is a second portion, and the method can further include conveying a density medium into the cartridge before the sample is conveyed into the inlet reservoir. The density medium has a density greater than a density of a first portion of the sample and less than a density of the second portion of the sample. The first portion of the sample is maintained within the separation chamber after the cartridge is rotated. The density medium can be any of the density medium compositions and can have any of the properties (e.g., density value) described herein. For example, in some embodiments, the density medium can be included with a kit that is packaged along with the cartridge. In such embodiments, a predetermined amount of the density medium (e.g., an amount sufficient to fill the cartridge to the desired level without overfilling) can be packaged in a container separate from the cartridge. In some embodiments, a volume of the density medium can be less than fifty percent of the volume of the cartridge. By packaging the density medium and the cartridge separately, the kit may have an extended shelf life. Additionally, if certain assays require one density medium and other assays require a second, different density medium, separately packaging the density medium and the cartridge can allow for the same cartridge to be used in different kits (each with different reagents, density media, or the like).

In other embodiments, however, the method can be performed with a cartridge that is pre-filled with the density medium.

In some embodiments, the method further includes conveying a dilution reagent into the cartridge before the sample is conveyed into the inlet reservoir. In some embodiments, the dilution reagent can be included as a part of the density medium that is conveyed into the cartridge. In other embodiments, the dilution reagent can be added to the cartridge in a separate operation from adding the density medium. At least one of the dilution reagent or the density medium comprising any of an antifoaming agent, a wetting agent, a dispersant, or an emulsifier. As used herein a dispersant can be any substance that improves the separation of particles (e.g., to prevent agglomeration or clumping). A dispersant can be or include a surfactant. For example, in some embodiments, the dilution reagent (or the density media) can include a poloxamer, which can function as a surfactant to improve the separation of the particles (e.g., the target cells, waste particle or the like). In some embodiments, the dilution reagent can be included with a kit that is packaged along with the cartridge. In such embodiments, a predetermined amount of the dilution reagent (e.g., an amount sufficient to fill the cartridge to the desired level without overfilling) can be packaged in a container separate from the cartridge. By packaging the dilution reagent and the cartridge separately, the kit may have an extended shelf life. Additionally, if certain assays require one dilution reagent and other assays require a second, different dilution reagent, separately packaging the dilution reagent and the cartridge can allow for the same cartridge to be used in different kits (each with different reagents, density media, or the like).

In some embodiments, the dilution reagent can be mixed with the sample and then the mixture of the sample and the dilution reagent can be conveyed into the inlet reservoir of the cartridge. Similarly stated, in some embodiments, the dilution reagent and the sample can be conveyed into the inlet reservoir in the same operation.

In other embodiments, however, the method can be performed with a cartridge that is pre-filled with the dilution reagent.

In some embodiments, the signal can be an optical signal that is received by an optical detector of an imaging subsystem of the instrument. Such imaging techniques can include, for example, identifying and counting particles of interest based on light produced from the detection portion of the cartridge. Such imaging techniques can include brightfield, darkfield, and/or can be enhanced by any of the staining reagents described herein.

In some embodiments, all or a portion of the measurement techniques may be done via automated steps (i.e., steps that do not require further human intervention after actuating the instrument). In some embodiments a system for determining particle concentration can automatically identify target particles (e.g., to distinguish target cells from contaminants) by identification algorithms and compute the original concentration of target particles in the biological sample.

In some embodiments, a method of detecting a concentration of target cells within a sample includes rotating a cartridge within an instrument. The cartridge includes an inlet portion, a separation portion and a detection portion. The inlet portion defines an inlet reservoir containing the sample before the rotating. The separation portion includes a first surface and a second surface defining a separation chamber containing a density medium having a density greater than a density of a first portion of the sample and less than a density of a second portion of the sample. The second portion of the sample contains the target cells. The separation chamber is fluidically coupled to the inlet reservoir during the rotating. The detection portion includes a detection surface that forms a boundary of a detection chamber that is fluidically coupled to the separation chamber. The detection surface and the first surface of the separation portion form a non-zero detection angle, and the detection surface is configured to capture the plurality of target cells. The rotating is performed at a rotation speed and for a rotation duration sufficient to cause A) the second portion of the sample to pass from the inlet reservoir through the density medium in the separation chamber and then pass into the detection chamber and B) the target cells to be captured on the detection surface. The method further includes receiving, via a detector of the instrument, a signal indicating a quantity of the target cells captured on the detection surface. The concentration of the target cells in the sample is then determined, based on the signal.

In some embodiments, a method of detecting a concentration of target cells within a sample includes transferring a density medium from a container into a cartridge. The cartridge includes an inlet portion, a separation portion and a detection portion. The inlet portion defines an inlet reservoir. The separation portion includes a first surface and a second surface defining a separation chamber. The density medium has a density greater than a density of a first portion of the sample and less than a density of a second portion of the sample, and is conveyed into the separation chamber. The second portion of the sample contains the target cells. The separation chamber is fluidically coupled to the inlet reservoir. The detection portion includes a detection surface that forms a boundary of a detection chamber that is fluidically coupled to the separation chamber. The detection surface and the first surface of the separation portion form a non-zero detection angle, and the detection surface is configured to capture the plurality of target cells. The sample is conveyed into the inlet reservoir. The cartridge is then rotated within an instrument at a rotation speed and for a rotation duration sufficient to cause A) the second portion of the sample to pass from the inlet reservoir through the density medium in the separation chamber and then pass into the detection chamber and B) the target cells to be captured on the detection surface. The method further includes receiving, via a detector of the instrument, a signal indicating a quantity of the target cells captured on the detection surface. The concentration of the target cells in the sample is then determined, based on the signal.

In some embodiments, the container (containing the density medium) and the cartridge are packaged together within a kit.

In some embodiments, the method further includes conveying a dilution reagent into the cartridge. At least one of the dilution reagent or the density medium comprise any of an anti-foaming agent, a wetting agent, a dispersant, or an emulsifier. In some embodiments, at least one of the dilution reagent or the density medium comprises a poloxamer. In some embodiments, the conveying the dilution reagent includes mixing the dilution reagent with the sample and conveying the dilution reagent and the sample into the inlet reservoir of the cartridge in the same operation.

In some embodiments, any of the methods, cartridges, and kits for detecting a concentration of target cells within a sample can be used as part of an assay to determine susceptibility of the target cells to a treatment protocol. For example, in some embodiments, any of the methods, cartridges, and kits for detecting a concentration of target cells can be used as part an antibiotic susceptibility test (AST). For example, in some embodiments, a method includes conveying a first portion of the sample into a cartridge. The cartridge includes a separation portion and a detection portion. The separation portion includes a first surface and a second surface defining a separation chamber. The detection portion includes a detection surface that forms a boundary of a detection chamber. The detection chamber is fluidically coupled to the separation chamber, and the detection surface and the first surface of the separation portion form a non-zero detection angle. The detection surface is configured to capture the plurality of target cells. The cartridge is coupled within a first instrument. The first instrument is actuated to cause the instrument to: (1) rotate the cartridge at a rotation speed sufficient to cause the first portion of the sample to be conveyed through the separation chamber and into the detection chamber, and the target cells to be captured on the detection surface; (2) receive, via a detector of the instrument, a signal indicating a quantity of the target cells captured on the detection surface; and (3) determine, based on the signal, the concentration of the target cells in the sample. The method further includes processing, based on the concentration of the target cells within the first portion of the sample, a second portion of the sample. The second portion of the sample is then conveyed into a reaction chamber. The method then includes actuating a second instrument to perform a susceptibility assay on the second portion of the sample to determine susceptibility of the target cells to the treatment protocol.

As used herein, the singular forms "a," "an", and "the" include plural referents unless the context clearly dictates otherwise. Thus, for example, the term "a member" is intended to mean a single member or a combination of members, "a material" is intended to mean one or more materials, or a combination thereof.

As used herein, the terms "about" and "approximately" when used in connection with a referenced numeric indication means the referenced numeric indication plus or minus 10 percent of the value stated. For example, about 0.5 would include 0.45 and 0.55, about 10 would include 9 to 11, about 1000 would include 900 to 1100.

As used herein, a term referring to multiple components or portions thereof is intended to refer to a first component or a first portion thereof, and/or a second component or a second portion thereof, unless the context clearly dictates otherwise. Thus, for example, the term "reagents" is intended to refer to a "first reagent" and/or a "second reagent."

As used herein, a "set" can refer to multiple features or a singular feature with multiple parts. For example, when referring to set of walls, the set of walls can be considered as one wall with distinct portions, or the set of walls can be considered as multiple walls.

Specific words chosen to describe one or more embodiments are not intended to limit the invention. For example, spatially relative terms (such as "beneath", "below", "lower", "above", "upper", "proximal", "distal", and the like) may be used to describe the relationship of one element or feature to another element or feature as illustrated in the figures. These spatially relative terms are intended to encompass different positions (i.e., translational placements) and orientations (i.e., rotational placements) of a device in use or operation in addition to the position and orientation shown in the figures. For example, if a device in the figures were turned over, elements described as "below" or "beneath" other elements or features would then be "above" or "over" the other elements or features. Thus, the term "below" can encompass both positions and orientations of above and below. A device may be otherwise oriented (e.g., rotated 90 degrees or at other orientations) and the spatially relative descriptors used herein interpreted accordingly.

Likewise, descriptions of movement along (translation) and around (rotation) various axes includes various spatial device positions and orientations.

Similarly, geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

As used in this specification, the term "reagent" includes any substance that is used in connection with any of the methods described herein. For example, a reagent can include a composition for dilution of a sample, a wash solution, an anti-coagulation solution, a dye, a staining solution, or the like. A reagent can include a mixture of one or more constituents. A reagent can include such constituents regardless of their state of matter (e.g., solid, liquid or gas). Moreover, a reagent can include the multiple constituents that can be included in a substance in a mixed state, in an unmixed state and/or in a partially mixed state. A reagent can include both active constituents and inert constituents. Accordingly, as used herein, a reagent can include non-active and/or inert constituents such as, water, colorant or the like.

FIG. 1 shows an overhead view of a portion of an imaging cartridge 101. The structures shown here may be internal structures enclosed by the imaging cartridge 101. The imaging cartridge 101 comprises an enclosed inlet reservoir 102 into which a clinical sample may be deposited. The inlet reservoir 102 is in fluid communication with valves 103, which are in turn in fluid communication with a separation channel 104. The separation channel (also referred to herein as a separation chamber) can have any suitable thickness or channel depth. In some embodiments, the separation channel will be between 0.40 mm and 0.02 mm thick. In other embodiments, the separation channel will be between 0.05 mm and 0.20 mm thick. The separation chamber is continuous with an imaging channel 105. Optionally, the imaging channel 105 terminates in a waste chamber 106. The cartridge 101 further comprises a hub 107 around with the cartridge is rotated. Optionally, the cartridge 101 may contain one or more media reservoirs 108 of greater depth than the separation channel 105 or imaging channel 106. It should be understood that the portion of the imaging cartridge not shown may comprise a mirrored copy of the structures 102-106 and 108 shown in this figure, symmetric across a plane bisecting the hub 107.

Figure 2:
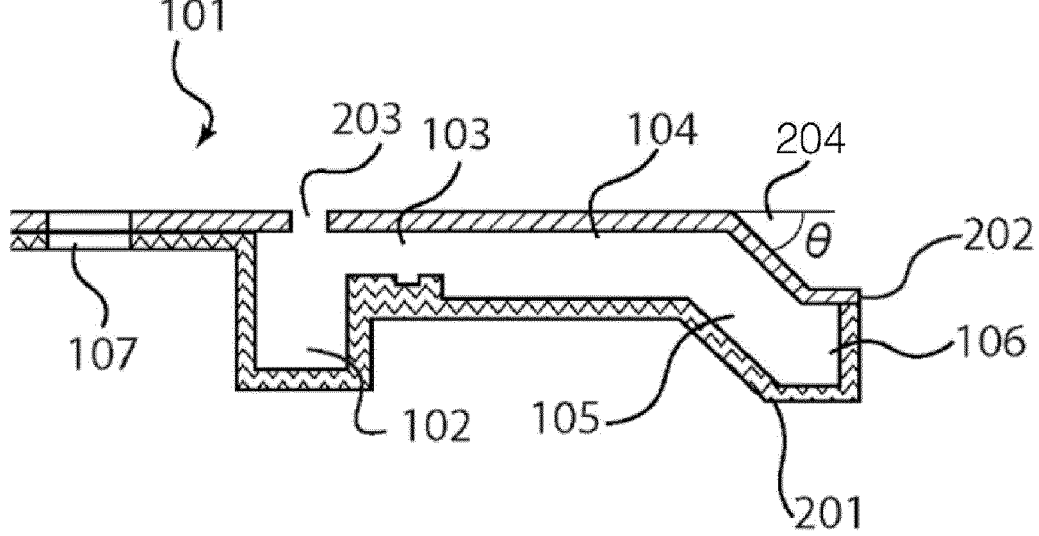
FIG. 2 is cross-sectional view of the cartridge shown in FIG. 1, taken along line X-X in FIG. 1.

FIG. 2 shows a cross-sectional view of a portion of the imaging cartridge 101 taken along the line X-X in FIG. 1. The cartridge may be constructed from two parts: a bottom part 201 and a top part 202. The bottom part 201 and top part 202 may be joined by any of the processes described herein, such as ultrasonic welding or laser welding to form an integral detection (or imaging) cartridge 101. The imaging cartridge 101 comprises an enclosed inlet reservoir 102 into which a clinical sample may be deposited. The enclosed inlet reservoir 102 may be connected to the outside by an inlet hole 203 and may have a greater depth than more distally located channels (e.g., the separation channel or the detection channel). The inlet reservoir 102 is in fluid communication with valves 103, which may comprise multiple channel depths smaller than the inlet reservoir 102. The valve may comprise a first depth following by a second depth greater than the first, followed by a third depth equal to the first. This structure serves to restrain liquid flow through the valve 103 unless sufficient pressure is applied to the fluid (e.g. during cartridge centrifugation). The valve 103 is in fluid communication with the separation channel 104.

The separation chamber 104 is continuous with the angled detection (or imaging) channel 105, which continues on a vertical angle 204 with respect to the separation chamber 104. Suitable values for the angle 204 may include 0.25 to 20 degrees, or preferably 0.5 to 10 degrees. Optionally, the imaging channel 105 terminates in a waste chamber 106, which may not share the same angle 204 as the angled imaging channel 105. The separation channel 104 and angled imaging channel 105 may have the same depth, measured perpendicular to the top and bottom enclosing surfaces. In some embodiments, the cartridge (and any of the cartridges described herein) can include a balance feature such that the center of mass of the cartridge is within hub 107.

Figure 3A:
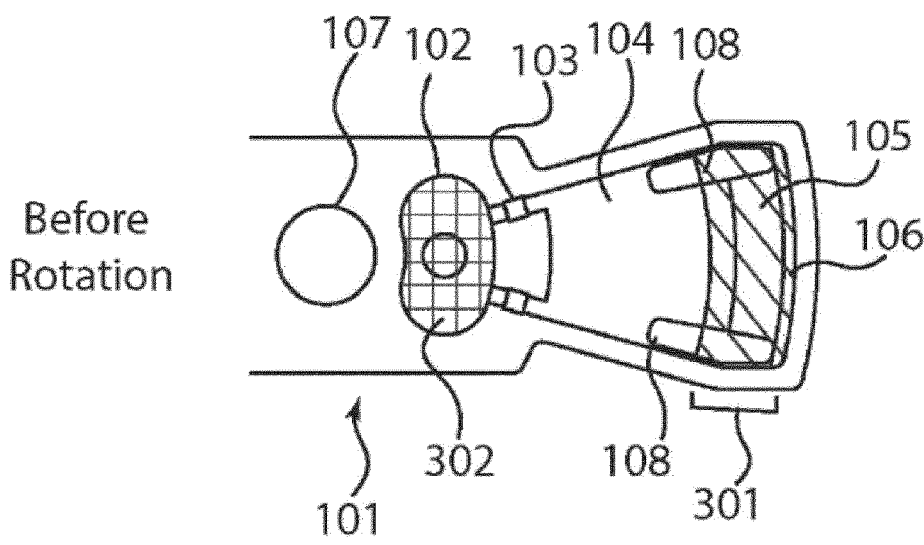
FIGS. 3A and 3B show a top view of the portion of the cartridge shown in FIG. 1 containing a sample prior to being rotated (FIG. 3A) and after being rotated (FIG. 3B).
Figure 3B:
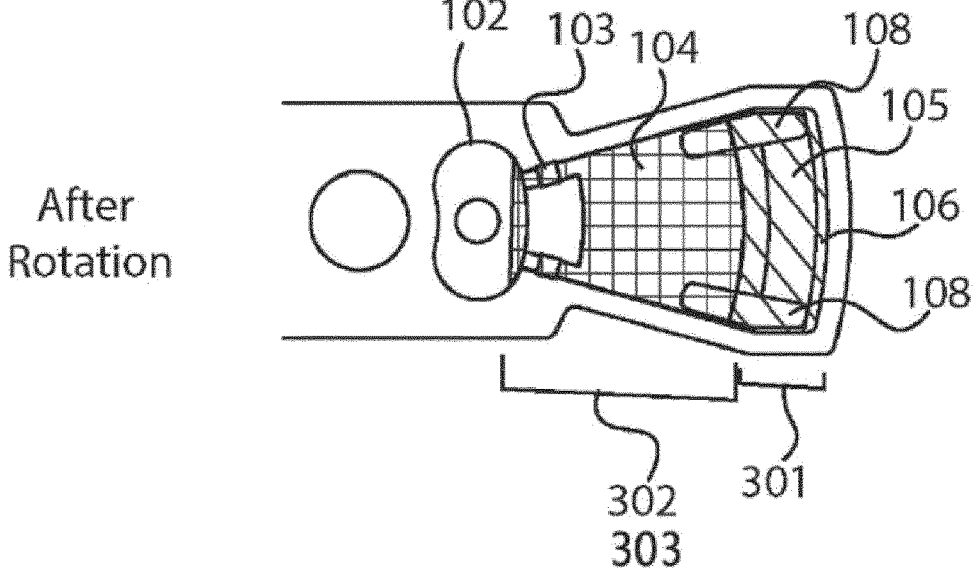

FIG. 3 shows a top view of a portion of the imaging cartridge 101 in two different states of action during intended operation. The imaging cartridge 101 initially contains a fluid density medium 301. The density medium 301 may fill the waste chamber 106, the angled imaging chamber 105, and a portion of the separation channel 104 and the media reservoirs 108. The density medium 301 can be any suitable medium of the types described herein that has a density greater than a density of a first portion of the sample and less than a density of a second portion of the sample. Specifically, the density medium 301 (and any of the density media described herein) can have a density greater than a density of certain contaminants within the sample, such as low-density platelets, unbound dyes, etc. The density medium 301 (and any of the density media described herein) can have a density less than a density of certain particles within the sample, such as the target cells, blood cells, high density platelets, etc. In this manner, as described below, during use the target cells can be conveyed through the density medium 301 and into the imaging channel 105, while other (e.g., lighter) contaminants are blocked from entering the detection region.

The clinical sample 302 may be introduced into the inlet chamber 102 by way of the inlet hole 203 (as described in FIG. 2). The clinical sample 302 (and any of the samples described herein) may contain particles 303 such as bacteria or other cells. The clinical sample 302 may be retained in the inlet reservoir for a period of time by the valves 103. During this time, reagents can be introduced into the clinical sample

302 to react. For example, in some embodiments, a membrane permeable DNA dye such as Syto 83, DAPI, or Hoechst 33258 may be introduced to fluorescently label DNA-containing cells. Upon centrifugation (i.e., rotation of the cartridge), the clinical sample 302 will enter the valves 103 and separation chamber 104 and will form a distinct layer inward from the density medium with respect to the center of rotation and in fluid contact with the density medium. During centrifugation the clinical sample 301 may also occupy a portion of the media reservoirs 108. A portion of the clinical sample 301 may also remain in the inlet reservoir 102.

FIGS. 4A and 4B show a cross-section of the distal end of the imaging cartridge 101 at the beginning (FIG. 4A) and end (FIG. 4B) of a rotation cycle (also referred to as a "spin"). As shown, the upper surface of the imaging channel 105 comprises the detection (or imaging) surface 401. In the beginning state, the clinical sample 302 has formed a layer inward from the center of rotation of the density medium 301. The clinical sample contains the target particles 303 (such as bacteria or cells), low-density contaminants 403, and high-density contaminants 404 (such as red blood cells, leukocytes, crystals, or large protein aggregates). It should be understood that "low-density contaminants" 403 could be replaced by higher density objects that are substantially smaller than the particles 303 and therefore do not migrate through the clinical sample 302 or the density medium 301 in a timely manner during spinning. Low-density contaminants 403 could include unbound dyes, cell fragments, proteins, or other matrix components in the clinical sample 302. The effective centrifugal force causes the target particles 303 and high-density contaminants 404 to migrate (pass through the density medium) in the radially outward direction 402.

Figure 6:
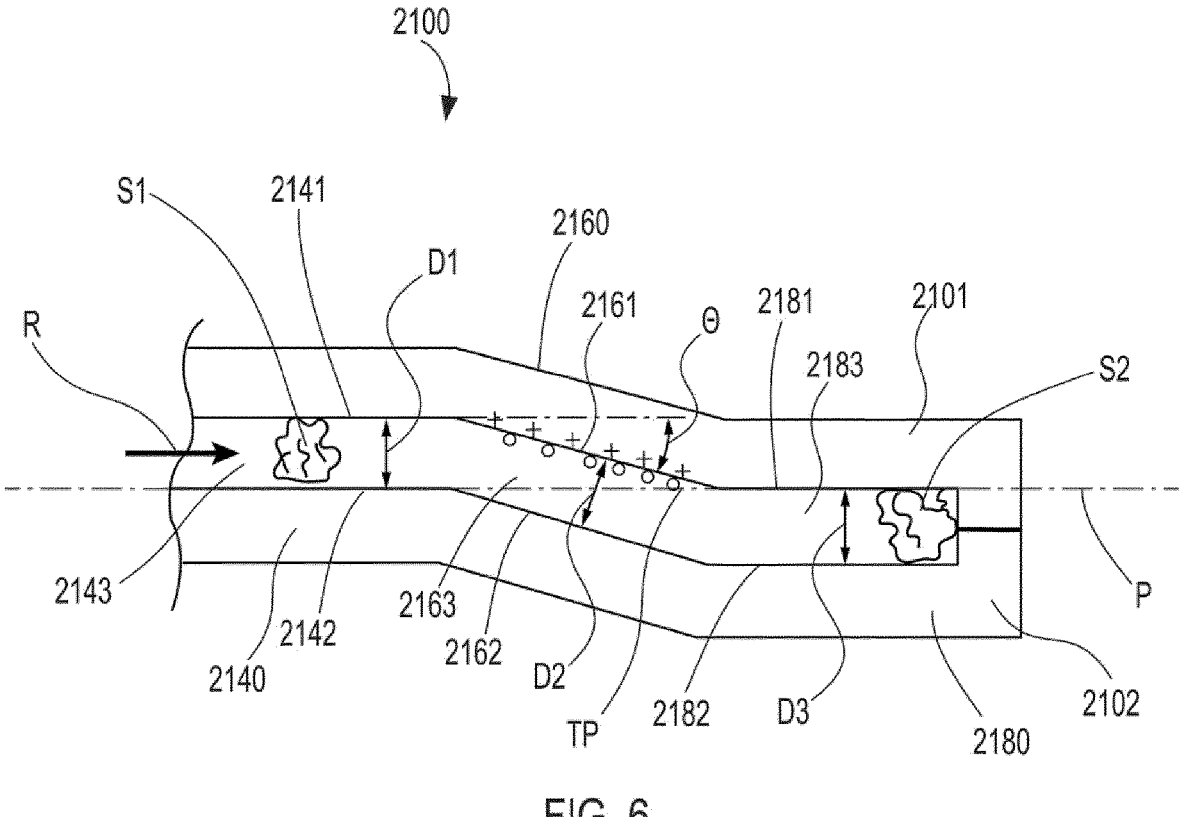
FIG. 6 is cross-sectional schematic illustration of a cartridge, according to an embodiment.

Referring to FIG. 4B, on completion of the spin, the target particles 303 will migrate until they contact the imaging surface 401. Low-density contaminants 403, however, will not migrate (or pass) through the density medium 301 and will therefore be kept away from the imaging chamber 105. High-density contaminants 404 will migrate faster and more forcefully than the target particles 303 and will therefore reside in the waste chamber 106 upon completion of the spin. Capture of all particles 303 by the imaging surface 401 is facilitated by having the upper surface of the waste chamber 106 being coplanar with or lower than the bottom surface of the separation chamber 104. For example, the cartridge 2100 shown in FIG. 6 shows a coplanar arrangement of the lower separation portion surface 2142 and the upper waste portion surface 2181 (which are aligned with the plane P). The arrangement ensures that particles 303 that were initially dispersed in the clinical sample 302 will come in contact with the imaging surface 401 assuming effective centrifugal force is much higher than natural gravity.

In some embodiments, the detection (or imaging) surface 401 (and any of the detection surfaces described herein) can be configured to capture the target particles 303. For example, in some embodiments, the detection (or imaging) surface 401 is treated with a surface modification 407 that attracts or binds particles 303. Moreover, the surface modification can be selected such that high-density contaminants 404 do not easily bind to the detection surface 401. For example, in some embodiments, the chemical modification 407 may comprise a charged coating including chemical moieties that retain a positive or negative electrical charge at the pH of the density medium. When using the surface to capture bacteria, the charge should be positive. Examples of appropriate coatings are polymers that are positively charged at neutral +/−3 pH such as Poly-L-lysine or Poly-ethylenimine, which will bind negatively charged particles such as bacteria. The surface modifications can be selected to minimize interference or disruption of the imaging techniques. Further, the imaging of target particles 303 may be facilitated by making the top outer surface 408 of the imaging chamber 105, and the bottom outer surface 409 of the imaging chamber 105, parallel with the imaging surface 401.

In use, the cartridge 101 (and any of the cartridges described herein) can be used in an optical system 410, which can receive a signal associated with an amount of the target particles 303 captured on the detection surface 401. Referring to FIG. 4B, the optical system can be configured at the same angle 204 as the imaging chamber 105 with respect to an axis 411 perpendicular to imaging surface 401. In other embodiments, the angle may not be included in the optical system 410 resulting in a distorted but possibly acceptable image. Imaging surface 401 may be illuminated by light 413 emitted by a light source 412 to facilitate imaging by the optical system 410. The light 412 may be of a wavelength that enables fluorescence imaging of particles 303. The light 412 may also be configured to provide non-fluorescent brightfield or darkfield illumination of the imaging surface 401. The light source may be placed co-axially with the optical system 410 or may be pointed in any other direction that illuminates the particles 303. The light source 412 may be integrated into the optical system 410 such as with an epi-fluorescent system. The optical system 410 may capture images of particles 303 bound to the imaging surface 401, enabling quantification of the particles 303. The number of particles 303 in a given image of the imaging surface 401 will correlate with the original concentration of particles 303 suspended in the clinical sample 302.

In some embodiments, to improve analytical precision, a method may include capturing multiple images from different regions of the angled imaging channel 105 to obtain an average number of particles per image. One method for achieving this goal is to slowly rotate the cartridge 101 about the hub 107 such that different portions of the angled imaging channel 105 are located in the imaging path of the optical system 410. In such embodiments, the imaging surface 401 will comprise a curved surface rather than a flat surface to maintain a constant cross-sectional angle 204 at each radial section of the cartridge as it is rotated. This curvature increases with increasing angle 204, reducing the area that can be held in focus for any given image (some regions will be closer to the optical system and some will be further).

As shown, the detection (or imaging) surface 401 and the surfaces defining the separation channel 104 define the detection angle 204. The detection angle 204 is along the radial axis of the cartridge 101, i.e., an axis that intersects an axis of rotation (or central point) of the cartridge in a radial direction. Specifically, the detection angle 204 is within a cross-sectional plane defined by the axis of rotation and the radial axis, as shown in the cross-sectional views of FIGS. 2, 4A, and 4B. Moreover, the detection angle 204 for the cartridge 101 is in a downward direction (with respect to the opening 102 and/or the direction of gravity). Said another way, the detection angle 204 is such that the waste chamber 106 is below the separation channel 104 with respect to the opening 102. In this manner, the imaging surface 401 is on the upper (or top) surface of the top part 202 that forms the cartridge. This arrangement can provide for advantageous imaging from the top (as compared to a bottom-imaging system). Such an arrangement can also provide improved liquid stability within the channels, which can facilitate the inclusion of chambers (or channels) having greater depth (or thickness) than that for cartridges having an upward detection angle. The inclusion of a surface treatment to enhance capture of the target particles 303 can minimize the settling effect of gravity after completion of rotation and during imaging.

Figure 5A:
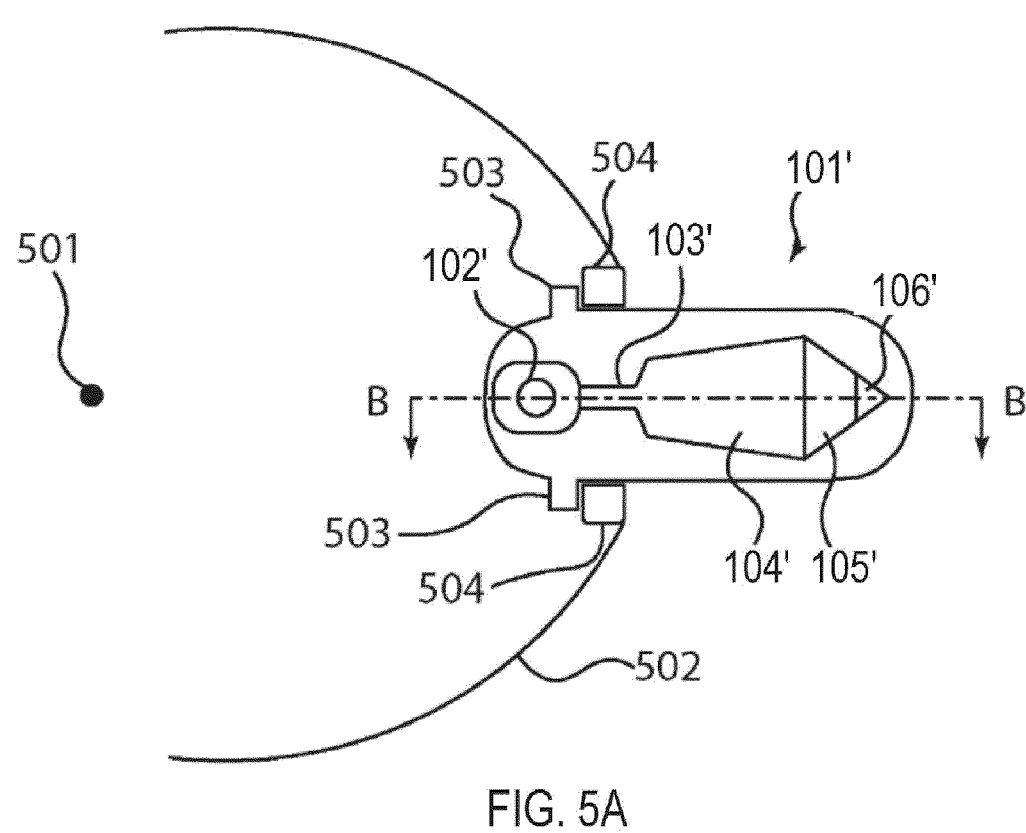
FIG. 5A is a top view of a portion of a cartridge, according to an embodiment.
Figure 5B:
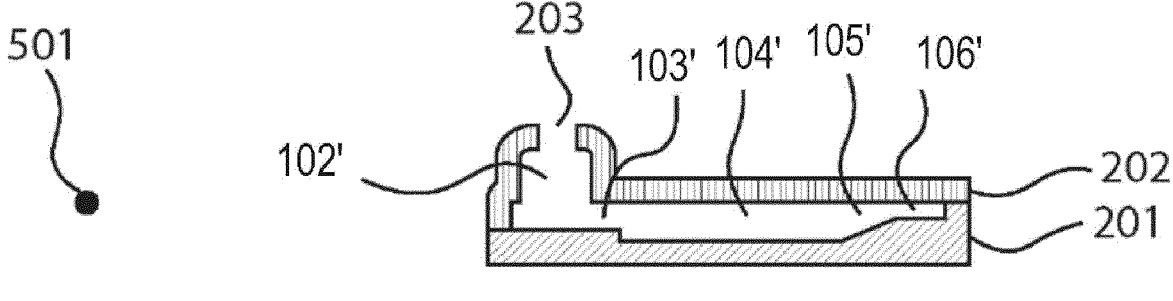
FIG. 5B is cross-sectional view of the cartridge shown in FIG. 5A, taken along line B-B in FIG. 5A.

In other embodiments, however, the detection angle can be in an upward direction (with respect to the opening and/or the direction of gravity). Such an arrangement can limit any negative effects of gravity. For example, FIGS. 5A and 5B show an imaging cartridge 101' that is an alternate embodiment of the cartridge 101 shown in FIGS. 1-4B. In this embodiment, the imaging cartridge 101' encloses a sample inlet chamber 102', a valve 103', separation channel 104', angled imaging chamber 105', and waste chamber 106'. In this embodiment, the imaging surface 401' is on the bottom part 201' with the advantage of retaining any particles on the imaging surface with the assistance of natural gravity. In this embodiment, the thickness of the separation chamber 104' is larger than the thickness of the waste chamber 106', with the bottom portion of the imaging chamber 105' being angled to connect the separation chamber 104' to the waste chamber 106'. In some embodiments, the imaging cartridge 101' is rotated around an axis of rotation 501 external to the cartridge 101'. The cartridge 101' may be held in rotation by a rotor 502 that holds, locks or constrains the cartridge in place during rotation. The rotor 502 may interface with the cartridge 101' by protrusions 503 on the cartridge 101' that interlock with protrusions 504 on the rotor 502. In other embodiments, the cartridge can be attached to a rotor or rotating hub by any suitable mechanism. During rotation, the cartridge 101' will be held in place by reaction force from the protrusions 504 on the rotor 502. The interfacing surfaces of protrusions 503 and 504 will preferably be vertical with respect to the axis of rotation 501. This embodiment may include density medium and chemical modifications to the imaging surface 401 as described herein. This embodiment may also be assessed by an optical system and illuminator as described in connection with FIGS. 4A and 4B.

Figure 5C:
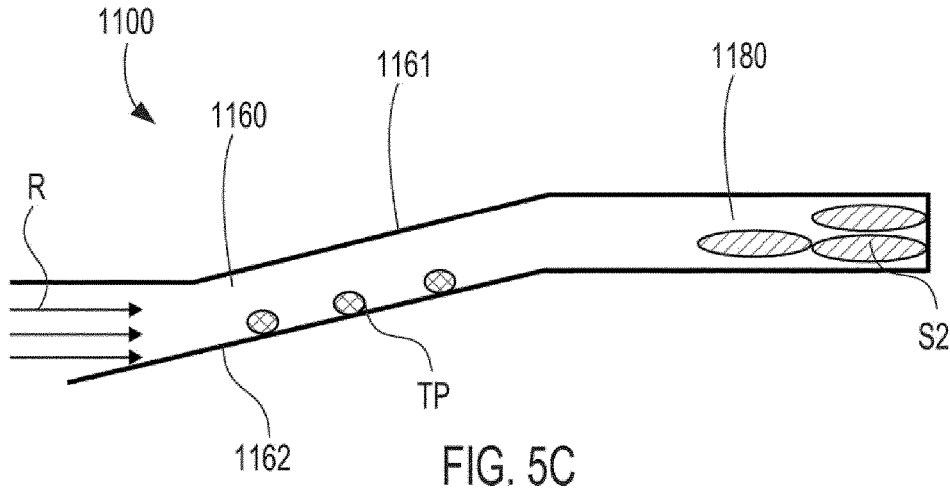
FIG. 5C is cross-sectional schematic illustration of a cartridge, according to an embodiment.

FIG. 5C is a cross-sectional schematic illustration of a cartridge 1100 according to embodiment. Like the cartridge 101', the cartridge 1100 is also characterized by having an upward detection angle that results in the target particles TP being captured on a bottom surface of the cartridge 1100. Specifically, the cartridge 1100 includes at least a detection portion 1160 and a waste portion 1180. The detection portion 1160 includes a first (or upper) surface 1161 and a second (or bottom) surface 1162 that define a detection chamber. In use, rotation of the cartridge 1100 causes a sample to flow, be conveyed and/or otherwise move in a radial direction from a separation portion into the detection portion 1160, as shown by the arrows R. In some embodiments, the cartridge 1100 can include a density medium, of the types described herein.

The centrifugation of the sample causes the target particles TP to contact and be captured by the second surface 1162. In some embodiments, the second surface 1162 can be configured to enhance the adhesion of the target particles TP thereto. As shown in FIG. 5C, the larger and/or more dense contaminants are conveyed into the waste portion 1180, and therefore do not cause undesirable interference with the detection (i.e., the counting and/or imaging) of the target particles TP captured on the second surface 1162.

In some embodiments, the dimensions and geometric relationship of portions of any of the cartridges described herein can be selected to optimize the collection performance and detection for certain target particles and/or certain samples. For example, in some embodiments, a higher detection angle can increase certain particle capture characteristics (i.e., due to greater impingement of the target particles), but can also result in greater instability during and after rotation of the cartridge. Specifically, in some embodiments, a separation chamber and/or a detection chamber having a depth of 125 μm (0.125 mm) can exhibit suitable mixing stability with a detection angle of 5 degrees. Conversely, in other embodiments, a separation chamber and/or a detection chamber having a depth of 250 μm (0.25 mm) can exhibit undesirable mixing stability with a detection angle of 5 degrees. Additionally, in some embodiments, having the upper surface of the waste chamber being coplanar with or lower than the bottom surface of the separation chamber can improve the capture efficiency of the detection surface. For example, FIG. 6 is a cross-sectional schematic illustration of a cartridge 2100 according to embodiment. The cartridge 2100 is constructed from a first (or upper) member 2101 and a second (or lower) member 2102 to form a separation portion 2140, a detection (or imaging) portion 2160, and a waste (or collection) portion 2180. The separation portion 2140 defines a separation chamber (or channel) that is bounded by a first surface 2141 (of the first member 2101) and a second surface 2142 (of the second member 2102). The separation chamber has a depth D1 (also referred to herein as a thickness) that is perpendicular to the first surface 2141 and the second surface 2142. The depth D1 is also perpendicular to the radial direction R.

The detection portion 2160 defines a detection chamber (or channel) 2163 that is bounded by a first surface 2161 (of the first member 2101) and a second surface 2162 (of the second member 2102). The first surface 2161 (also referred to as a detection surface or an imaging surface) is nonparallel to at least one of the first surface 2141 or the second surface 2142, which allows target particles (or cells) to impinge on the detection surface 2161, as described in detail herein. Similarly stated, the detection surface 2161 and the first surface 2141 of the separation portion 2160 form a non-zero detection angle Θ. The detection angle Θ is along the radial axis (the radial direction is identified by the arrow R) of the cartridge 2100, i.e., an axis that intersects an axis of rotation (or central point) of the cartridge in a radial direction. Specifically, the detection angle Θ is within a cross-sectional plane defined by the axis of rotation and the radial axis. Moreover, the detection angle Θ is in a downward direction. In this manner, the detection surface 2161 is on the first member 2101 that forms the cartridge 2100. In some embodiments, the detection angle Θ is between about 1 degree and about 8 degrees. In other embodiments, the detection angle Θ is between about 1.5 degrees and about 5 degrees. In yet other embodiments, the detection angle Θ is about 2 degrees. In some embodiments, the detection surface 2161 and the first surface 2141 are monolithically constructed, and the detection angle is the "bend" between the surfaces.

Figure 18:
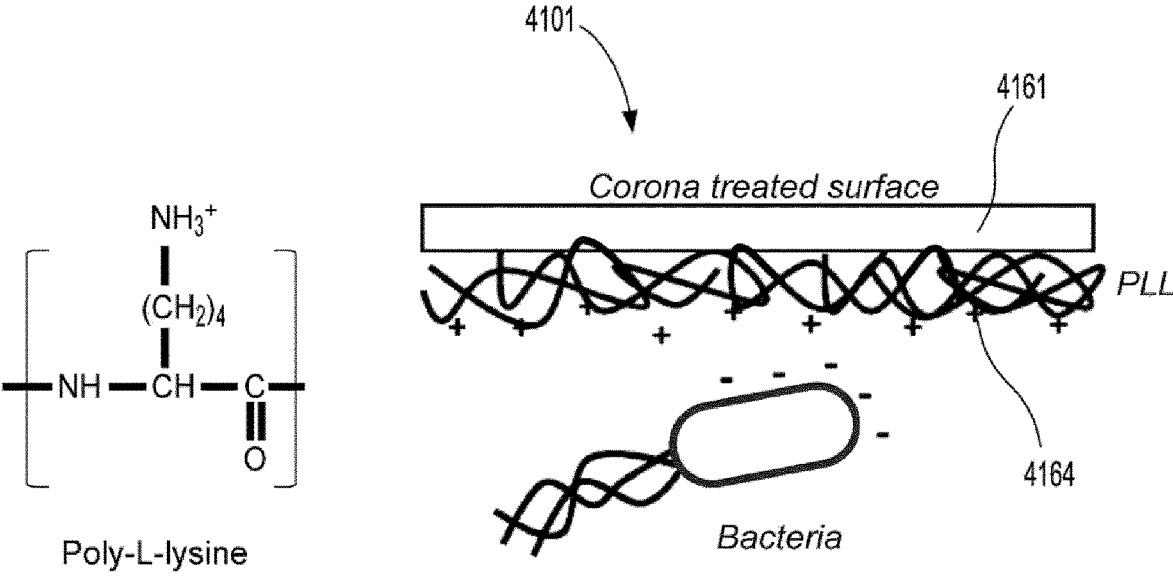
FIG. 18 is a schematic illustration of the top member of the cartridge shown in FIGS. 9 and 10, showing a surface treatment on a detection surface.

In some embodiments, the detection surface 2161 (and any of the detection surfaces described herein, including the detection surface 4161 described below) is configured to capture the target particles TP. For example, in some embodiments, the detection surface 2161 can be modified to enhance adhesion of the target particles TP. Such modifications can include, for example, a chemical modification, a surface coating, electrically charging the detection surface 2161, or a combination of these modifications. For example, in some embodiments, the detection surface 2161 (and any of the detection surfaces described herein, including the detection surface 4161 described below) can include a marking or texture that can assist in the identification of the boundaries for imaging. In other embodiments, the detection surface 2161 can be modified by Corona treatment (also referred to as air plasma treatment). This process disrupts the polymeric chains at the surface, which can increase the surface energy of the detection surface 2161, thereby improving improve the surface adhesion properties of the detection surface 2161. In other embodiments, the surface modification can include applying a charged coating, such as Poly-L-lysine (PLL) or Polyethylenimine, which will bind negatively charged particles (e.g., bacteria). In some embodiments, the charged polymer can include ($-NH_3^+$) for creating a positive surface charge. The charged coating can be applied in any suitable manner. In some embodiments, the charged polymer coating can be applied by attachment using carbodiimide compounds. Carbodiimide compounds are cross-linking compounds that can promote application of charged polymeric coatings, such as PLL. In other embodiments, the charged polymer coating can be applied by photochemically induced polymerization and grafting of the desired coating. Moreover, the detection surface 2161 can be modified using a combination of any suitable procedures to enhance the adhesion properties of the surface. For example, as shown in FIG. 18 (which references the detection surface 4161), any of the detection surfaces described herein, including the detection surface 2161 can be modified using a combination of Corona treatment and a PLL coating. Referring again to FIG. 6, the positive charge of the detection surface 2161 is shown by the (+), which improves the adhesion properties to capture the target particles TP (e.g., bacteria) therein.

In some embodiments, the detection surface 2161 can be modified to have a surface finish (or roughness) that is conducive to capturing the target particles TP. The surface finish (or roughness) can also be selected to provide identification and/or marking characteristics that do not interfere with imaging procedures. In this manner, the detection surface and other portions of the cartridge can include markings to assist in collection and evaluation of imaging data. The detection chamber 2163 has a depth D2 (also referred to herein as a thickness) that is perpendicular to the first (detection) surface 2161 and the second surface 2162. In some embodiments, the depth D2 can be the same as the depth D1 of the separation chamber. In other embodiments, the depth D2 can be different from the depth D1 of the separation chamber. The waste portion 2180 defines a waste chamber (or channel) 2183 that is bounded by a first surface 2181 (of the first member 2101) and a second surface 2182 (of the second member 2102). The first surface 2181 of the waste portion 2180 and the second surface 2142 of the separation portion 2140 are coplanar within a plane P. As described above, this arrangement provides improved capture efficiency within the detection chamber 2163. In other embodiments, the first surface 2181 of the waste portion 2180 is lower than the second surface 2142 of the separation portion 2140. The waste chamber 2183 has a depth D3 (also referred to herein as a thickness) that is perpendicular to the first surface 2181 and the second surface 2182. In some embodiments, the depth D3 can be the same as the depth D1 of the separation chamber and/or the depth D2 of the detection chamber 2163. In other embodiments, the depth D3 can be different from either or both the depth D1 of the separation chamber and/or the depth D2 of the detection chamber 2163. The depth D1, the depth D2, and/or the depth D3 can be any suitable values as described herein. For example, in some embodiments, the depth D1, the depth D2, and/or the depth D3 can less than about 0.6 mm. In other embodiments, the depth D1, the depth D2, and/or the depth D3 can be less than about 0.3 mm. In yet other embodiments, the depth D1, the depth D2, and/or the depth D3 can be about 0.250 mm. In yet other embodiments, the depth D1, the depth D2, and/or the depth D3 can be about 0.125 mm.

Figure 7:
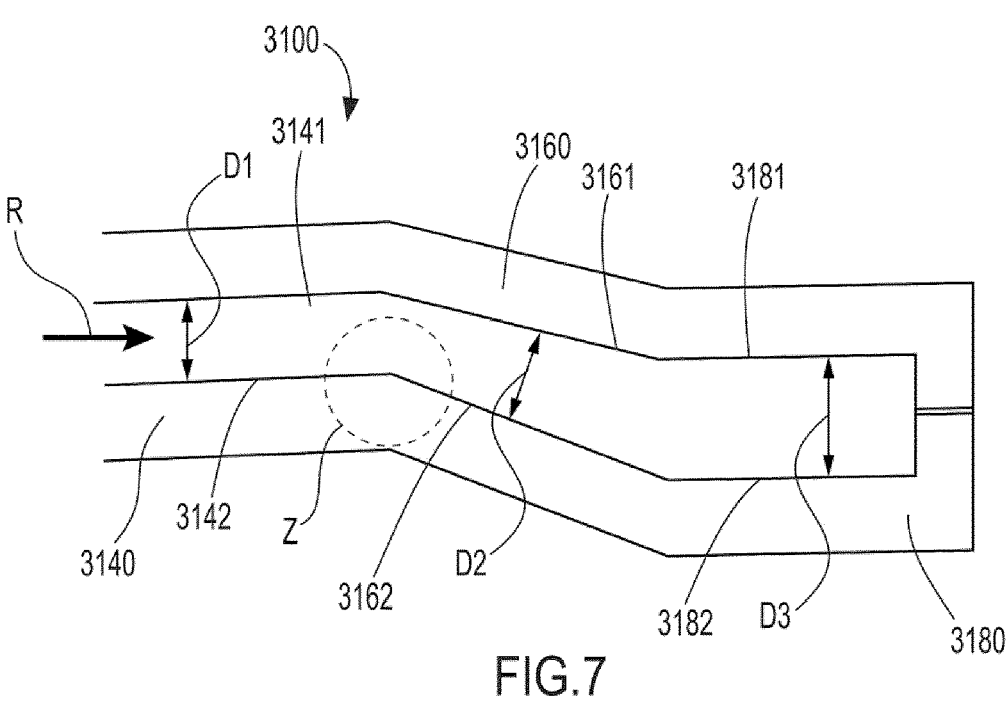
FIG. 7 is cross-sectional schematic illustration of a cartridge, according to an embodiment.

As shown, the sample can include first portion (identified as S1 in FIG. 6), the target particles TP, and a second portion (identified as S2 in FIG. 6). The first portion S1 can include the low-density contaminants, such as, unbound dyes, cell fragments, proteins, or other matrix components. The second portion S2 can initially include the target particles TP, as well as other high-density contaminants, such as red blood cells, leukocytes, crystals, or large protein aggregates. In use, the effective centrifugal force causes the target particles TP and high-density contaminants S2 to migrate in the radially outward direction, as shown by the arrow R. The target particles TP will migrate until they contact the detection surface 2161. Low-density contaminants S1, however, are retained in the separation portion 2140 (e.g., being blocked by a density medium or other mechanism) and are therefore prevented from reaching the detection surface 2161. Although the cartridge 2100 is shown as having the depth D1 being substantially equal to the depth D2, in other embodiments, a cartridge can include a detection chamber having a depth (or thickness) that is greater than that of the separation chamber. Similarly stated, in some embodiments, a cartridge can include a continuous channel (also referred to as a path or a chamber) that diverges (i.e., increases in cross-sectional area) from the separation portion to the detection portion. For example, FIG. 7 shows a cross-sectional schematic illustration of a cartridge 3100 according to embodiment. The cartridge 3100 includes a separation portion 3140, a detection (or imaging) portion 3160, and a waste (or collection) portion 3180. The separation portion 3140 defines a separation chamber (or channel) that is bounded by a first surface 3141 and a second surface 3142 (of the second member 2102). The separation chamber has a depth D1 (also referred to herein as a thickness) that is perpendicular to the first surface 3141 and the second surface 3142. The depth D1 is also perpendicular to the radial direction R.

The detection portion 3160 defines a detection chamber (or channel) that is bounded by a first surface 3161 and a second surface 3162. The first surface 3161 (also referred to as a detection surface or an imaging surface) is nonparallel to at least one of the first surface 3141 or the second surface 3142, which allows target particles (or cells) to impinge on the detection surface 3161, as described in detail herein. Similarly stated, the detection surface 3161 and the first surface 3141 of the separation portion 3160 form a non-zero detection angle (not identified in FIG. 7). The detection chamber has a depth D2 (also referred to herein as a thickness) that is perpendicular to at least the first (detection) surface 3161. As shown, the depth D2 is greater than the depth D1 of the separation chamber. Thus, the overall chamber area from the separation chamber to the detection chamber diverges. Although the first surface 3161 is shown as being nonparallel to the second surface 3162, in other embodiments, the first surface 3161 can be parallel to the second surface 3162. Similarly stated, although the detection chamber is shown as having a diverging cross-sectional area, in other embodiments, the detection chamber can have a substantially constant cross-sectional area.

The waste portion 3180 defines a waste chamber (or channel) that is bounded by a first surface 3181 and a second surface 3182. The waste chamber 3183 has a depth D3 (also referred to herein as a thickness) that is perpendicular to the first surface 3181 and the second surface 3182. In some embodiments, the depth D3 can be the same as the depth D2 of the detection chamber 3163. In other embodiments, the depth D3 can be different from either or both the depth D1 of the separation chamber and/or the depth D2 of the detection chamber 2163. The depth D1, the depth D2, and/or the depth D3 can be any suitable values as described herein.

Figure 8A:
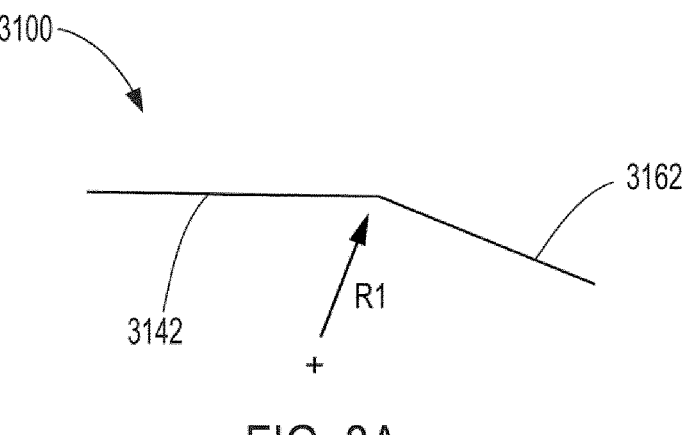
FIG. 8A is an enlarged view of a portion of the cartridge shown in FIG. 7 identified by the region Z in FIG. 7.
Figure 8B:
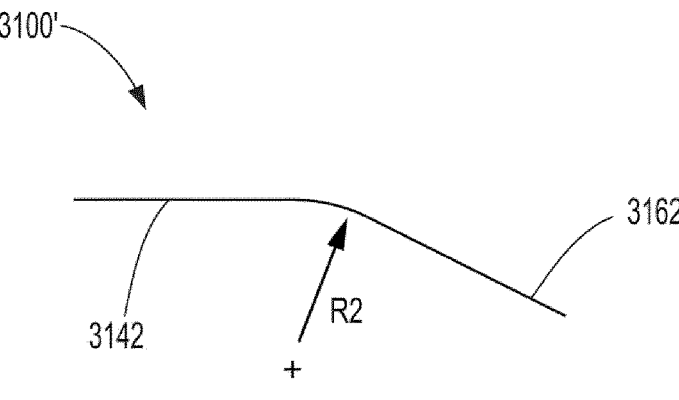
FIG. 8B is an enlarged view of a portion of a cartridge according to an embodiment, showing a region similar to that identified by the region Z in FIG. 7.

In some embodiments, the first surface of the separation portion and the adjoining detection surface for any of the cartridges described herein can be monolithically constructed. For example, in some embodiments, the cartridge 3100 can be formed from two separate pieces, similar to the first (or top) member 4101 and the second (or bottom) member 4102 shown with reference to the cartridge 4100. Moreover, such embodiments, the region between the first surface and the detection surface can have the desired geometric dimensions to produce the desired flow during the rotation cycle. For example, referring to FIGS. 8A and 8B, in some embodiments the cartridge 3100 (and any of the cartridges described herein) can include a transition region between any of the surfaces forming a boundary between the separation portion 3140, the detection portion 3160, and the waste portion 3180. The transition region can be controlled to ensure the desired flow performance between the cartridge portions during a rotation cycle. For example, in some embodiments, a transition region can be defined to produce a "sudden expansion" or to otherwise limit a smooth transition that may produce undesired movement of particles and/or fluids within the cartridge 3100. As one example, FIG. 8A shows a transition region between the second surface 3142 of the separation portion and the second surface 3162 of the detection portion that defines a radius of curvature R1. As shown, the radius of curvature R1 is relatively small, which produces a relatively sharp-edge transition (as compared to the cartridge 3100' in FIG. 8B). In some embodiments, the radius of curvature R1 is less than about 0.100 mm. In other embodiments, the, radius of curvature R1 is less than about 0.050 mm. In yet other embodiments, the, radius of curvature R1 is less than about 0.025 mm. Conversely, FIG. 8B shows a transition region between the second surface 3142 of the separation portion and the second surface 3162 of the detection portion that defines a radius of curvature R2. As shown, the radius of curvature R2 is relatively large, which produces a relatively smooth transition (as compared to the cartridge 3100 in FIG. 8A). In some embodiments, the radius of curvature R2 is greater than about 0.100 mm.

FIGS. 9-17 show various views of a cartridge 4100 according to an embodiment. The cartridge 4100 can be included within any of the systems and can be used in connection with any of the methods described herein. For example, as described herein, the cartridge 4100 can be rotated to produce centrifugal separation of a sample (e.g., blood, urine, or any other suitable biological sample) to cause target particles (e.g., bacteria) to be captured by a detection surface. The cartridge 4100 can be used with an optical system, such as the optical system 410 described herein, to determine a concentration of the target particles within the sample. Moreover, in some embodiments, the cartridge 4100 can be used in connection with additional methods, such as antibiotic susceptibility test.

The cartridge 4100 is constructed from a first (or upper) member 4101 and a second (or lower) member 4102 coupled together to define the chambers and features described herein. The first member 4101 defines a pair of alignment openings 4106 and the second member 4102 includes a corresponding pair of alignment pins 4105 to assist in joining the two members together. The first member 4101 and the second member 4102 can be joined together using any suitable technique as described herein, including by ultrasonic welding (see e.g., the welding protrusion 4108 in FIG. 14), by an adhesive joint, or other suitable method. In other embodiments, the cartridge 4100 (or any other cartridges described herein) can be monolithically constructed. The cartridge 4100 includes (or defines) a central hub (or connection opening) 4110. The cartridge 4100 can be coupled to a rotation element (not shown) of an instrument via the central hub 4110. The cartridge 4100 can be rotated by the rotation element about a rotation axis Arot to perform any of the methods described herein.

Figure 9:
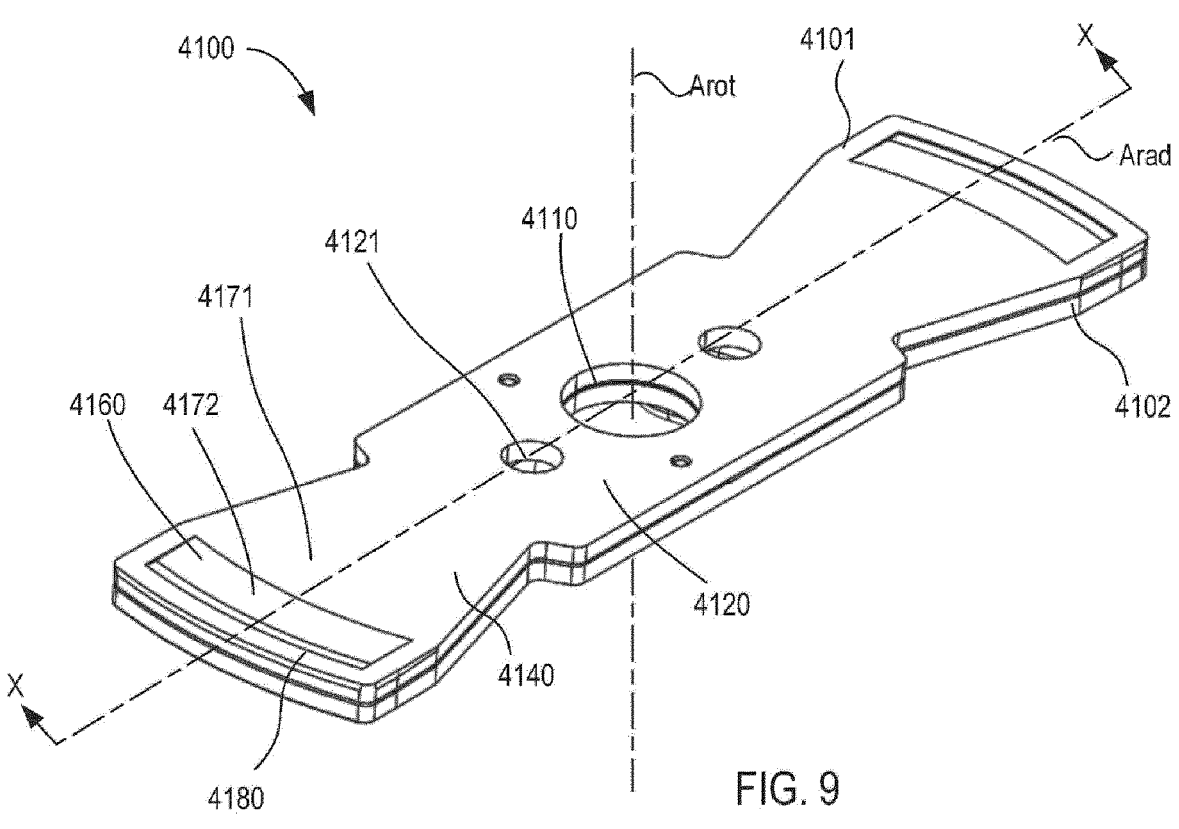
FIGS. 9 and 10 are perspective views of a cartridge, according to an embodiment.
Figure 10:
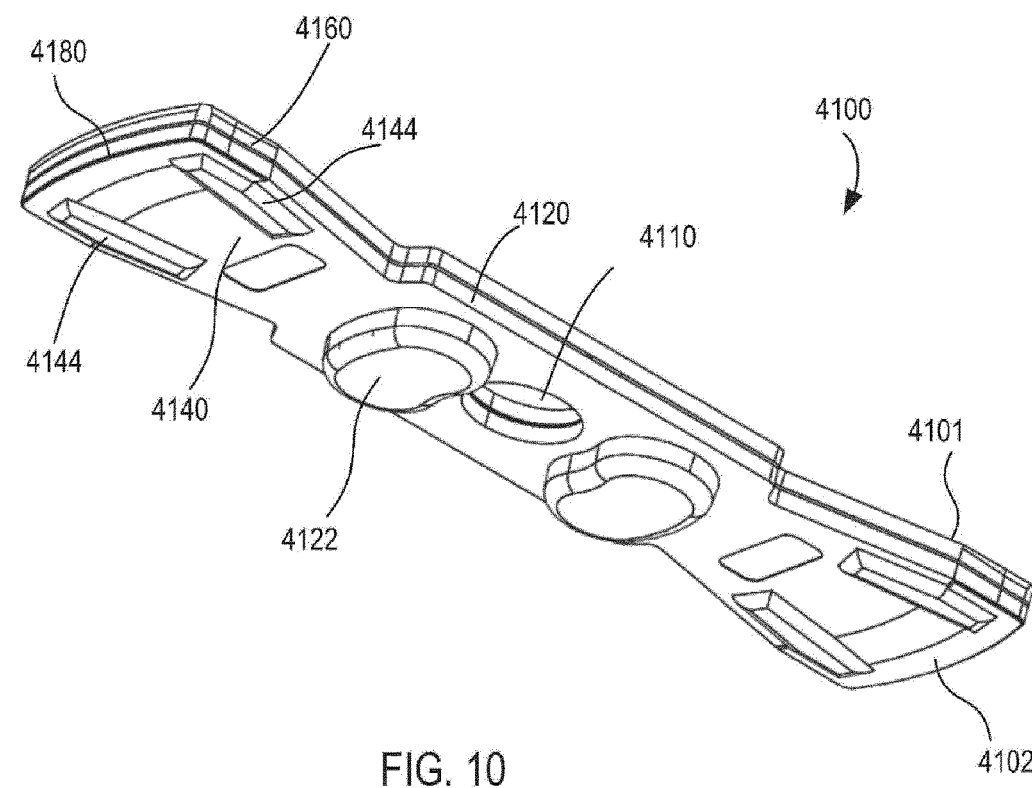

As shown, the cartridge 4100 is symmetrical about the rotation axis Arot, such that the cartridge includes two inlet portions 4120, two separation portions 4140, two detection (or imaging) portions 4160, and two waste (or collection) portions 4180. Because the cartridge 4100 is symmetrical about the rotation axis Arot, only one of each of these portions is identified and described below. In other embodiments, a cartridge can be similar to the cartridge 4100, but need not be symmetrical and can include only one inlet portion, separation portion, detection portion, and waste portion. As shown in FIG. 9, the cartridge 4100 defines a radial axis Arad that is normal to the rotation axis Arot.

Figure 15:
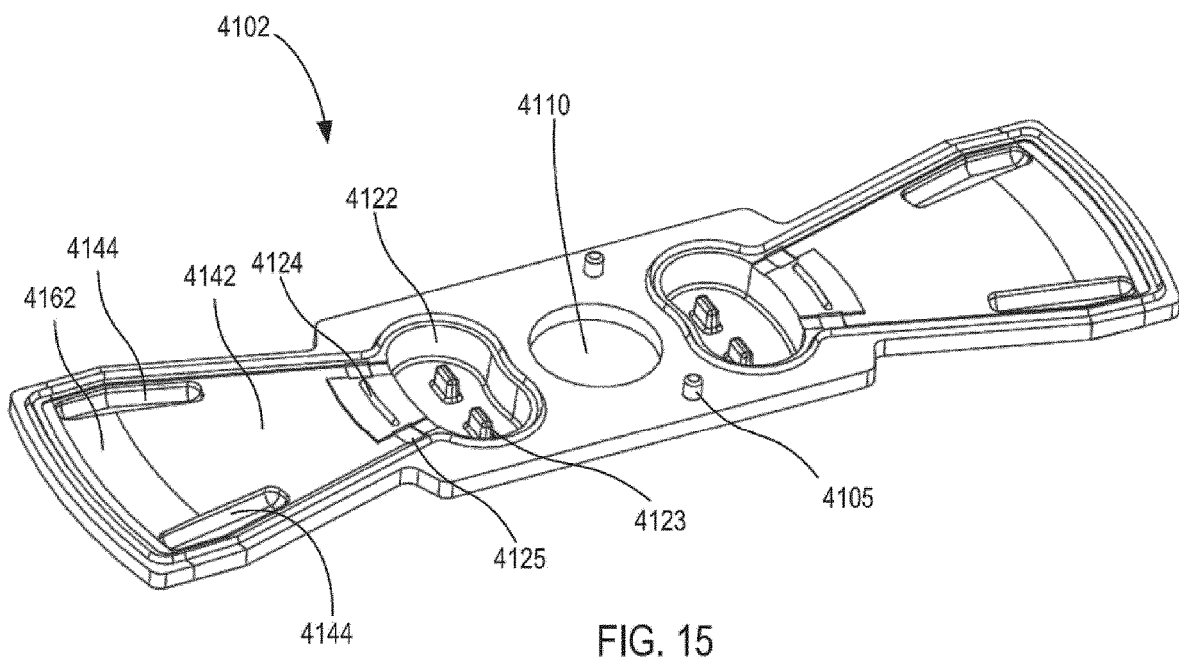
Figure 16:
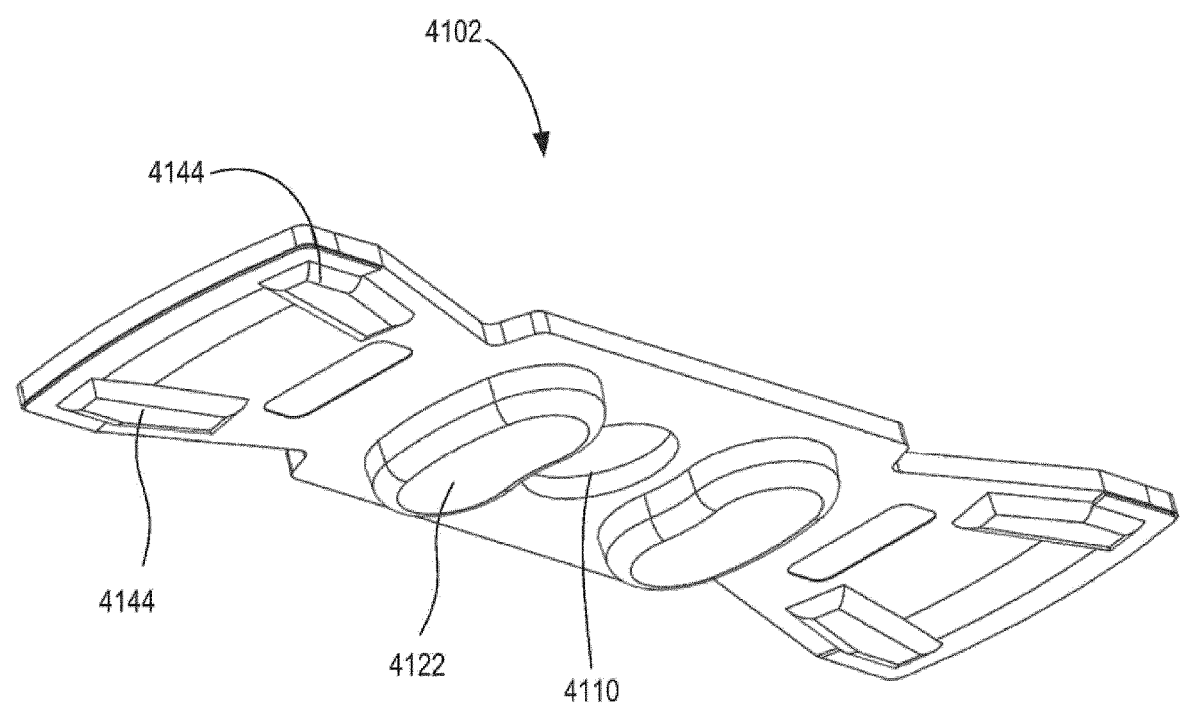
FIG. 16 is a bottom perspective view of the bottom member of the cartridge shown in FIGS. 9 and 10.

The inlet portion 4120 defines an inlet reservoir 4122 (defined by the second member 4102) and an opening 4121 (defined by the first member 4101) through which a sample can be conveyed into the inlet reservoir 4122. As shown in FIG. 15, the inlet reservoir includes protrusion 4123. The protrusions 4123 can provide structures that can enhance venting while the sample is being conveyed into the inlet reservoir. In some embodiments, the protrusions 4123 (or other structures within the reservoir, not shown) can enhance mixing (e.g. of the sample and any other constituents added into the inlet reservoir) or other flow performance during a rotation cycle. The second member 4102 includes a weld protrusion 4124 that serves to join the inner surfaces together. The second member also defines a pair of valve openings 4125 that fluidically couple the inlet reservoir 4122 to the separation chamber 4143. The valve openings 4125 are configured to limit the flow of the sample from the inlet reservoir 4122 into the separation chamber 4143 prior to the rotation of the cartridge 4100. Similarly stated the valve openings 4125 are sized such that the sample is retained within the reservoir 4122 until the centrifugal forces (or pressure within the sample) urging the sample outward along the radial axis Arad towards the separation channel 4143 (see FIG. 11) exceed a predetermined value. In this manner, the valve openings 4125 acts as a capillary valve to limit the flow of the sample until the fluid adhesion forces are exceeding during the rotation cycle. This arrangement allows the sample to be mixed with reagents within the inlet reservoir 4122, such as a dilution reagent, a staining reagent (or dye), and any other suitable reagents. Although the valve openings 4125 are "passive" valves that do not change configurations during use, in other embodiments, the cartridge 4100 can include any suitable type of valve or flow restriction to limit flow between the inlet reservoir 4122 and the separation chamber 4143. Such valves can include, for example an active valve, such as a check valve arrangement that is actuated by centrifugal forces (e.g., when the cartridge exceeds a predetermined rotational speed), a frangible valve that is ruptured or punctured during use, or the like.

The separation portion 4140 defines a separation chamber (or channel) 4143 that is bounded by a first surface 4141 (of the first member 4101) and a second surface 4142 (of the second member 4102). The second member 4102 defines two reservoirs 4144 within which a density medium can be retained within the cartridge. This arrangement can ensure that a sufficient volume of the density medium is present within the cartridge 4100 to ensure accurate collection and/or capture of the target cells on the detection surface 4161. For example, the reservoirs 4144 can provide an additional volume of between about 25 μL and about 75 μL to ensure that a sufficient amount the density medium is available after storage for a long period of time (e.g., up to about 1 year or up to about 2 years). This additional volume can account for potential evaporation of the density medium. Although the separation portion 4140 is shown as including two separate (i.e., non-contiguous) reservoirs 4144, in other embodiments, any arrangement of reservoirs for maintaining the density medium can be employed. For example, in some embodiments, the separation portion 4140 can include a single reservoir.

Figure 21:
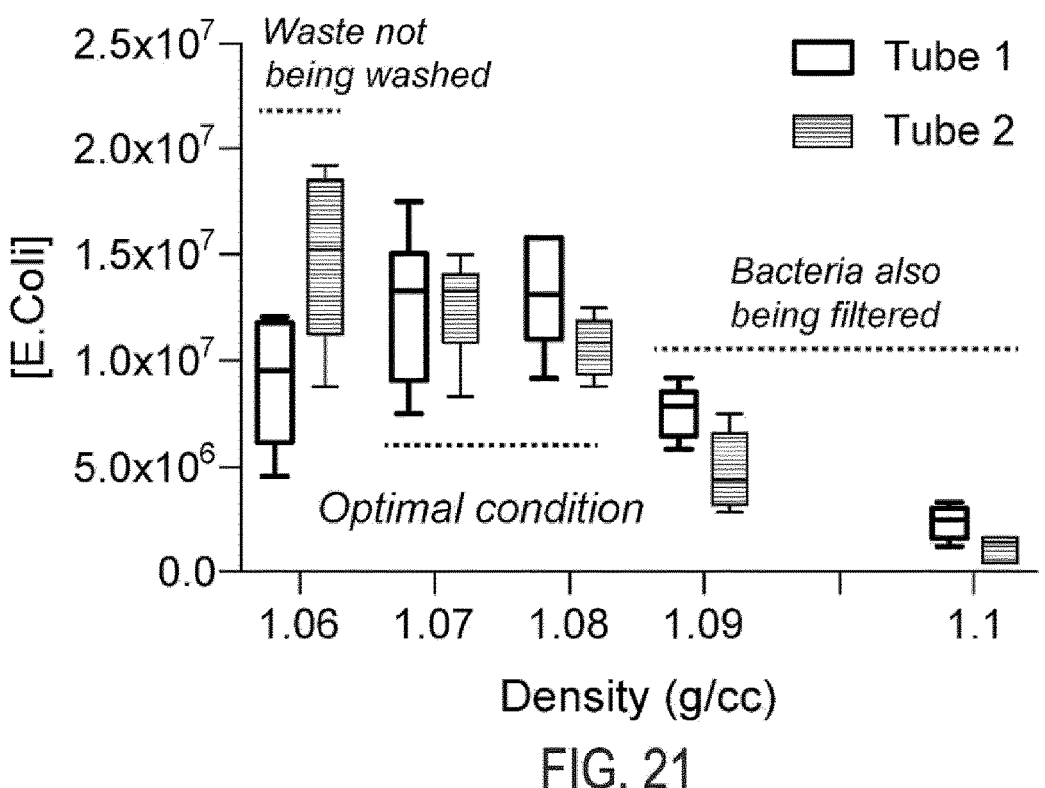
FIG. 21 is a graph showing experimental data associated with a density medium within a cartridge, according to an embodiment.

The density medium can be any density medium of the types shown and described herein. For example, FIG. 21 shows the effectiveness of density medium in filtering the low-density contaminants as tested with *E. coli* bacteria. In some embodiments, the density medium can have a density of between about 1.01 g/cm$^3$ and about 1.13 g/cm$^3$. In other embodiments, the density medium can have a density of between about 1.06 g/cm$^3$ and about 1.09 g/cm$^3$. In yet other embodiments, the density medium can have a density of between about 1.07 g/cm$^3$ and about 1.08 g/cm$^3$. The separation chamber 4143 can have any suitable depth as disclosed herein. For example, in some embodiments, the separation chamber 4143 can have a depth (also referred to herein as a thickness) of 0.250 mm or 0.125, or any value in between.

Figure 11:
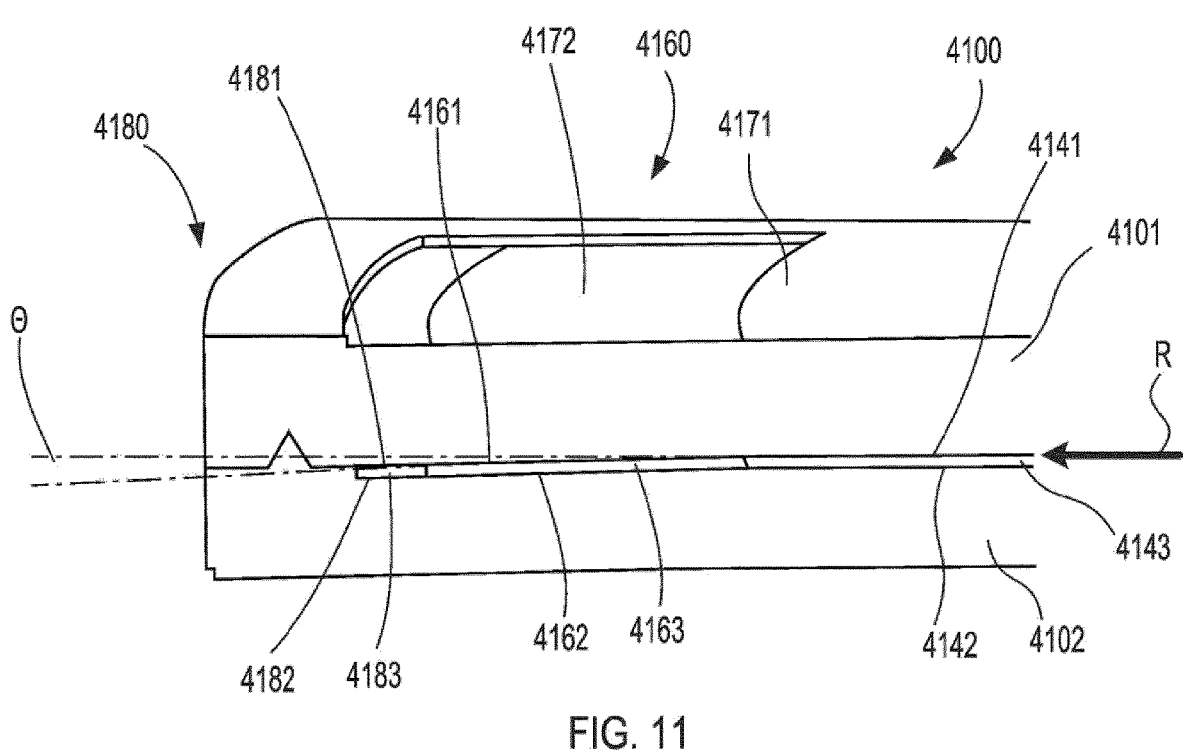
FIG. 11 is a cross-sectional view of a portion of the cartridge shown in FIGS. 9 and 10 taken along the line X-X in FIG. 9.
Figure 12:
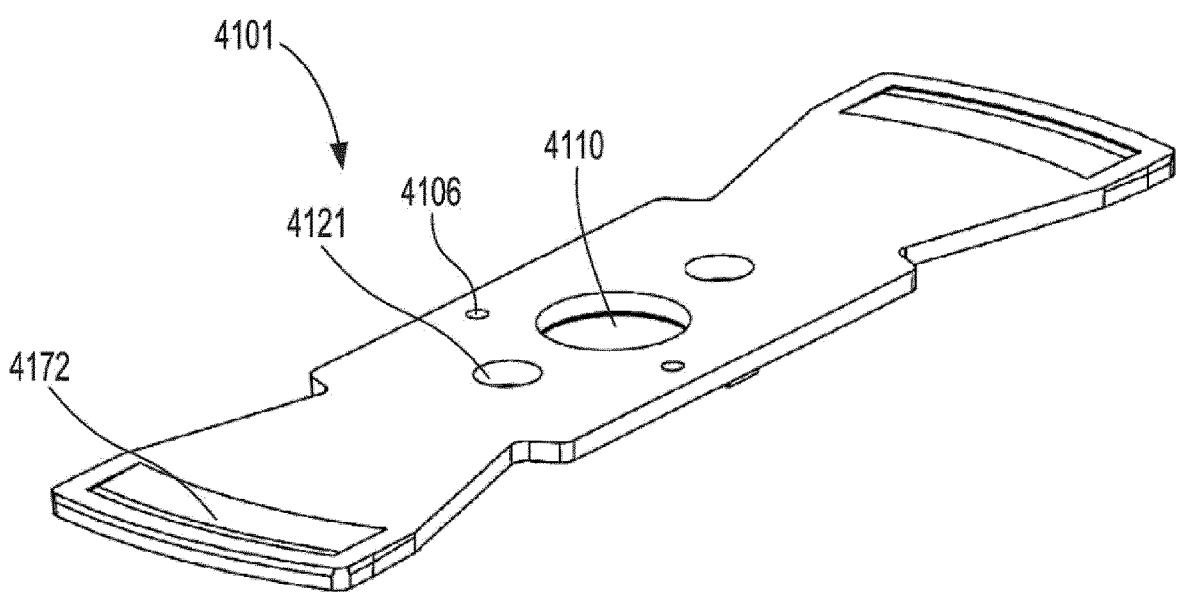
FIGS. 12 and 13 are perspective views of a top member of the cartridge shown in FIGS. 9 and 10, showing an outer surface (FIG. 12) and an inner surface (FIG. 13).
Figure 13:
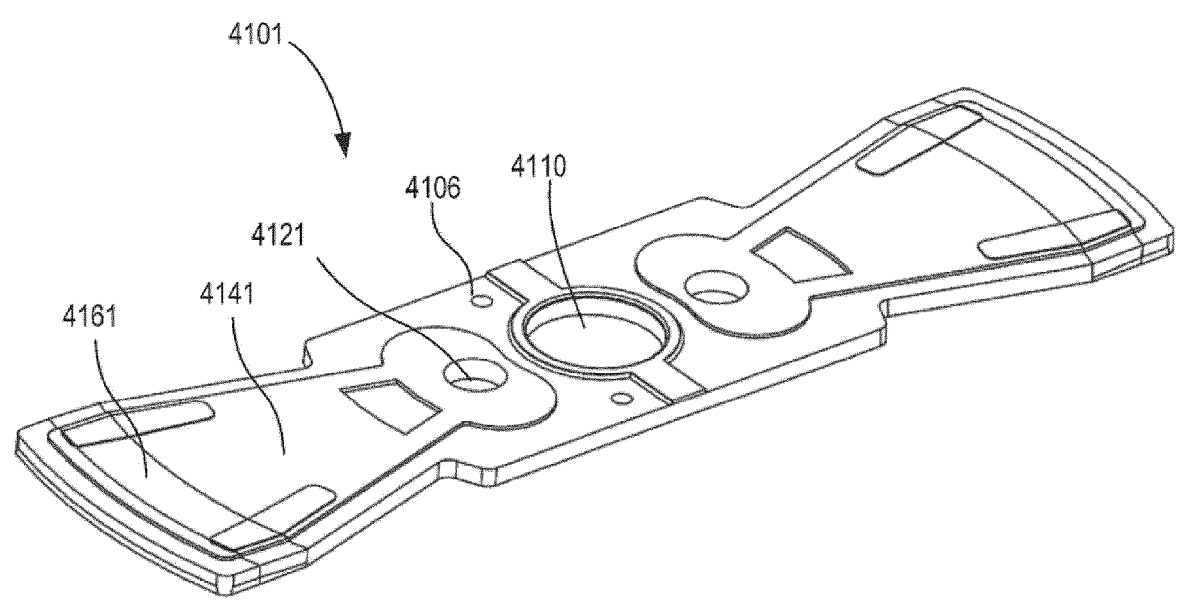
Figure 14:
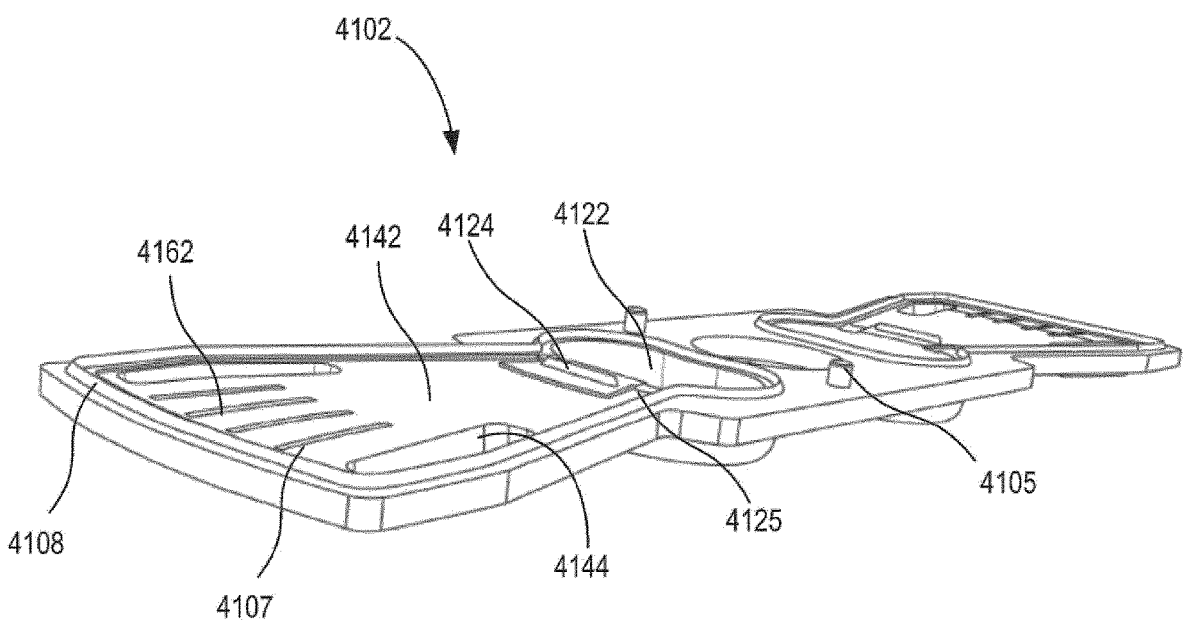
FIGS. 14 and 15 are top perspective views of a bottom member of the cartridge shown in FIGS. 9 and 10.

As shown in FIG. 11, the detection portion 4160 defines a detection chamber (or channel) 4163 that is bounded by a first surface 4161 (of the first member 4101) and a second surface 4162 (of the second member 4102). In some embodiments, the second surface 4162 can include the ribs 4107 that can limit or prevent bulk flow of a portion of the sample during a rotation cycle. In other embodiments, the second surface 4162 does not include such ribs. The first surface 4161 (also referred to as a detection surface or an imaging surface) is nonparallel to at least one of the first surface 4141 or the second surface 4142, which allows target particles (or cells) to impinge on the detection surface 4161, as described in detail herein. Similarly stated, referring to FIG. 11, the detection surface 4161 and the first surface 4141 of the separation portion 4160 form a non-zero detection angle Θ. The detection angle Θ is along the radial axis (the radial direction is identified by the arrow R) of the cartridge 4100, i.e., an axis that intersects an axis of rotation Arot of the cartridge in a radial direction. Specifically, the detection angle Θ is within a cross-sectional plane defined by the axis of rotation Arot and the radial axis Arad. In some embodiments, the detection angle Θ is between about 1 degree and about 8 degrees. In other embodiments, the detection angle Θ is between about 1.5 degrees and about 5 degrees. In yet other embodiments, the detection angle Θ is about 2 degrees. In some embodiments, the detection surface 4161 and the first surface 4141 are monolithically constructed, and the detection angle is the "bend" between the surfaces.

In some embodiments, the detection surface 4161 (and any of the detection surfaces described herein, including the detection surface 4161 described below) is configured to capture the target particles TP. For example, in some embodiments, the detection surface 4161 can be modified to enhance adhesion of the target particles TP. Such modifications can include, for example, a chemical modification, a surface coating, electrically charging the detection surface 4161, or a combination of these modifications. For example, in some embodiments, the detection surface 4161 (and any of the detection surfaces described herein, including the detection surface 4161 described below) can include a marking or texture that can assist in the identification of the boundaries for imaging. In other embodiments, the detection surface 4161 can be modified by Corona treatment (also referred to as air plasma treatment). This process disrupts the polymeric chains at the surface, which can increase the surface energy of the detection surface 4161, thereby improving improve the surface adhesion properties of the detection surface 4161. In other embodiments, the surface modification can include applying a charged coating, such as Poly-L-lysine (PLL) or Polyethylenimine, which will bind negatively charged particles (e.g., bacteria). In some embodiments, the charged polymer can include ($—NH_3^+$) for creating a positive surface charge. The charged coating can be applied in any suitable manner. In some embodiments, the charged polymer coating can be applied by attachment using carbodiimide compounds. Carbodiimide compounds are cross-linking compounds that can promote application of charged polymeric coatings, such as PLL. In other embodiments, the charged polymer coating can be applied by photochemically induced polymerization and grafting of the desired coating. Moreover, the detection surface 4161 can be modified using a combination of any suitable procedures to enhance the adhesion properties of the surface. For example, as shown in FIG. 18 (which references the detection surface 4161), any of the detection surfaces described herein, including the detection surface 4161 can be modified using a combination of Corona treatment and a PLL coating. The positive charge of the detection surface 4161 is shown by the (+), which improves the adhesion properties to capture the target particles (e.g., bacteria) therein.

In some embodiments, the detection surface 4161 can be modified to have a surface finish (or roughness) that is conducive to capturing the target particles TP. The surface finish (or roughness) can also be selected to provide identification and/or marking characteristics that do not interfere with imaging procedures. In this manner, the detection surface and other portions of the cartridge can include markings to assist in collection and evaluation of imaging data.

As shown, the detection angle Θ is in a downward direction. In this manner, the detection surface 4161 is on the first member 4101 that forms the cartridge 4100. Referring again to FIG. 11, an outer surface 4171 of the first member 4101 also includes an angled surface 4172 that, along with the detection surface 4161, defines the imaging (or optical) path through the first member 4101. The angle of the surface 4172 is the same as the detection angle Θ. Similarly stated, the outer surface 4172 is parallel to the detection surface 4161.

The detection chamber 4163 (see FIG. 11) can have any suitable depth as disclosed herein. For example, in some embodiments, the detection chamber 4163 can have a depth (also referred to herein as a thickness) of 0.250 mm or 0.125, or any value in between. In some embodiments, the depth of the detection chamber 4163 can be the same as the depth of the separation chamber 4143. In other embodiments, the depth of the detection chamber 4163 can be different from the depth of the separation chamber 4143.

Referring to FIG. 11, the waste portion 4180 defines a waste chamber (or channel) 4183 that is bounded by a first surface 4181 (of the first member 4101) and a second surface 4182 (of the second member 4102). In some embodiments, the first surface 4181 of the waste portion 4180 and the second surface 4142 of the separation portion 4140 are coplanar. In other embodiments, the first surface 4181 of the waste portion 4180 is lower than the second surface 4142 of the separation portion 4140. The waste chamber 4183 has a depth (also referred to herein as a thickness) of 0.250 mm or 0.125, or any value in between.

Figure 17:
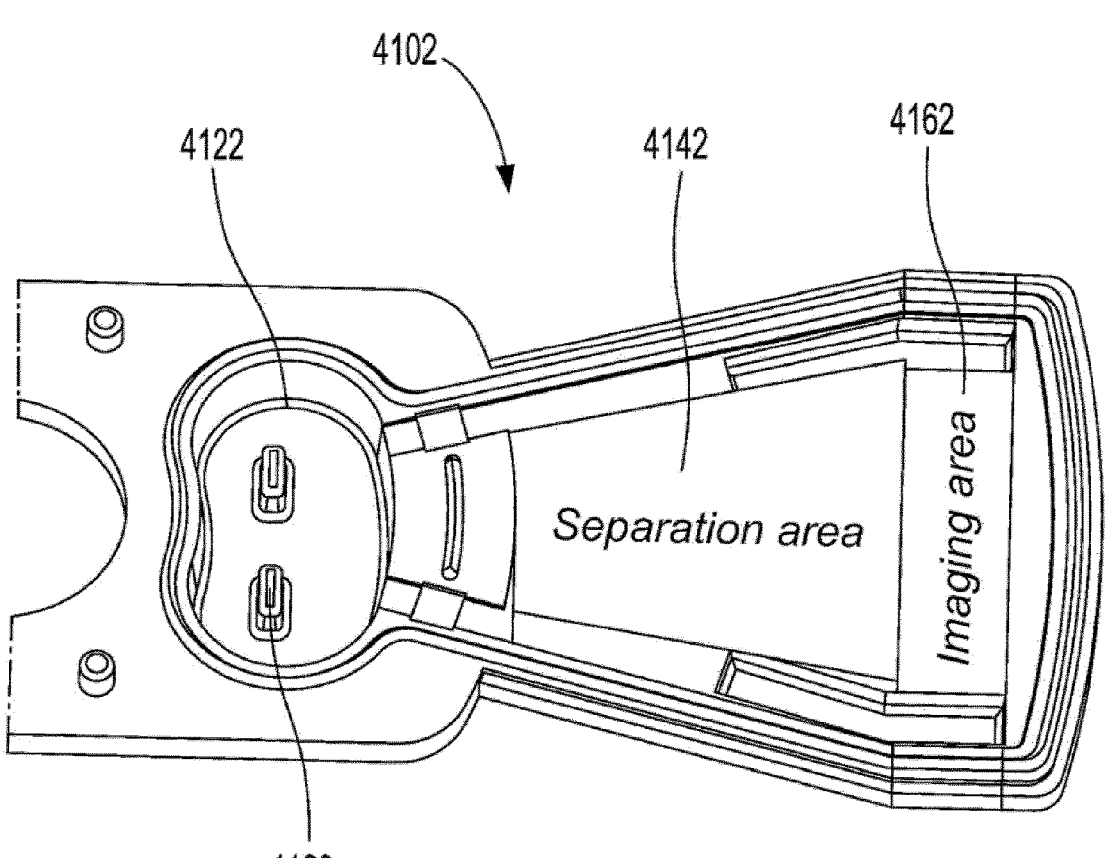
FIG. 17 is a top view of the bottom member of the cartridge shown in FIGS. 9 and 10, showing a separation portion and an imaging portion.
Figures 19, 20:
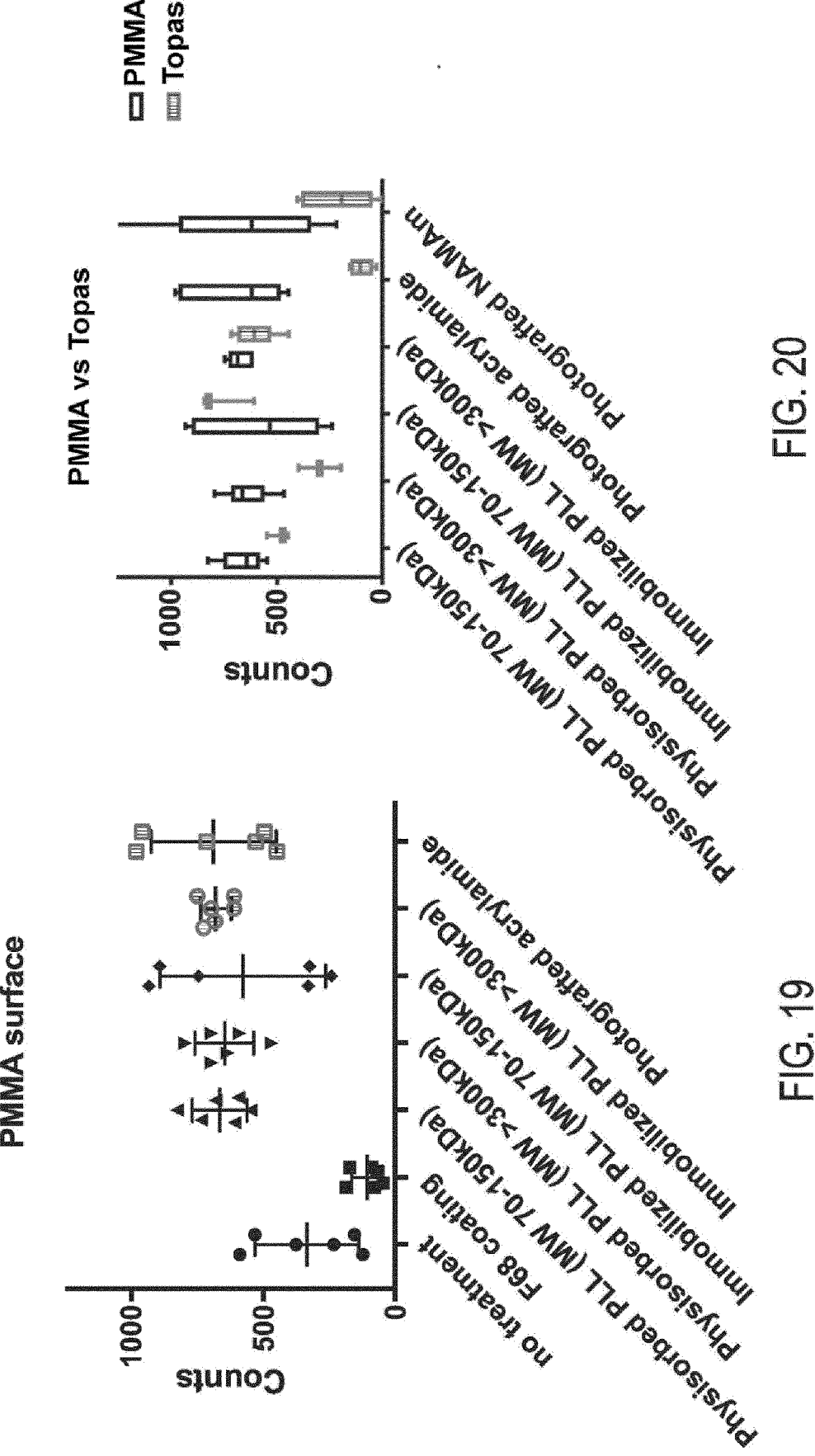
FIGS. 19 and 20 are graphs showing experimental data associated with surface treatments on a detection surface, according to an embodiment.

Referring to FIG. 17, the size (i.e., the surface area or volume) of the detection chamber 4163 and the size (i.e., the surface area or volume) of the separation chamber 4143 can be selected such that the concentration of the target particles captured on the detection surface 4161 is greater than the concentration of the target particles in the initial sample. Similarly stated, the size (i.e., the surface area or volume) of the detection chamber 4163 and the size (i.e., the surface area or volume) of the separation chamber 4143 can be selected to produce "up-concentrating" of the target particles within the detection chamber 4163. For example, in some embodiments, a ratio of a volume of the separation chamber 4143 and a volume of the detection chamber 4163 is at least about 2.0. In other embodiments, a ratio of a volume of the separation chamber 4143 and a volume of the detection chamber 4163 is at least about 2.5. Further, the volumes of the chambers can facilitate a desired volume ratio of the initial sample to the density medium within the cartridge 4100. For example, in some embodiments, the ratio of the sample volume to the volume of the density medium is about 100:45. Specifically, for a sample volume of 100 microliters the cartridge 4100 can contain about 45 microliters of density media is to ensure the detection chamber 4163 is fully filled with the density media. The ratio of density medium to inlet sample can also produce "up-concentrating" of the target particles within the detection chamber 4163. The cartridge 4100, including the first member 4101 and the second member 4102 can be constructed from any suitable materials. For example, in some embodiments, the cartridge 4100 can be constructed from polymethylmethacrylate (PMMA). In other embodiments, the cartridge 4100 can be constructed from cyclic olefin copolymers (COC), including such polymers manufactured by Topas® Advanced Polymers. Moreover, any of the materials from which the cartridge 4100 is formed can include the surface modifications to the detection surface 4161 described above. FIGS. 19 and 20 are graphs showing experimental data associated with surface treatments on the detection surface 4161 for cartridges formed from both PMMA and COC. As shown, there are many different possible methods for applying a charged coating to the detection surface 4161, and some of these methods are effective on either (or both) PMMA and COC. However, the surface treatment with a nonionic surfactant F68 does not enhance adhesion of bacteria to the detection surface.

Figure 22:
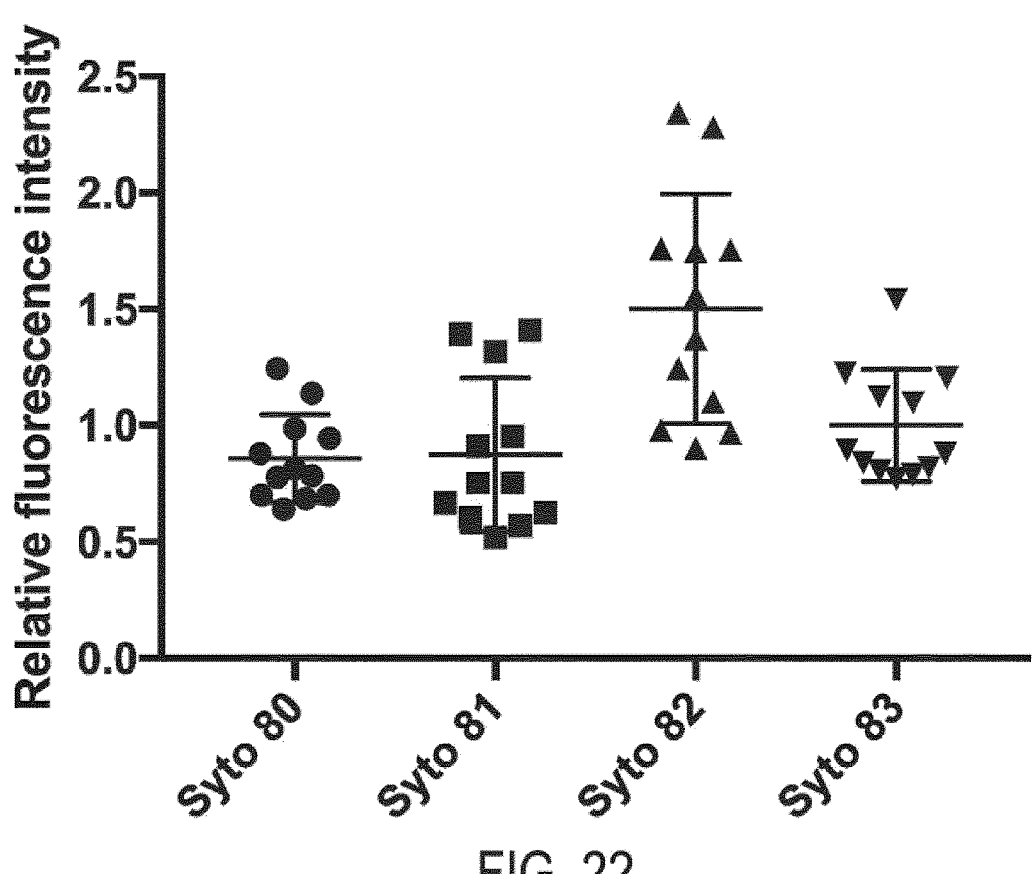
FIG. 22 is a graph showing experimental data associated with a staining reagent used in methods, according to an embodiment.

In some embodiments, the cartridge 4100 can contain a staining reagent within the inlet reservoir 4122 or in other portions of the cartridge. The staining reagent is formulated to bind to and enhance detection of the target cells. In this manner, the staining reagent can improve the specificity of detecting (e.g., imaging) target particles in samples containing contaminants. Specifically, where certain contaminants having a similar size, density and/or shape of the target particles are also captured on the detection surface 4161, the use of a staining reagent can allow for such contaminants to be distinguished from the target particles. In some embodiments, the staining reagent can include DNA dyes that are effective with both gram-positive organisms and gram-negative organisms. Such staining reagents can include ethylenediaminetetraacetic acid (EDTA) to promote disruption of the cell walls for gram negative organisms, thereby promoting equalization of the results. In some embodiments, the staining reagent can include any suitable Syto™ nucleic acid stains, including those shown in FIG. 22, which is a plot of experimental data associated with various staining reagents. In other embodiments, the staining reagent can include a DAPI fluorescent stain or Hoechst 33258. Such staining reagents can be used to label DNA within target cells (e.g., bacterial particles) while leaving platelets (which do not contain DNA) unstained.

In some embodiments, the staining reagent can be pre-packaged within the cartridge 4100 and can be mixed with the sample after the sample is introduced into the inlet reservoir 4122. For example, in some embodiments, the staining reagent can be stored within the inlet reservoir in a dry state (e.g., powdered or lyophilized) and can be reconstituted by the sample when the sample is added to the inlet reservoir. In other embodiments, the staining reagent can be stored within the inlet reservoir in a liquid state and the opening 4121 can be covered to prevent spillage during storage and shipment prior to use. In yet other embodiments, the cartridge 4100 can include one or more separate reagent reservoirs (not shown) within which the staining reagent can be contained. In use, the reagent reservoir can be placed in fluid communication (e.g., via a valve, a frangible seal being punctured or the like) with the inlet reservoir 4122 to allow mixing of the staining reagent with the biological sample.

In other embodiments, the staining reagent can be included as part of a kit that includes the cartridge 4100 (or any of the cartridges described herein) and all the necessary items for completing any of the methods described herein. Such kits are described in more detail below. In some embodiments, the cartridge 4100 can contain a dilution reagent within the inlet reservoir 4122 or in other portions of the cartridge. The dilution reagent is formulated to improve the properties of the biological sample to facilitate detection according to the methods described herein. For example, in some embodiments, the dilution reagent can include any of an antifoaming agent, a wetting agent, a dispersant, or an emulsifier. In some embodiments, the dilution reagent can include a poloxamer, such as the F-68 Pluronic. In some embodiments, the poloxamer can contain poly(ethylene oxide) (PEO) and poly(propylene oxide) (PPO). In some embodiments, the dilution reagent can include sodium azide. In some embodiments, the dilution reagent can be prepackaged within the cartridge 4100 and can be mixed with the sample after the sample is introduced into the inlet reservoir 4122. For example, in some embodiments, the dilution reagent can be stored within the inlet reservoir in a liquid state and the opening 4121 can be covered to prevent spillage during storage and shipment prior to use. In other embodiments, the cartridge 4100 can include one or more separate reagent reservoirs (not shown) within which the dilution reagent can be contained. In use, the reagent reservoir can be placed in fluid communication (e.g., via a valve, a frangible seal being punctured or the like) with the inlet reservoir 4122 to allow mixing of the dilution reagent with the biological sample.

In other embodiments, the dilution reagent can be included as part of a kit that includes the cartridge 4100 (or any of the cartridges described herein) and all the necessary items for completing any of the methods described herein. Such kits are described in more detail below. Although described as including separate reagents and/or constituents, such as a staining reagent, a dilution reagent, and a density medium, in some embodiments, certain compositions and/or functions of one of these constituents can be performed by any of the other constituents. For example, in some embodiments, the density medium can include a poloxamer, such as the types described above.

As described above with respect to the cartridge 2100, the sample can include first, low-density portion and a second, higher-density portion. The first portion can include the low-density contaminants, such as, unbound dyes (staining reagent), cell fragments, proteins, or other matrix components. The second portion can initially include the target particles, as well as other high-density contaminants, such as red blood cells, leukocytes, crystals, or large protein aggregates. In use, the effective centrifugal force causes the target particles and high-density contaminants to migrate in the radially outward direction. The target particles will migrate until they contact the detection surface 4161. Low-density contaminants, however, are retained in the separation portion 4140 (e.g., being blocked by the density medium) and are therefore prevented from reaching the detection surface 4161.

Figures 24A, 24B:
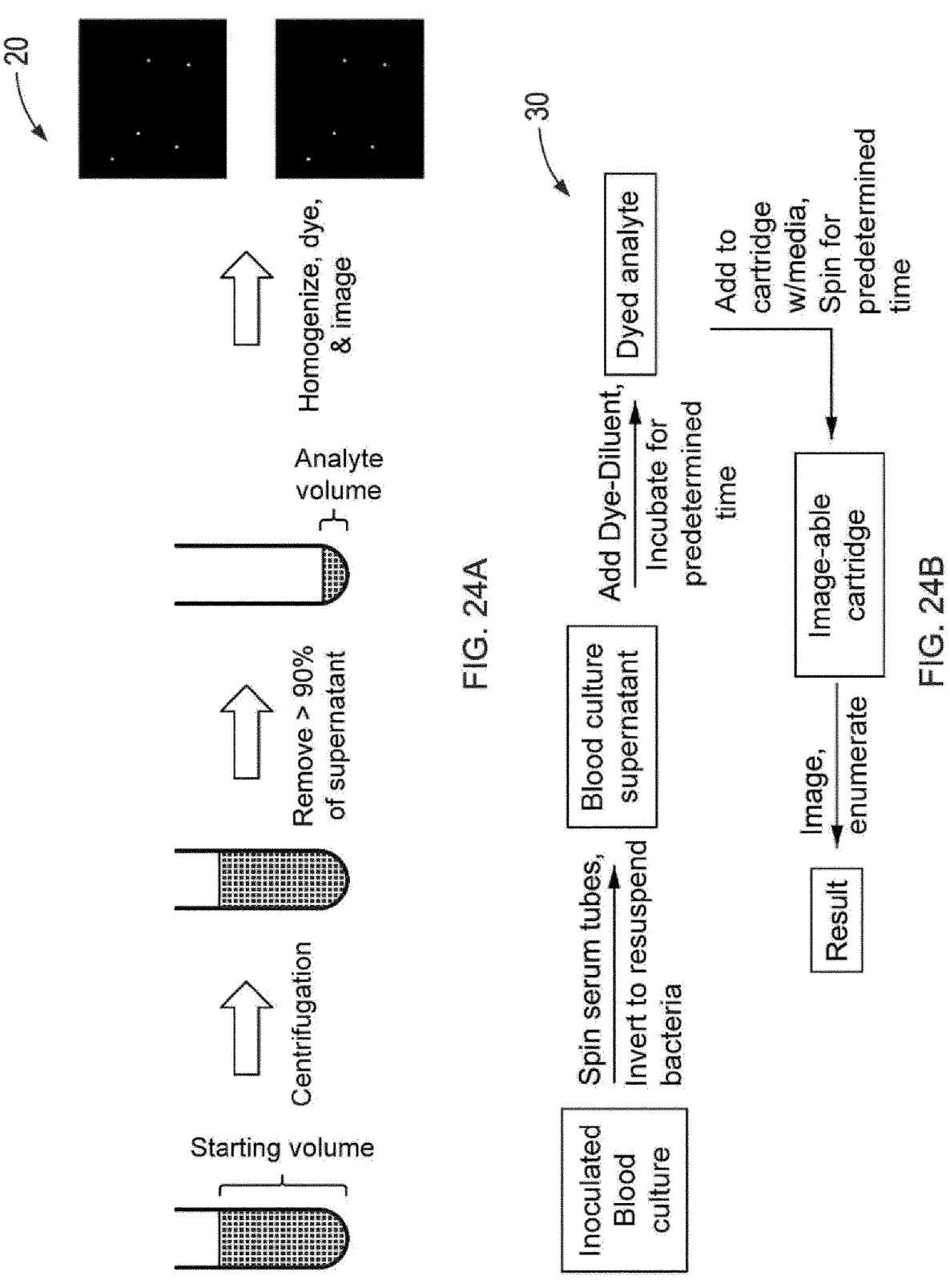
FIGS. 24A and 24B are schematic illustrations showing methods of detecting a concentration of target cells within a sample, according to embodiments.

FIG. 23 is a flow chart of a method 10 of detecting a concentration of target cells within a sample, according to an embodiment. In some embodiments, the method 10 (and the cartridges described herein) can determine the concentration of the target cells within a lower limit of 10ˆ3 colony forming units (CFU) per milliliter (mL) and an upper limit of 10ˆ9 CFU per mL. In other embodiments, the lower limit is 10ˆ3 colony forming units (CFU) per milliliter (mL). Although described in connection with the cartridge 4100, the method 10 can be performed using any of the cartridges, systems, and/or components described herein. Moreover, the method 10 can be included as part of other methods for determining treatment protocols or the like. In some embodiments, the method can optionally include processing the raw biological sample to produce a sample that is suitable for use within the cartridge 4100. Specifically, the method 10 can optionally include processing a raw cultured blood sample to produce a sample suitable for input into an inlet reservoir 4122 of the cartridge 4100, at operation 12. Examples of suitable sample preparation are depicted in FIGS. 24A and 24B, which show sample preparation methods 20 and 30 that include an initial centrifugation.

The method also optionally includes mixing a staining reagent with sample, at operation 13. The staining reagent can be any of the staining reagents described herein and is formulated to bind to and enhance detection of the target cells. As described above, in some embodiments, the staining reagent can be stored within the cartridge and the mixing can occur within the inlet reservoir after the sample is conveyed into the reservoir. In other embodiments, the staining reagent can be stored separately from the cartridge and can be added to the sample either outside of the cartridge or after the sample is in the inlet reservoir.

The method includes conveying the sample into an inlet reservoir of a cartridge, at operation 14. The cartridge can be similar to the cartridge 4100 and includes a separation portion and a detection portion. The separation portion includes a first surface and a second surface defining a separation chamber that can be fluidically coupled to the inlet reservoir (e.g., via either a passive or active valve). The detection portion includes a detection surface that forms a boundary of a detection chamber. The detection chamber is fluidically coupled to the separation chamber, and the detection surface and the first surface of the separation portion form a non-zero detection angle. The detection surface is configured to capture the target cells.

The cartridge is coupled to a rotation element of an instrument, at 16. The instrument can be any of the instruments described herein. The instrument is then actuated at operation 18 to cause the instrument to perform the separation and detection functions. Specifically, after actuation, the instrument rotates the cartridge at a rotation speed sufficient to cause at least a portion of the sample to flow, be conveyed, or otherwise move from the inlet reservoir through the separation chamber and into the detection chamber, and the target cells to be captured on the detection surface, at operation 18A. In some embodiments, the cartridge can include a density medium of the types described herein to facilitate separation of the sample to isolate the target cells.

The rotation speed and time can be any suitable time to cause the target cells to be captured by the detection surface. For example, in some embodiments, the rotation speed can be maintained for at least one minute, at least two minutes, at least three minutes, and at least five minutes. In some embodiments, the rotation speed can be at least 3000 RPM. In other embodiments, the rotation speed can be between about 3000 RPM and about 15,000 RPM. In other embodiments, the rotation speed can be between about 5000 RPM and about 9000 RPM. In yet other embodiments, the rotation speed can be between about 6000 RPM and about 7000 RPM.

The instrument then receives, via a detector of the instrument, a signal indicating a quantity of the target cells captured on the detection surface, at operation 18B. The detector can be any suitable detector. For example, in some embodiments, the detector is an optical detector and the signal is a light (optical) signal. The instrument then determines, based on the signal, the concentration of the target cells in the sample, at operation 18C.

In some embodiments, the instrument can include a processor, a memory, and other electronic components to perform any portion of the method 10 (and any other methods described herein). The processor of the instrument can be configured to run and/or execute application modules, processes and/or functions associated with the instrument. For example, the processor can be configured to run and/or execute an image capture module that facilitates capturing and processing of an image produced during the method 10. The processor can be, for example, a Field Programmable Gate Array (FPGA), an Application Specific Integrated Circuit (ASIC), a Digital Signal Processor (DSP), and/or the like. The processor can be configured to retrieve data from and/or write data to a memory device (not shown).

The memory (not shown) can be, for example, random access memory (RAM), memory buffers, hard drives, databases, erasable programmable read only memory (EPROMs), electrically erasable programmable read only memory (EEPROMs), read only memory (ROM), flash memory, hard disks, floppy disks, cloud storage, and/or so forth. In some embodiments, the memory stores instructions to cause the processor to execute modules, processes and/or functions associated the instrument. For example, the memory can store instructions to cause the processor to execute the image capture module.

In some embodiments, any of the methods, cartridges, and kits for detecting a concentration of target cells within a sample can be used as part of an assay to determine susceptibility of the target cells to a treatment protocol. For example, in some embodiments, any of the methods, cartridges, and kits for detecting a concentration of target cells can be used as part an antibiotic susceptibility test (AST).

For example, FIG. 25 is a flow chart of a method 40 of determining susceptibility of target cells to a treatment protocol, according to an embodiment. The method includes conveying a first portion of the sample into a cartridge, at operation 41. The cartridge can be similar to the cartridge 4100 and includes a separation portion and a detection portion. The separation portion includes a first surface and a second surface defining a separation chamber. The detection portion includes a detection surface that forms a boundary of a detection chamber. The detection chamber is fluidically coupled to the separation chamber, and the detection surface and the first surface of the separation portion form a non-zero detection angle. The detection surface is configured to capture the plurality of target cells.

The cartridge is then coupled within a first instrument. The first instrument is actuated, at operation 42, to cause the instrument to perform several functions. The first instrument rotates the cartridge at a rotation speed sufficient to cause the first portion of the sample to flow, be conveyed, or otherwise move through the separation chamber and into the detection chamber, and the target cells to be captured on the detection surface, at operation 42A. The instrument then receives, via a detector of the instrument, a signal indicating a quantity of the target cells captured on the detection surface, at operation 42B. Finally, the first instrument then determines, based on the signal, the concentration of the target cells in the sample, at operation 42C. The method further includes processing, based on the concentration of the target cells within the first portion of the sample, a second portion of the sample, at operation 43. The processing can include, for example, diluting the second portion of the sample to ensure that the concentration of the target cells is within a desired range. The second portion of the sample is then conveyed into a reaction chamber, at 44. The method then includes actuating a second instrument to perform a susceptibility assay on the second portion of the sample to determine susceptibility of the target cells to the treatment protocol, at operation 45.

In some embodiments, a kit includes a cartridge of the types shown and described herein, as well as other materials for performing any of the methods described herein. For example, in some embodiments, a kit can include a cartridge (e.g., the cartridge 4100) and any of the reagents and/or density media described herein. In some embodiments, a predetermined amount of the density medium (e.g., an amount sufficient to fill the cartridge to the desired level without overfilling) can be packaged in a container separate from the cartridge. In some embodiments, a volume of the density medium can be less than fifty percent of the volume of the cartridge. In some embodiments, a predetermined amount of either or both of a dilution reagent (e.g., an amount sufficient to fill the cartridge to the desired level without overfilling) or a staining reagent (e.g., an amount sufficient to produce the desired staining of the target particles) can be packaged in a container separate from the cartridge. In some embodiments, the staining reagent and the dilution reagent can be stored together in a single reagent container. In other embodiments, each composition (e.g., density medium, dilution reagent, staining reagent) can be stored in a separate container. By packaging the density medium, the reagents, and the cartridge separately, the kit may have an extended shelf life. Additionally, if certain assays require one density medium or reagent and other assays require a second, different density medium or a second, different reagent, separately packaging the density medium, reagents and the cartridge can allow for the same cartridge to be used in different kits (each with different reagents, density media, or the like).

In some embodiments, the kit can include a sample transfer device (e.g., a pipette) and/or other items for sample handling. For example, in some embodiments, the kit can include a pipette and a mixing or sample handling container. In use, the sample can be mixed with either or both of the dilution reagent and the staining reagent within the mixing container. The pipette can be used to convey a predetermined amount of the desired reagent from a storage container into the mixing container. The pipette can also be used to transfer the sample into the mixing container, and also aspirate or mix the constituents. Finally, the pipette can transfer the mixture of the sample and reagent from the mixing container to the cartridge.

Additional elements in some embodiments include a vapor-resistant material such as an adhesive foil over the inlet hole(s). A cartridge may have an extended shelf life by storing it in a secondary sealed pouch. For bio safety, the inlet hole(s) may be covered during spinning.

In other embodiments, however, the kit can include a cartridge that is pre-filled with the density medium and/or any of the reagents described herein.

Figure 26A:
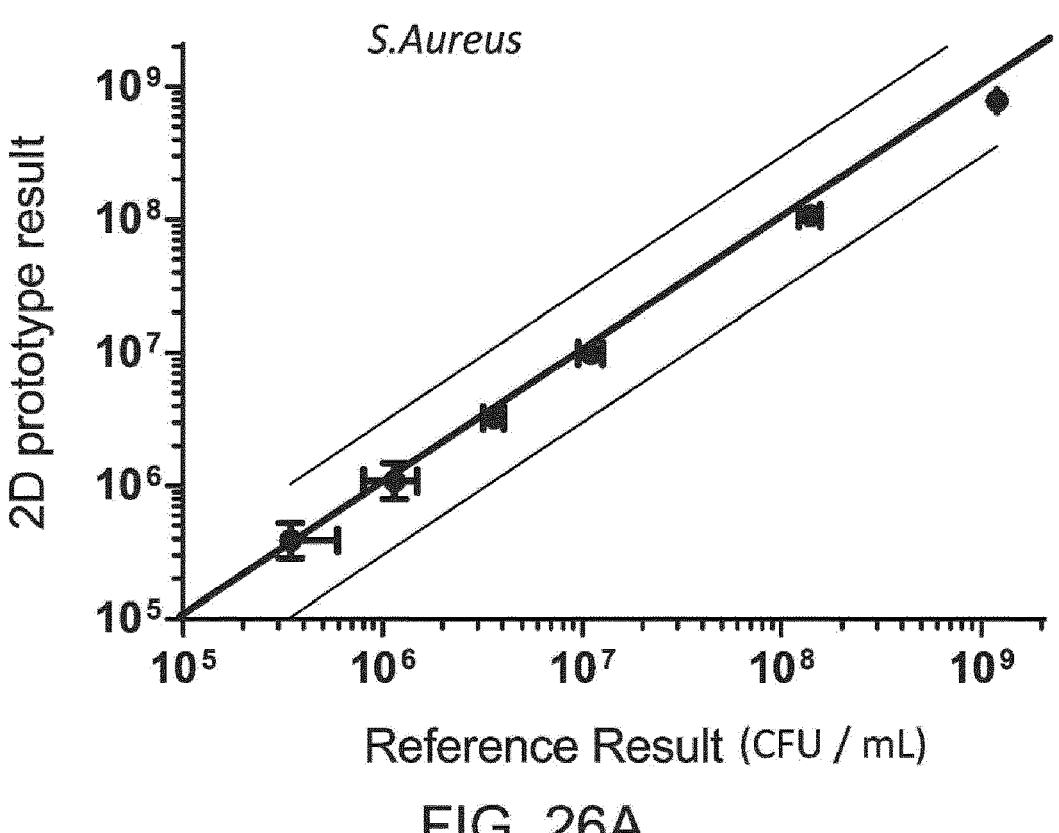
FIGS. 26A and 26B are graphs showing experimental data of cell concentration associated with cartridges and methods, according to various embodiments.
Figure 26B:
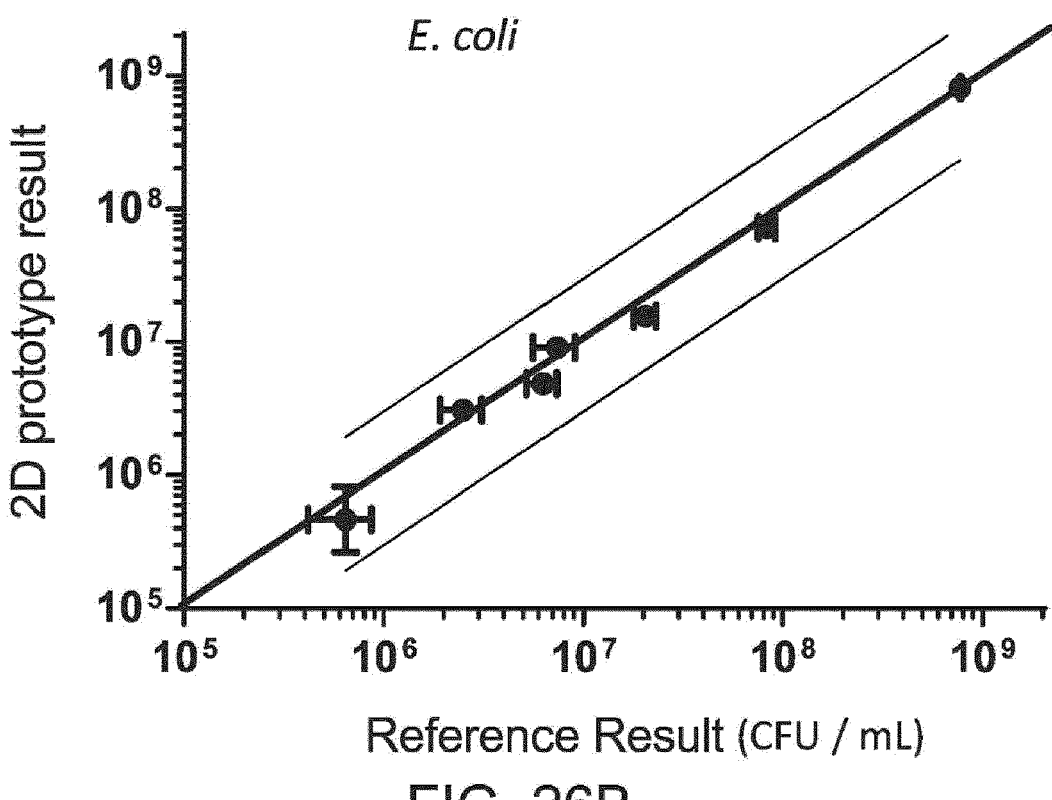

FIGS. 26A and 26B are graphs showing experimental data of cell concentration associated with cartridges and methods, as described herein. These data show correlation between a reference sample and test results performed on a two-dimensional prototype cartridge (the 2D cartridge). The 2D cartridge includes a single, parallel channel through which the sample is conveyed during a rotation cycle. The effect of the angled detection surface is simulated in the 2D cartridge by orienting the cartridge at a non-zero angle with respect to the radial axis. In these tests, the reference sample included bacteria (S. *Aureus* or *E. coli*) spiked into a blood culture supernatant (containing blood and media). The reference result was obtained by using hemocytometry. These results show feasibility of the cartridges and methods described herein to determine cell concentration with a lower limit of detection of about 10^5 CFU/mL and an upper limit of about 10^9 CFU/mL.

Figure 27:
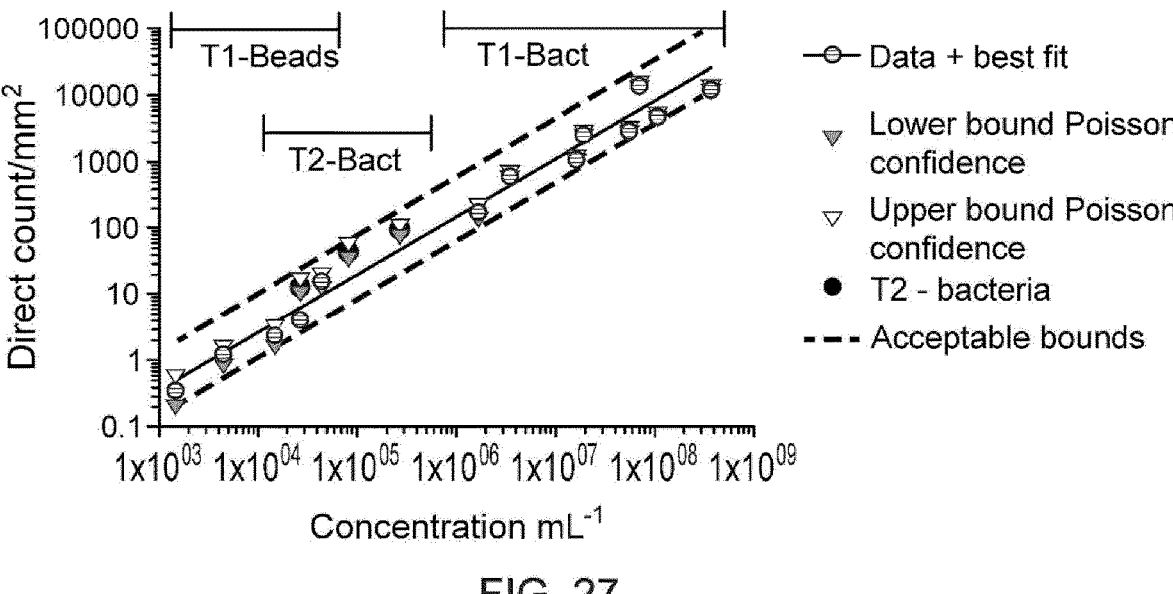
FIG. 27 is a graph showing experimental data of particle concentration associated with cartridges and methods, according to various embodiments.

FIG. 27 is a graph showing experimental data of particle concentration associated with cartridges and methods, as described herein. Specifically, FIG. 27 shows experimental data of particle concentration with different particles from tests performed on a cartridge of the types shown and described herein. Specifically, the test cartridge included a separation surface and a detection surface that form a non-zero detection angle. The reference samples for the results shown in FIG. 27 include both simulation beads (that were 1 μm, fluorescent beads), for the lower concentration range and bacteria for the higher concentration range. These results show feasibility of the cartridges and methods described herein to determine cell concentration with a lower limit of detection of about 10^3 CFU/mL and an upper limit of about 10^9 CFU/mL.

Figure 28:
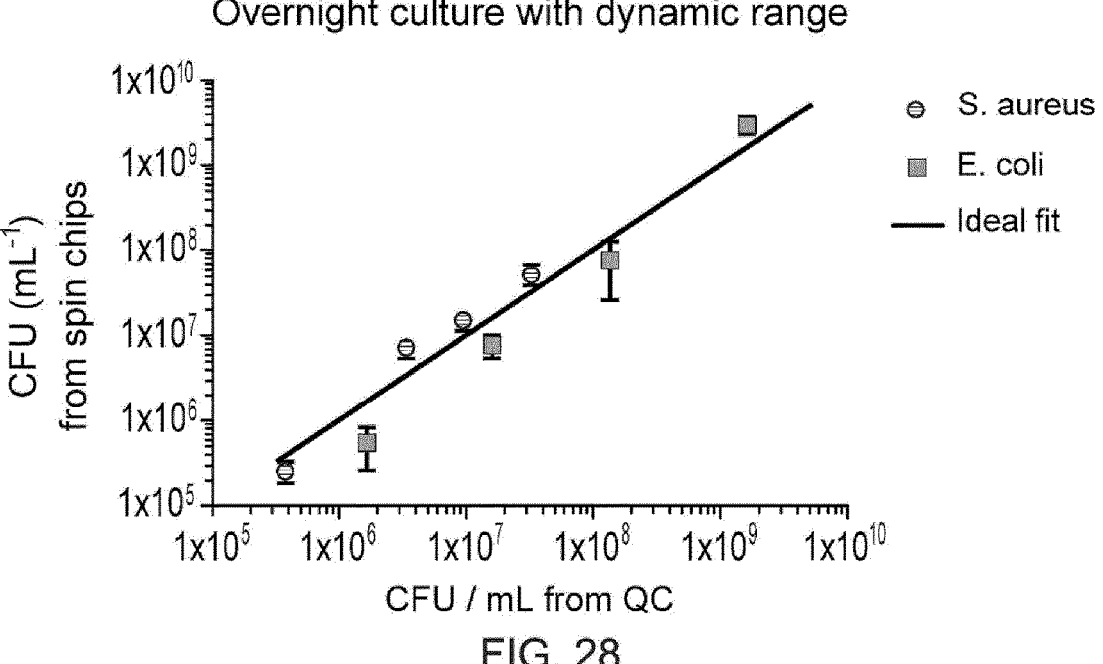
FIG. 28 is a graph showing experimental data of bacteria cell concentration associated with cartridges and methods, according to various embodiments.

FIG. 28 is a graph showing experimental data of both staph cell (*S. aureus*) and *E. coli* concentration associated with cartridges and methods, as described herein.

Figure 29A:
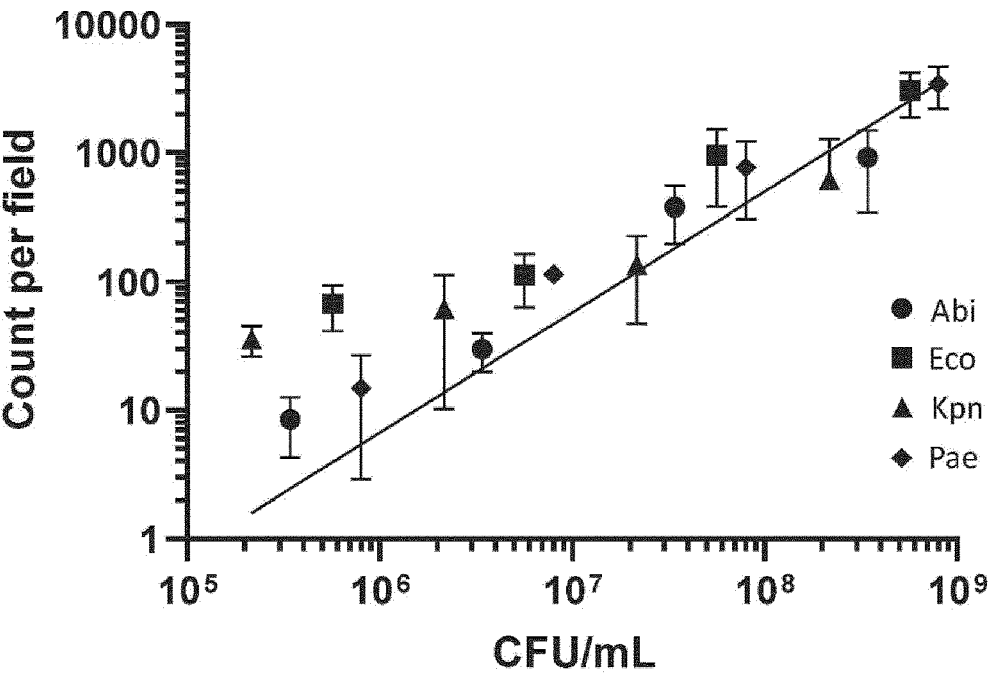
FIGS. 29A and 29B are graphs showing experimental data of bacteria cell concentration associated with cartridges and methods, according to various embodiments.
Figure 29B:
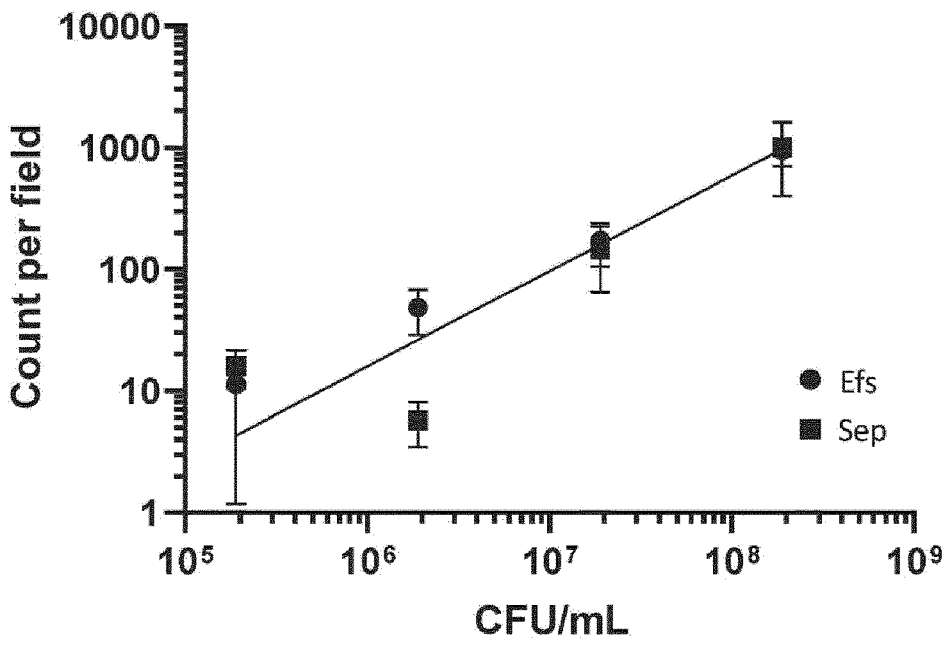

FIGS. 29A and 29B are graphs showing experimental data of particle concentration associated with cartridges and methods, as described herein. Specifically, FIG. 29A shows a correlation curve for gram negative species, including *Acinetobacter baumannii* (indicated as Abi), *Escherichia coli*(indicated as Eco), *Klebsiella pneumoniae* (indicated as Kpn), and *Pseudomonas aeruginosa* (indicated as Pae). FIG. 29B shows a correlation curve for gram positive species, including *Enterococcus faecalis* (indicated as Efs) and

*Staphylococcus epidermidis* (indicated as Sep). These results were produced using an overnight culture procedure that included inoculating bacteria in 1:4 whole blood and blood culture media mixture. The samples were incubated overnight at 37° C., with shaking. The overnight culture was then centrifuged in a serum separator at 3000 rpm for 10 minutes. The serum separator tube was then vortexed to resuspend the bacteria prior to conveying the sample to the cartridge (similar to the cartridge 4100).

Figure 30A:
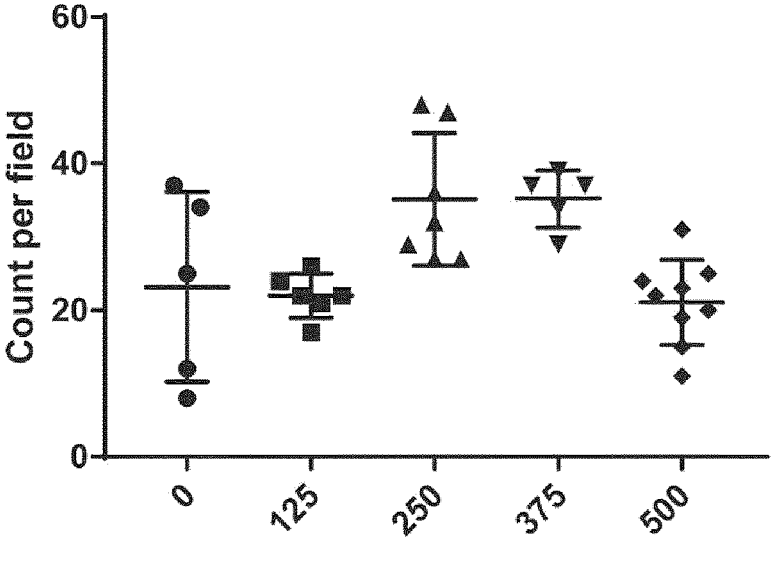
FIGS. 30A-30C are graphs showing experimental data of interference of bilirubin (FIG. 30A), lipids (FIG. 30B), and hemoglobin (FIG. 30C) associated with cartridges and methods, according to various embodiments.
Figure 30B:
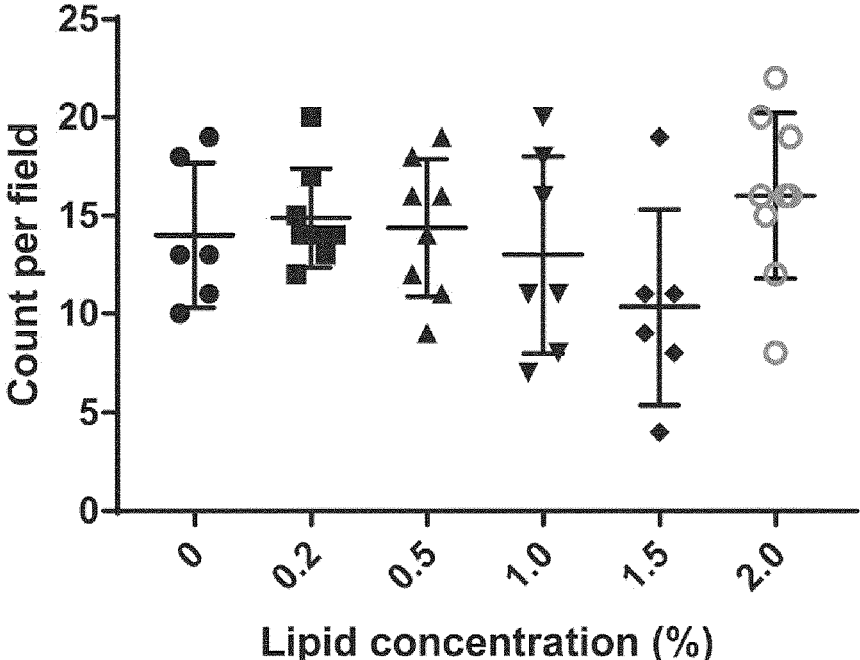
Figure 30C:
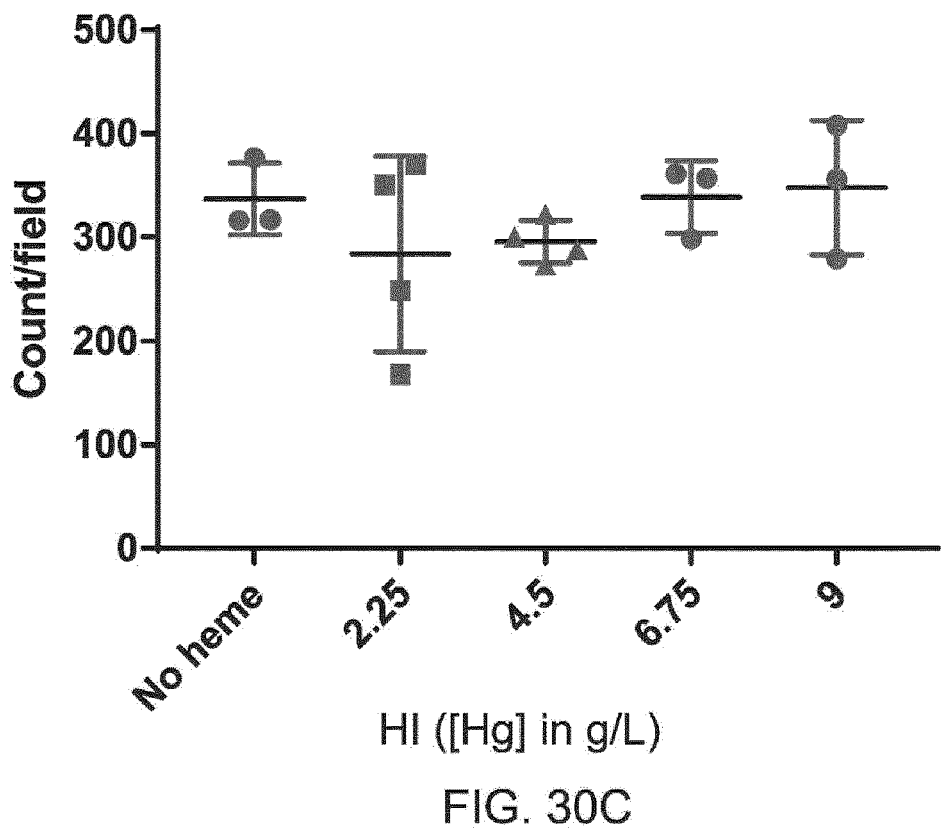

FIGS. 30A-30C are graphs showing experimental data of interference of bilirubin (FIG. 30A), lipids (FIG. 30B), and hemoglobin (FIG. 30C) associated with cartridges and methods, as described herein.

Figure 31:
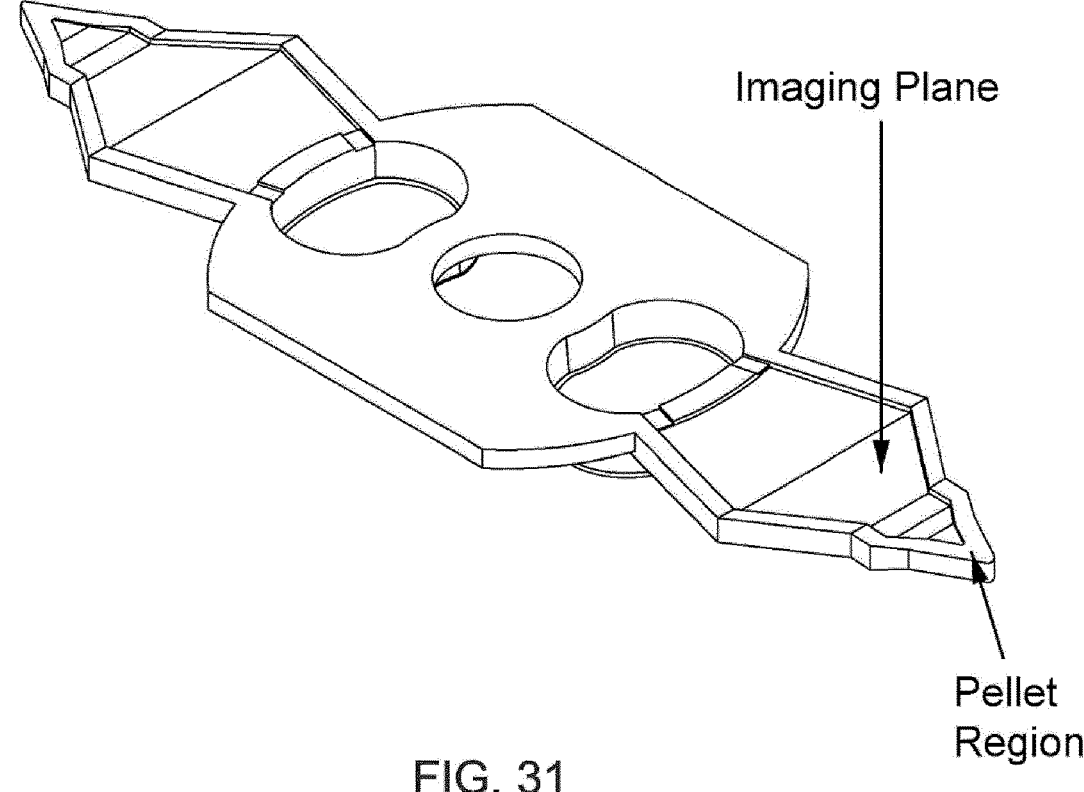
FIG. 31 is a perspective view of a cartridge, according to an embodiment.

FIG. 31 is a perspective view of a cartridge, according to an embodiment.

Figures 32A, 32B:
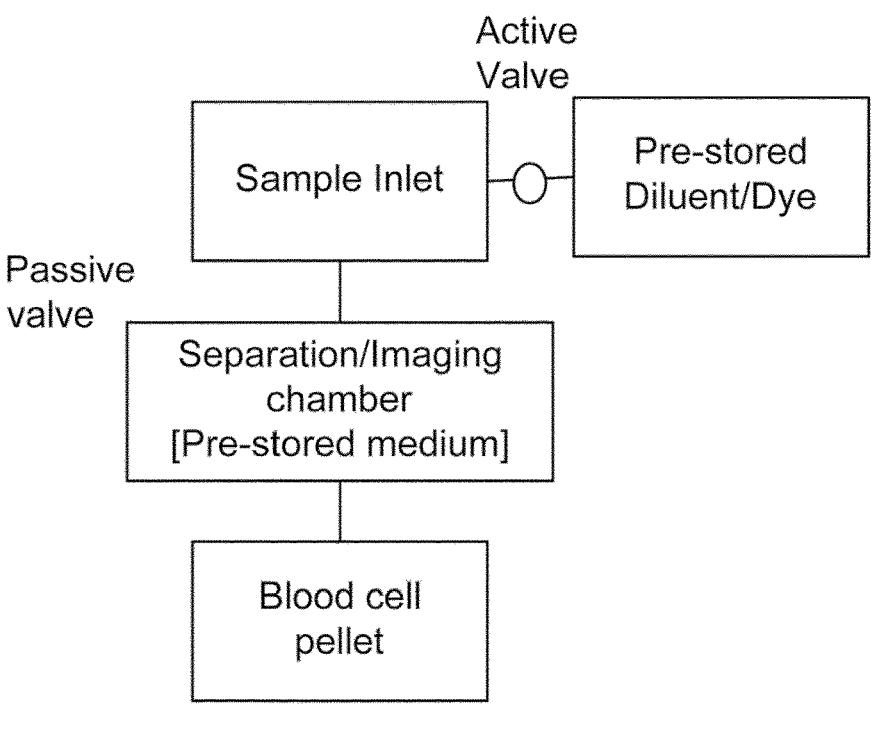
FIGS. 32A and 32B are schematic illustrations cartridges, according to various embodiments.

FIGS. 32A and 32B are schematic illustrations cartridges, according to various embodiments.

While various embodiments have been described above, it should be understood that they have been presented by way of example only, and not limitation. Where methods and/or schematics described above indicate certain events and/or flow patterns occurring in certain order, the ordering of certain events and/or operations may be modified. While the embodiments have been particularly shown and described, it will be understood that various changes in form and details may be made.

Any of the cartridges described herein can be manufactured according to any suitable process. For example, in some embodiments, the top plate and bottom plate of a cartridge may be assembled using ultrasonic welding, adhesive, press-fit, or by other means.

In some embodiments, any of the cartridges described herein can include removable or permanent seals, markings, handling accessories, and the like.

Some embodiments include a symmetrical cartridge, where both ends of the cartridge are functional, although not necessarily identical. For example, different ends of the cartridge may contain different density media, different dyes, different charged surfaces, and the like. Embodiments also include cartridges with only a single functional end. For these, the other end may be viewed as primarily a counterweight. Weight balance within a cartridge may be selected so the cartridge is balanced prior to spin, during spin, or after spin. In one embodiment, the cartridge is balanced for after spin.

Some embodiments include an instrument that uses the same motor to spin the cartridge to also position the cartridge within the imaging system so that the imaging system may image multiple, different locations at the end of the cartridge. That is, only a single motor is used for both spin and for positioning the cartridge during imaging phases of a system.

Any of the methods described herein can be performed on any suitable biological sample. The biological sample can include bodily fluids, such as blood, urine, a nasal swab, a vaginal swab, or the like. In some embodiments, the sample can be a blood culture.

Any of the methods described herein can be performed to detect any suitable target particles. In some embodiments, the target particles can include cells. Further, in some embodiments, the target cells can include bacteria cells. As such, the methods described herein can be used in conjunction with an assay to determine the susceptibility of the bacteria cells to treatment by a course of antibiotics. The target bacteria can include, for example, Enterobacteriaceae spp, *Pseudomonas* spp, *Acinetobacter* spp, *Staphylococcus* spp, *Streptococcus* spp, or *Enterococcus* spp.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices.

Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code. Although various embodiments have been described as having particular features and/or combinations of components, other embodiments are possible having a combination of any features and/or components from any of embodiments as discussed above. Aspects have been described in the general context of determining concentration of cells, and particularly bacteria cells, but inventive aspects are not necessarily limited to use in molecular diagnostics, health care, and/or medical devices.

The invention claimed is:

1. An apparatus, comprising:
a cartridge configured to be removably coupled to a rotation element configured to rotate the cartridge about a rotation axis to capture a plurality of target cells within a sample, the cartridge comprising:
an inlet portion defining an inlet reservoir configured to contain the sample;
a separation portion including a first surface and a second surface defining a separation chamber, the separation portion configured to contain a density medium having a density greater than a density of a first portion of the sample and less than a density of a second portion of the sample, the second portion including the plurality of target cells, the separation chamber configured to be fluidically coupled to the inlet reservoir such that at least the second portion of the sample can pass from the inlet reservoir to the separation chamber when the cartridge is rotated, wherein the first surface and the second surface are parallel to each other, the first surface and the second surface each being perpendicular to a distance between the first surface and the second surface; and
a detection portion including a detection surface that forms a boundary of a detection chamber, the detection chamber fluidically coupled to the separation chamber such that at least the plurality of target cells can pass through the density medium and into the detection chamber, the detection surface being non-parallel to at least one of the first surface or the second surface such that the plurality of target cells impinge on the detection surface when passing into the detection chamber, the first surface and the detection surface forming a single bend between the first surface and the detection surface, the single bend producing a non-smooth transition from the first surface to the detection surface and defining a detection angle of between about 1 degree and about 8 degrees, the detection surface configured to capture the plurality of target cells; and
a dilution reagent, wherein at least one of the dilution reagent or the density medium comprise any of an antifoaming agent, a wetting agent, a dispersant, or an emulsifier.

2. The apparatus of claim 1, wherein:
the distance between the first surface and the second surface is perpendicular to an axis that intersects a central location of the cartridge in a radial direction;
the inlet portion defines an opening through which the sample can be conveyed into the inlet reservoir; and
the detection surface is angled in a downward direction with respect to the opening and bends in a downward direction with respect to the axis that intersects the central location of the cartridge in the radial direction.

3. The apparatus of claim 1, wherein a ratio of a volume of the separation chamber and a volume of the detection chamber is at least about 2.0.

4. The apparatus of claim 1, wherein the distance between the first surface and the second surface defines a thickness of the separation chamber, the thickness of the separation chamber being less than about 0.6 mm.

5. The apparatus of claim 1, further comprising the density medium, the density medium having a density of between 1.01 g/cm3 and 1.13 g/cm3, and wherein the cartridge includes a density medium reservoir fluidically coupled to the separation chamber.

6. The apparatus of claim 1, wherein at least one of the dilution reagent or the density medium comprises a poloxamer, the poloxamer containing poly(ethylene oxide) (PEO) or poly(propylene oxide) (PPO).

7. The apparatus of claim 1, further comprising a staining reagent, the staining reagent formulated to bind to and enhance detection of the plurality of target cells.

8. The apparatus of claim 1, wherein:
the cartridge further comprises a collection portion including a third surface;
the detection surface is an upper surface of the detection portion, the detection surface transitioning into the third surface where the detection portion terminates in the collection portion;
the second surface is a bottom surface of the separation portion; and
the third surface is coplanar with or lower than the second surface.

9. An apparatus, comprising:
a cartridge configured to be removably coupled to a rotation element configured to rotate the cartridge about a rotation axis to capture a plurality of target cells within a sample, the cartridge comprising:
an inlet portion defining an inlet reservoir configured to contain the sample;
a separation portion including a first surface and a second surface defining a separation chamber, the separation portion configured to contain a density medium having a density greater than a density of a first portion of the sample and less than a density of a second portion of the sample, the second portion including the plurality of target cells, the separation chamber configured to be fluidically coupled to the inlet reservoir such that at least the second portion of the sample can pass from the inlet reservoir to the separation chamber when the cartridge is rotated; and
a detection portion including a detection surface that forms a boundary of a detection chamber, the detection chamber fluidically coupled to the separation chamber such that at least the plurality of target cells can pass through the density medium and into the detection chamber, the detection chamber being characterized by a substantially constant or diverging cross-sectional area, the detection surface being nonparallel to at least one of the first surface or the second surface such that the plurality of target cells impinge on the detection surface when passing into the detection chamber, the detection surface being angled at a non-zero angle with respect to a radial axis defined by the cartridge that is normal to the rotation axis, the detection surface configured to capture the plurality of target cells; and
a dilution reagent, wherein at least one of the dilution reagent or the density medium comprise any of an antifoaming agent, a wetting agent, a dispersant, or an emulsifier.

10. The apparatus of claim 9, wherein:
the first surface and the detection surface form a single bend between the first surface and the detection surface, the single bend defining a detection angle and producing a non-smooth transition from the first surface to the detection surface; and
the detection angle is between about 1 degree and about 8 degrees.

11. The apparatus of claim 10, wherein:
the detection angle is along the radial axis and within a cross-sectional plane defined by the radial axis and the rotation axis; and
the first surface of the separation portion and the detection surface are monolithically constructed.

12. The apparatus of claim 10, wherein the detection angle is about 2 degrees.

13. The apparatus of claim 9, wherein the detection surface includes a surface modification including a coating comprising a charged polymer to enhance adhesion of the plurality of target cells.

14. The apparatus of claim 13, wherein the coating is poly-L-lysine that is charged with (—NH$_3^+$).

15. The apparatus of claim 9, wherein:
the second surface is a bottom surface of the separation portion; and
the detection surface transitions into a third surface coplanar with or lower than the second surface.

16. The apparatus of claim 9, wherein:
the inlet portion defines an opening through which the sample can be conveyed into the inlet reservoir; and the detection surface is angled in an upward direction with respect to the opening.

17. The apparatus of claim 9, wherein:
the cartridge further comprises a hub located on the rotation axis;
the cartridge is configured to be removably coupled to the rotation element via the hub; and
a center of mass of the cartridge is located within the hub.

18. The apparatus of claim 9, wherein a ratio of a volume of the separation chamber and a volume of the detection chamber is at least about 2.0.

19. An apparatus, comprising:
a cartridge configured to be removably coupled to a rotation element configured to rotate the cartridge about a rotation axis to capture a plurality of target cells within a sample, the cartridge comprising:
an inlet portion defining an inlet reservoir configured to contain the sample;
a separation portion including a first surface and a second surface defining a separation chamber, the separation portion configured to contain a density medium having a density greater than a density of a first portion of the sample and less than a density of a second portion of the sample, the second portion including the plurality of target cells, the separation chamber configured to be fluidically coupled to the inlet reservoir such that at least the second portion of the sample can pass from the inlet reservoir to the separation chamber when the cartridge is rotated, wherein the first surface and the second surface are parallel to each other, the first surface and the second surface each being perpendicular to a distance between the first surface and the second surface; and
a detection portion including a first detection surface and a second detection surface, the first detection surface and the second detection surface each being perpendicular to a distance between the first detection surface and the second detection surface, the distance between the first detection surface and the second detection surface being substantially equal to or greater than the distance between the first surface and the second surface, the first detection surface forming a first boundary of a detection chamber, the second detection surface forming a second boundary of the detection chamber, the detection chamber fluidically coupled to the separation chamber such that at least the plurality of target cells can pass through the density medium and into the detection chamber, the first detection surface and the second detection surface each being nonparallel to at least one of the first surface or the second surface such that the plurality of target cells impinge on at least one of the first detection surface or the second detection surface when passing into the detection chamber, at least one of the first detection surface or the second detection surface configured to capture the plurality of target cells; and
a dilution reagent, wherein at least one of the dilution reagent or the density medium comprise any of an antifoaming agent, a wetting agent, a dispersant, or an emulsifier.

20. The apparatus of claim 19, wherein:
the distance between the first surface and the second surface is perpendicular to an axis that intersects a central location of the cartridge in a radial direction;
the inlet portion defines an opening through which the sample can be conveyed into the inlet reservoir; and at least one of the first detection surface or the second detection surface is angled in a downward direction with respect to the opening and bends in a downward direction with respect to the axis that intersects the central location of the cartridge in the radial direction.

21. The apparatus of claim 19, further comprising the density medium, the density medium having a density of between 1.01 g/cm3 and 1.13 g/cm3, and wherein the cartridge includes a density medium reservoir fluidically coupled to the separation chamber.

22. An apparatus, comprising:

a cartridge configured to be removably coupled to a rotation element configured to rotate the cartridge about a rotation axis to capture a plurality of target cells within a sample, the cartridge comprising:

an inlet portion defining an inlet reservoir configured to contain the sample;

a separation portion including a first surface and a second surface defining a separation chamber, the second surface being a bottom surface of the separation portion, the separation portion configured to contain a density medium having a density greater than a density of a first portion of the sample and less than a density of a second portion of the sample, the second portion including the plurality of target cells, the separation chamber configured to be fluidically coupled to the inlet reservoir such that at least the second portion of the sample can pass from the inlet reservoir to the separation chamber when the cartridge is rotated; and a detection portion including a detection surface that forms a boundary of a detection chamber, the detection chamber fluidically coupled to the separation chamber such that at least the plurality of target cells can pass through the density medium and into the detection chamber, the detection surface being non-parallel to at least one of the first surface or the second surface such that the plurality of target cells impinge on the detection surface when passing into the detection chamber, the detection surface being angled at a non-zero angle with respect to a radial axis defined by the cartridge that is normal to the rotation axis, the detection surface configured to capture the plurality of target cells, the detection surface transitioning into a third surface coplanar with or lower than the second surface; and a dilution reagent, wherein at least one of the dilution reagent or the density medium comprise any of an antifoaming agent, a wetting agent, a dispersant, or an emulsifier.

23. The apparatus of claim 22, further comprising the density medium, the density medium having a density of between 1.01 g/cm3 and 1.13 g/cm3, and wherein the cartridge includes a density medium reservoir fluidically coupled to the separation chamber.

* * * * *